United States Patent
Rhee et al.

(10) Patent No.: US 9,114,172 B2
(45) Date of Patent: Aug. 25, 2015

(54) RAPIDLY ACTING DRY SEALANT AND METHODS FOR USE AND MANUFACTURE

(71) Applicants: Baxter International Inc., Deerfield, IL (US); Baxter Healthcare S.A., Glattpark (Opfikon) (CH)

(72) Inventors: Woonza M. Rhee, Palo Alto, CA (US); Cary J. Reich, Los Gatos, CA (US); A. Edward Osawa, San Francisco, CA (US); Felix Vega, San Francisco, CA (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 13 days.

(21) Appl. No.: 13/781,326

(22) Filed: Feb. 28, 2013

(65) Prior Publication Data
US 2014/0072614 A1    Mar. 13, 2014

Related U.S. Application Data

(60) Division of application No. 13/457,178, filed on Apr. 26, 2012, now abandoned, which is a continuation of application No. 11/832,380, filed on Aug. 1, 2007.

(60) Provisional application No. 60/821,190, filed on Aug. 2, 2006.

(51) Int. Cl.
| | |
|---|---|
| *A61K 9/14* | (2006.01) |
| *A61K 38/39* | (2006.01) |
| *A61L 31/12* | (2006.01) |
| *A61L 24/10* | (2006.01) |
| *A61L 24/06* | (2006.01) |
| *A61K 47/42* | (2006.01) |
| *A61L 24/00* | (2006.01) |
| *A61L 31/04* | (2006.01) |
| *A61L 31/14* | (2006.01) |
| *A61K 9/70* | (2006.01) |
| *A61K 38/36* | (2006.01) |
| *A61K 38/48* | (2006.01) |
| *A61K 47/34* | (2006.01) |

(52) U.S. Cl.
CPC . *A61K 47/42* (2013.01); *A61K 9/70* (2013.01); *A61K 38/363* (2013.01); *A61K 38/4833* (2013.01); *A61K 47/34* (2013.01); *A61L 24/001* (2013.01); *A61L 24/0031* (2013.01); *A61L 24/06* (2013.01); *A61L 31/044* (2013.01); *A61L 31/145* (2013.01); *A61L 31/146* (2013.01)

(58) Field of Classification Search
None
See application file for complete search history.

(56) References Cited

U.S. PATENT DOCUMENTS

| | | | |
|---|---|---|---|
| 2,507,244 | A | 5/1950 | Correll |
| 2,558,395 | A | 6/1951 | Studer |
| 3,089,815 | A | 5/1963 | Kupelwieser et al. |
| 4,006,220 | A | 2/1977 | Gottlieb |
| 4,013,078 | A | 3/1977 | Feild |
| 4,124,705 | A | 11/1978 | Rothman et al. |
| 4,164,559 | A | 8/1979 | Miyata et al. |
| 4,179,400 | A | 12/1979 | Tsao et al. |
| 4,265,233 | A | 5/1981 | Sugitachi et al. |
| 4,291,013 | A | 9/1981 | Wahlig et al. |
| 4,292,972 | A | 10/1981 | Pawelchak et al. |
| 4,298,598 | A | 11/1981 | Schwarz et al. |
| 4,300,494 | A | 11/1981 | Graiff et al. |
| 4,347,234 | A | 8/1982 | Wahlig et al. |
| 4,362,567 | A | 12/1982 | Schwarz et al. |
| 4,377,572 | A | 3/1983 | Schwarz et al. |
| 4,424,208 | A | 1/1984 | Wallace et al. |
| 4,453,939 | A | 6/1984 | Zimmerman et al. |
| 4,482,386 | A | 11/1984 | Wittwer et al. |
| 4,515,637 | A | 5/1985 | Cioca |
| 4,536,387 | A | 8/1985 | Sakamoto et al. |
| 4,540,410 | A | 9/1985 | Wood et al. |
| 4,543,332 | A | 9/1985 | Jao et al. |
| 4,554,156 | A | 11/1985 | Fischer et al. |
| 4,600,574 | A | 7/1986 | Lindner et al. |
| 4,640,834 | A | 2/1987 | Eibl et al. |
| 4,655,211 | A | 4/1987 | Sakamoto et al. |
| 4,746,514 | A | 5/1988 | Warne |
| 4,749,689 | A | 6/1988 | Miyata et al. |
| 4,803,075 | A | 2/1989 | Wallace et al. |
| 4,818,517 | A | 4/1989 | Kwee et al. |
| 4,832,686 | A | 5/1989 | Anderson |
| 4,837,285 | A | 6/1989 | Berg et al. |

(Continued)

FOREIGN PATENT DOCUMENTS

| | | |
|---|---|---|
| EP | 0132983 A | 2/1985 |
| EP | 0376931 | 7/1990 |

(Continued)

OTHER PUBLICATIONS

Maok (Hemostatic Agents, Adjuncts to Control Bleeding, Today's O.R. Nurse, vol. 13.11 (1991) pp. 6-10; on Oct. 30, 2013 IDS).*
Ansell et al., "Gelfoam and Autologous Clot Embolization: Effect on Coagulation." *Investigative Radiology* vol. 13 (1978): pp. 115-120.
Barrow, D.L., et al.; "The Use of Greater Omentum Vascularized Free Flaps for Neurosurgical Disorders Requiring Reconstruction." *Journal of Neurosurgery*, vol. 60 (Feb. 1984): pp. 305-311.
Barton, et al., "Fibrin Glue as a Biologic Vascular Patch—A Comparative Study." (abstract posted at http://www.ncbi.nlm.nih.gov/ on Jan. 3, 2001) *Journal Surgical Research* vol. 40.5 (1986): pp. 510-513.

(Continued)

*Primary Examiner* — H. Sarah Park
(74) *Attorney, Agent, or Firm* — Kilpatrick Townsend & Stockton LLP

(57) ABSTRACT

Compositions, methods, and kits are provided for sealing applications. Compositions are prepared by combining a first cross-linkable component with a second cross-linkable component to form a porous matrix having interstices, and combining the porous matrix with a hydrogel-forming component to fill at least some of the interstices. The compositions exhibit minimal swelling properties.

24 Claims, 16 Drawing Sheets

(56) References Cited

U.S. PATENT DOCUMENTS

| | | |
|---|---|---|
| 4,891,359 A | 1/1990 | Saferstein et al. |
| 4,925,677 A | 5/1990 | Feijen |
| 4,946,870 A | 8/1990 | Partain, III et al. |
| 5,007,916 A | 4/1991 | Linsky et al. |
| 5,017,229 A | 5/1991 | Burns et al. |
| 5,023,082 A | 6/1991 | Friedman et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro et al. |
| 5,162,430 A | 11/1992 | Rhee et al. |
| 5,165,938 A | 11/1992 | Knighton |
| 5,178,883 A | 1/1993 | Knighton |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |
| 5,447,966 A | 9/1995 | Hermes et al. |
| 5,478,352 A | 12/1995 | Fowler |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,614,587 A | 3/1997 | Rhee et al. |
| 5,618,551 A | 4/1997 | Tardy et al. |
| 5,648,506 A | 7/1997 | Desai et al. |
| 5,667,839 A | 9/1997 | Berg |
| 5,672,336 A | 9/1997 | Sharma |
| 5,674,275 A | 10/1997 | Tang et al. |
| 5,690,675 A | 11/1997 | Sawyer et al. |
| 5,698,213 A | 12/1997 | Jamiolkowski et al. |
| 5,714,370 A | 2/1998 | Eibl et al. |
| 5,853,749 A | 12/1998 | Hobbs |
| 5,874,500 A | 2/1999 | Rhee et al. |
| 5,902,832 A | 5/1999 | Van Bladel et al. |
| 5,908,054 A | 6/1999 | Safabash et al. |
| 5,931,165 A | 8/1999 | Reich et al. |
| 5,959,735 A | 9/1999 | Maris et al. |
| 5,997,895 A | 12/1999 | Narotam et al. |
| 6,063,061 A | 5/2000 | Wallace et al. |
| 6,066,325 A | 5/2000 | Wallace et al. |
| 6,110,484 A | 8/2000 | Sierra |
| 6,129,761 A | 10/2000 | Hubbell |
| 6,166,130 A | 12/2000 | Rhee et al. |
| 6,179,872 B1 | 1/2001 | Bell et al. |
| 6,277,394 B1 | 8/2001 | Sierra |
| 6,312,474 B1 | 11/2001 | Francis et al. |
| 6,312,725 B1 | 11/2001 | Wallace et al. |
| 6,328,229 B1 | 12/2001 | Duronio et al. |
| 6,458,386 B1 | 10/2002 | Schacht et al. |
| 6,458,889 B1 | 10/2002 | Trollsas |
| 6,495,127 B1 * | 12/2002 | Wallace et al. ............ 424/78.03 |
| 6,624,245 B2 | 9/2003 | Wallace et al. |
| 6,706,690 B2 | 3/2004 | Reich et al. |
| 7,320,962 B2 | 1/2008 | Reich et al. |
| 7,435,425 B2 | 10/2008 | Qian et al. |
| 7,547,446 B2 | 6/2009 | Qian et al. |
| 7,871,637 B2 | 1/2011 | Qian et al. |
| 2002/0165337 A1 | 11/2002 | Wallace et al. |
| 2002/0193448 A1 | 12/2002 | Wallace et al. |
| 2003/0064109 A1 | 4/2003 | Qian et al. |
| 2004/0147465 A1 | 7/2004 | Jiang et al. |
| 2006/0147492 A1 | 7/2006 | Hunter et al. |
| 2006/0167561 A1 | 7/2006 | Odar et al. |
| 2008/0085316 A1 | 4/2008 | Qian et al. |
| 2008/0091277 A1 | 4/2008 | Deusch et al. |
| 2008/0187591 A1 | 8/2008 | Rhee et al. |
| 2008/0286376 A1 | 11/2008 | Qian et al. |
| 2009/0142396 A1 | 6/2009 | Odar et al. |
| 2010/0028309 A1 | 2/2010 | Odar et al. |
| 2010/0292717 A1 | 11/2010 | Petter-Puchner et al. |
| 2010/0318048 A1 | 12/2010 | Hoefinghoff et al. |
| 2012/0207813 A1 | 8/2012 | Rhee et al. |

FOREIGN PATENT DOCUMENTS

| | | |
|---|---|---|
| EP | 0132983 B2 | 12/1991 |
| EP | 0493387 | 7/1992 |
| EP | 0891193 | 1/1999 |
| EP | 0612252 B1 | 5/1999 |
| EP | 1084720 A1 | 3/2001 |
| EP | 1283063 A1 | 2/2003 |
| EP | 1484070 A1 | 12/2004 |
| EP | 1414370 B1 | 4/2007 |
| JP | 59-113889 | 6/1984 |
| JP | 05308969 | 11/1993 |
| JP | 6-254148 | 9/1994 |
| JP | 9-504719 | 5/1997 |
| JP | 07090241 A | 4/2007 |
| KR | 10-1991-0007847 B1 | 10/1991 |
| WO | 92/21354 | 12/1992 |
| WO | 92/22252 | 12/1992 |
| WO | 94/27630 A1 | 12/1994 |
| WO | 95/12371 | 5/1995 |
| WO | 95/15747 | 6/1995 |
| WO | 86/00912 | 2/1996 |
| WO | 96/04025 | 2/1996 |
| WO | 96/06883 | 3/1996 |
| WO | 96/10374 | 4/1996 |
| WO | 96/10428 | 4/1996 |
| WO | 96/14368 | 5/1996 |
| WO | 96/39159 | 12/1996 |
| WO | 97/22371 | 6/1997 |
| WO | 97/37694 A1 | 10/1997 |
| WO | 98/08550 A1 | 3/1998 |
| WO | 99/13902 A1 | 3/1999 |
| WO | 02/22059 A1 | 3/2002 |
| WO | 02/22184 A2 | 3/2002 |
| WO | 02/070594 A2 | 9/2002 |
| WO | 03/007845 A1 | 1/2003 |
| WO | 2004/108179 A1 | 12/2004 |
| WO | 2006/031358 A | 3/2006 |
| WO | 2006/118460 A1 | 11/2006 |
| WO | 2007/001926 | 1/2007 |
| WO | 2007/137839 A2 | 12/2007 |
| WO | 2007/137839 A3 | 12/2007 |
| WO | 2008/016983 A2 | 2/2008 |

OTHER PUBLICATIONS

Baxter product brochure for TissuFleece E, TissuCone E and TissuFoil E (2003).

(56) References Cited

OTHER PUBLICATIONS

Baxter Product Catalogue; Collagen; 4 pages (2006).
Baxter, "GentaFleece Collagen Fleece—Version 5 : Collagen Sponge with antibiotic protection for surgical use," Retrieved from http://www.advancingbiosurgery.com/en_EU/downloads/ifu_gentafleece.pdf, Mar. 2002, 2 pages. English portion second column of first page.
Boyers, et al., "Reduction of Postoperative Pelvic Adhesions in the Rabbit with Gore-Tex Surguical Membrane," *Fertility and Sterility* vol. 49.6 (1988): pp. 1066-1070.
Bruck, S. D., Ed., *Controlled Drug Delivery*. CRC Press, Boca Raton, FL (1983) A title page and table of contents.
Cantor, et al., "Gelfoam and Thrombin in Gastrointestinal Bleeding: An Experimental Study." (1950): pp. 890-893.
Cantor, et al., "Gelfoam and Thrombin in Treatment of Massive Gastroduodenal Hemmorhage: A Preliminary Report." *The American Journal of Surgery* (1950): pp. 883-887.
Cantor, et al., "Gelfoam and Thrombin in Treatment of Massive Upper Gastroduodenal Hemorrhage." *The American Journal of Surgery* (1951): pp. 230-235.
Chaplin, J.M., et al., "Use of an Acellular Dermal Allograft for Dural Replacement: An Experimental Study." *Neurosurgery* vol. 45.2 (Aug. 1999): pp. 320-327.
Cheung, David T., et al., "Mechanism of crosslinking of proteins by glutaraldehyde IV: In Vitro and In Vivo stability of a crosslinked collagen matrix." *Connective Tissue Research*, vol. 25.1 (1990): pp. 27-34.
Christensen, et al., "Qualitative Description of the Wurster-Based Fluid-Bed Coating Process." *Drug Development and Industrial Pharmacy* vol. 23.5 (1997): pp. 451-463.
Collins, et al., "Enemata of Gelfoam-Milk Suspension Combined with Thrombin Solution to Control Massive Hemorrhage Following Anorectal Surgery." *American Journal of Proctology* vol. 2 (1951): pp. 60-63.
Collins, Ronald et al., "Use of Collagen Film as a Dural Substitute: Preliminary Animal Studies." *Journal of Biomedical Materials Research* vol. 25 (1991): pp. 267-276.
Edgerton, et al., "Vascular Hamartomas and Hemangiomos: Classification and Treatment." *Southern Medical Journal* vol. 75.12 (1982): pp. 1541-1547.
Filippi, R., et al., "Bovine Pericardium for Duraplasty: Clinical Results in 32 Patients." *Neurosurgical Review* vol. 20 (2001): pp. 103-107.
Gibble, et al., "Fibrin glue: the perfect operative sealant?" *Transfusion* vol. 30.8 (1990): pp. 741-747.
Guoping, Chen, et al., "Scaffold Design for Tissue Engineering." *Macromolecular Bioscience* (2002): pp. 67-77.
Heller, et al., "Release of Norethindrone from Poly(Ortho Esters)." *Polymer Engineering Science* vol. 21 (1981): pp. 727-731.
Hieb, Lee D., et al., "Spontaneous Postoperative Cerebrospinal Fluid Leaks Following Application of Anti-Adhesion Barrier Gel." *Spine* vol. 26.7 (2001): pp. 748-751.
Hood, et al., "Efficacy of Topical Hemostat Floseal Matrix in Vascular Surgery." 24th World Congress of the International Society for Cardiovascular Surgery (Sep. 12-16, 1999), 2 pages total.
Hotz, et al., "Collagen and Fibrin as Biologic Binders from Granular Hydroxyapatite." (abstract posted at http://www.ncbi.nlm.nih.gov/ on Jan. 3, 2001) *Dtsh. Z. Mund. Kiefer Geichtshir*. vol. 13.4 (1989): pp. 296-300.
Jeong, et al., "Biodegradable Block Copolymers as Injectible Drig-Delivery Systems." *Nature* vol. 388 (1997): pp. 860-862.
Jonas, Richard A., et al., "A new sealant for knitted Dacron prostheses: Minimally cross-linked gelatin." *Journal of Vascular Surgery* vol. 7.3 (1988): pp. 414-419.
Kim, Kee D., et al., "Reduction in Leg Pain and Lower-Extremity Weakness with Oxiplex/SP Gel for 1 Year after Laminectomy, Laminotomy, and Discectomy." *Neurosurgical Focus* vol. 17.1 (2004): pp. 1-6.
Kline, D.G., "Dural Replacement with Resorbable Collagen." *Archives of Surgery* vol. 91 (Dec. 1965): pp. 924-929.
Knopp, U., "A new collagen foil versus a cadaveric dura graft for dural defects-a comparative animal experimental study." EANS—12th European Congress of Neurosurgery, Lisbon (Sep. 7-12, 2003): pp. 663-666.
Kofidis, T., et al., "Clinically established Hemostatis Scaffold (Tissue Fleece) as Biomatrix in Tissue- and organ-engineering research." *Tissue Engineering* vol. 9.3 (2003): pp. 517-523.
Krill, et al., "Topical Thrombin and Powdered Gelfoam: An Efficient Hemostatic Treatment for Surgery." *Journal—Tennessee State Dental Association* vol. 66.2 (1986): pp. 26-27.
Kuhn, J., et al., "Bilateral Subdural Haemotomata and Lumbar Pseudomeningocele Due to a Chronic Leakage of Liquor Cerebrospinalis after a Lumbar Disectomy with the Application of ADCON-L Gel", *Journal of Neurology, Neurosurgery & Psychiatry* vol. 76 (2005): pp. 1031-1033.
Langer, et al., "Chemical and Physical Structure of Polymers as Carriers for Controlled Release of Bioactive Agents: A Review" *Journal of Macromolecular Science, Reviews on Macromolecular Chemistry and Physics* vol. C23.1 (1983): pp. 61-126.
Laquerriere, A., et al., "Experimental Evaluation of Bilayered Human Collagen as a Dural Substitute." *Journal of Neurosurgery* vol. 78 (1993): pp. 487-491.
Larson, Paul O., "Topical Hemostatic Agents for Dermatologic Surgery." *The Journal of Dermatologic Surgery and Oncology* vol. 14.6 (1988): pp. 623-632.
Le, A. X., et al., "Unrecognized Durotomy After Lumbar Discectomy: A Report of Four Cases Associated with the Use of ADCON-L." *Spine* vol. 26.1, (2001): pp. 115-118.
Lee, J.F., et al., "Experimental Evaluation of Silicone-Coated Dacron and Collagen Fabric-Film Laminate as Dural Substitutes." *Journal of Neurosurgery* vol. 27 (1967): pp. 558-564.
Leong, et al., "Polyanhydrides for Controlled Release of Bioactive Agents." *Biomaterials* vol. 7 (1986): pp. 364-371.
Leong, et al., "Polymeric Controlled Drug Delivery." *Advanced Drug Delivery Reviews* vol. 1 (1987): pp. 199-233.
Maok, "Hemostatic Agents." *Today's OR Nurse* vol. 13.11 (1991): pp. 6-10.
Maser, et al., "Synthesis of Polyurethanes and Investigation of their Hydrolytic Stability." *Journal of Polymer Science: Polymer Symposium* vol. 66 (1979): pp. 259-268.
Matsumoto, K., et al., "A Gelatin Coated Collagen-Polyglycolic Acid Composite Membrane as a Dural Substitute." *American Society for Artificial Internal Organs Journal* (2001): pp. 641-645.
Maurer, P.K., et al., "Vicryl (Polyglactin 910) Mesh as a Dural Substitute." *Journal of Neurosurgery* vol. 63 (Sep. 1985): pp. 448-452.
McClure, et al., "Massive Gastroduodenal Hemorrhage: Treatment with Powdered Gelfoam and Buffered Thrombin Solution." *Surgery* vol. 32 (1952): pp. 630-637.
McPherson, J. M., et al., "An examination of the biologic response to injectable, glutaraldehyde cross-linked collagen implants." *Journal of Biomedical Materials Research* vol. 20.1 (1986): pp. 93-107.
McPherson, J. M., et al., "The preparation and physiochemical characterization of an injectable form of reconstituted, glutaraldehyde cross-linked, bovine corium collagen." Journal of Biomedical Materials Research vol. 20.1 (1986): pp. 79-92.
McPherson, John M., et al., "The Effects of Heparin on the Physiochemical Properties of Reconstituted Collagen." *Collagen and Related Research* vol. 8.1 (1988): pp. 65-82.
Meddings, N., et al., "Collagen Vicryl—A New Dural Prosthesis," *Acta Neurochir*. vol. 117 (1992): pp. 53-58.
Mello, L.R., et al., "Duraplasty with Biosynthetic Cellulose: An Experimental Study." *Journal of Neurosurgery* vol. 86 (Jan. 1997): pp. 143-150.
Narotam, P.K., et al., "A Clinicopathological Study of Collagen Sponge as a Dural Graft in Neurosurgery." *Journal of Neurosurgery* vol. 82 (Mar. 1995): pp. 406-412.
Narotam, P.K., et al., "Experimental Evaluation of Collagen Sponge as a Dural Graft." *British Journal of Neurosurgery* vol. 7 (1993):pp. 635-641.
Nimni, M. E., et al., "Chemically modified collagen: A natural biomaterial for tissue replacement." *Journal of Biomedical Materials Research* vol. 21.6 (1987): pp. 741-771.

(56) References Cited

OTHER PUBLICATIONS

Nimni, Marcel E., "The cross-linking and structure modification of the collagen matrix in the design of cardiovascular prosthesis." *Journal of Cardiac Surgery* vol. 3.4 (1988): pp. 523-33.
O'Neill, P., et al., "Use of Porcine Dermis as Dural Substitute in 72 Patients." *Journal of Neurosurgery* vol. 61 (Aug. 1984): pp. 351-354.
Palm, S.J., et al., "Dural Closure with Nonpenetrating Clips Prevents Meningoneural Adhesions: An Experimental Study in Dogs." *Neurosurgery* vol. 45.4 (Oct. 1999):pp. 875-882.
Parizek, J., et al., "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery," *Acta Neurochir* vol. 139 (1997): pp. 827-838.
Park, Y-K., at al., "Prevention of Arachnoiditis and Postoperative Tethering of the Spinal Cord with Gore-Tex Surgical Membrane: An Experimental Study with Rats," *Neurosurgery* vol. 42.4 (Apr. 1998): pp. 813-824.
PCT International Preliminary Report on Patentability and Written Opinion mailed Feb. 17, 2009, International Application No. PCT/US2007/074984, 8 pages.
Pietrucha, K., "New Collagen Implant as Dural Substitute." *Biomaterials* vol. 12 (Apr. 1991): pp. 320-323.
Pitt, et al., *Controlled Release of Bioactive Materials*. Ed. R. Baker, New York: Academic Press, 1980.
Porchet, Francois, "Inhibition of Epidural Fibrosis with ADCON-L: Effect on Clinical Outcome One Year Following Re-operation for Recurrent Lumbar Radiculopathy." 1998, pp. 1-10.
Raul, J.S., et al., "Utilisation du Polyester Urethane (NEURO-PATCH® ) Comme Substitut Dural." *Neurochirugie* vol. 49.2-3 (2003): pp. 83-89. English abstract only on p. 83.
Reddy, M., et al., "A Clinical Study of a Fibrinogen-Based Collagen Fleece for Dural Repair in Neurosurgery." *Acta Neurochirugie* vol. 144 (2002): pp. 265-269.
Riley, et al., "Percutaneous Liver Biopsy with Plugging of Needle Track: A Safe Method for Use in Patients with Impaired Coagulation." *Lancet* (Aug. 25, 1984): p. 436.
Rosenblatt, Joel, et al., "Effect of electrostatic forces on the dynamic rheological properties of injectable collagen biomaterials." *Biomaterials* vol. 13.12 (1992): pp. 878-86.
Rosenblatt, Joel, et al., "Injectable collagen as a pH-sensitive hydrogel." *Biomaterials* vol. 15.12 (1994): pp. 985-95.
Ross, Jeffrey S., et al., "Association Between Peridural Scar and Recurrent Radicular Pain After Lumbar Discectomy: Magnetic Resonance Evaluation." *Neurosurgery* (1996): pp. 855-863.
Rossler, B., et al., "Collagen microparticles: preparation and properties." *Journal of Microencapsulation* vol. 12.1 (Jan.-Feb. 1995): pp. 49-57.
San-Galli, F., et al., "Experimental Evaluation of a Collagen-Coated Vicryl Mesh as a Dural Substitute." *Neurosurgery* vol. 30.3 (1992): pp. 396-401.
Shaffrey, C.I., et al., "Neurosurgical Applications of Fibrin Glue: Augmentation of Dural Closure in 134 Patients." *Neurosurgery* vol. 26.2 (1990): pp. 207-210.
Sidman, et al., "Biodegradable, Implantable Sustained Release Systems Based on Glutamic Acid Copolymers." *Journal of Membrane Science* vol. 7 (1979): pp. 227-291.

Smith, K. A., et al., "Delayed Postoperative Tethering of the Cervical Spinal Cord." *Journal of Neurosurgery* vol. 81 (Aug. 1994): pp. 196-201.
Springorum, H.W., "Die Verwendung von Kollagenfolien zur Uberbruckung von Defekten des Gleitgewebes bei Achillotenotomien and Achillessehnenrupturen." *Akt. Traumata*. vol. 15 (1985): pp. 120-121. English abstract only on p. 120.
Stricker, A., et al., "Die Verwendung von TissuFoil Membran bei der Sinusbodenaugmentation." *Ellipse* vol. 17.1 (2001): pp. 1-5. English abstract only on p. 1.
Sugitachi, et al., "A Newly Devised Chemo-embolic Agent, G.T. XIII-ADM." (English abstract posted at http://www.ncbi.nlm.nih.gov/ on Jan. 3, 2001) *Gan. To. Kagaku Ryoho*. vol. 12.10 (1985): pp. 1942-1943.
Sugitachi, et al., "Locoregional Therapy in Patients with Malignant Pleural Effusion—Two Different Kinds of BAC Therapy" (English abstract posted at http://www.ncbi.nlm.nih.gov/ on Jan. 3, 2001) *Gan. To. Kagaku Ryoho*. vol. 19.10 (1992): pp. 1640-1643.
Sugitachi, et al., "Preoperative Transcatheter Arterial Chemo-embolization for Locally Advanced Breast Cancer: Application for New Thrombotic Materials." *The Japanese Journal of Surgery* vol. 13.5 (1983): pp. 456-458.
TissuFleece E, Version 5, Package Leaflet, Baxter International Inc., 2003, 8 pages. English portion of instructions for use.
Tobin, et al., "Plugged Liver Biopsy in Patients with Impaired Coagulation." *Digestive Diseases and Science* vol. 34.1 (1989): pp. 13-15.
Tucker, et al., *Absorbable Gelatin (Gelfoam) Sponge*. Springfiled, Illinois: Charles T. Thomas, 1965, pp. 3-125.
Vander Salm, et al., "Reduction of Sternal Infection by Application of Topical Vancomycin." *Journal of Thoracic Surgery* vol. 98 (1989): pp. 618-622.
Vinas, F.E., et al., "Evaluation of Expanded Polytetrafluoroethylene (ePTFE) versus Polydioxanone (PDS) for the Repair of Dura Mater Defects." *Neurological Research* vol. 21 (Apr. 1999): pp. 262-268.
Wallace, D. G., et al., "Injectable cross-linked collagen with improved flow properties." *Journal of Biomedical Materials Research* vol. 23.8 (Aug. 1989): pp. 931-45.
Wallace, Donald, "The relative contribution of electrostatic interactions to stabilization of collagen fibrils." *Biopolymers* vol. 29.6-7 (May-Jun. 1990): pp. 1015-1026.
Warren, W.L., et al., "Dural Repair Using Acellular Human Dermis: Experience with 200 Cases: Technique Assessment." *Neurosurgery* vol. 46.6 (Jun. 2000): pp. 1391-1396.
Yuki, et al., "Effects of Endoscopic Variceal Sclerotherapy using GT XIII on Blood Coagulation Tests and the Renal Kallikrein-kinin System." (English abstract posted at http://www.ncbi.nlm.nih.gov/ on Jan. 3, 2001) *Gastroenterology Japan* vol. 25.5 (1990): pp. 561-567.
Ziegelaar, B.W., et al., "The characterisation of human respiratory epithelial cells cultured on reabsorbable scaffolds: first steps towards a tissue engineered tracheal replacement." *Biomaterials* vol. 23 (2002): pp. 1425-1438.
Ziegelaar, B.W., "Tissue Engineering of a Tracheal Equivalent." Doctoral Thesis at Ludwig Maximilians University, Munich, Germany, 2004, 25 pages.
Zins, et al., "US-Guided Percutaneous Liver Biopsy with Plugging of the Needle Track: A Prospective Study in 72 High-Rish Patients." *Radiology* vol. 184.3 (1992): pp. 841-843.

\* cited by examiner

-ALA-GLY-PRO-ARG-GLY-GLU-4HYP-GLY-PRO-

| SAMPLE ID | PAN ID | DRY WT | 30 sec | 0.6 hr 0.025 d | 73 min 0.05 d | 2 hr 0.083 d | 17.4 hr 0.73 d | 1 day | 3.8 days | 4.8 days | 5.8 days | 7.8 days | 10.8 days | 11.8 days | 12.8 days | 13.8 days | 17.8 days |
|---|---|---|---|---|---|---|---|---|---|---|---|---|---|---|---|---|---|
| 30% 5+5+6g | 1 | 1.49 | 1.59 | 2.13 | 2.33 | 2.70 | 4.41 | 4.67 | 5.63 | 6.02 | 6.13 | 6.53 | 7.00 | 7.02 | 6.61 | 6.52 | 5.00 |
|  | 2 | 1.51 | 1.68 | 2.14 | 2.36 | 2.62 | 4.27 | 4.53 | 5.51 | 5.86 | 6.03 | 6.89 | 6.93 | 6.98 | 6.97 | 6.73 | 4.91 |
|  | 3 | 1.46 | 1.54 | 2.00 | 2.23 | 2.50 | 4.06 | 4.30 | 5.37 | 5.72 | 5.91 | 6.39 | 6.92 | 6.86 | 6.69 | 6.54 | 4.56 |
|  | AVG |  |  | 2.09 |  | 2.61 | 4.25 | 4.50 | 5.50 | 5.86 | 6.02 | 6.44 | 6.98 | 6.96 | 6.72 | 6.60 | 4.83 |
|  | StDev |  |  | 0.07 |  | 0.10 | 0.16 | 0.18 | 0.13 | 0.15 | 0.11 | 0.08 | 0.10 | 0.09 | 0.13 | 0.10 |  |
|  | % rsd |  |  | 3.53 |  | 3.96 | 3.81 | 4.08 | 2.39 | 2.57 | 1.78 |  |  |  |  |  |  |
| 20% 5+5+6g | 1 | 1.48 | 1.62 | 2.26 | 2.54 | 2.88 | 4.22 | 4.33 | 5.04 | 5.21 | 5.08 | 5.08 | 5.11 | 5.32 | 5.02 | 5.07 | 3.76 |
|  | 2 | 1.50 | 1.71 | 2.36 | 2.70 | 3.03 | 4.38 | 4.51 | 5.09 | 5.24 | 5.19 | 5.06 | 5.10 | 5.03 | 4.84 | 4.75 | 3.20 |
|  | 3 | 1.51 | 1.59 | 2.01 | 2.25 | 2.49 | 3.71 | 3.89 | 4.57 | 4.77 | 4.72 | 4.77 | 4.96 | 4.90 | 4.88 | 4.77 | 2.72 |
|  | AVG |  |  | 2.21 |  | 2.80 | 4.10 | 4.24 | 4.90 | 5.07 | 4.99 | 4.97 | 5.06 | 5.08 | 4.92 | 4.86 | 3.25 |
|  | StDev |  |  | 0.18 |  | 0.29 | 0.35 | 0.32 | 0.29 | 0.27 | 0.24 | 0.18 | 0.08 | 0.22 | 0.10 | 0.19 |  |
|  | % rsd |  |  | 7.94 |  | 10.31 | 8.55 | 7.48 | 5.88 | 5.25 | 4.82 |  |  |  |  |  |  |
| 10% 5+5+6g | 1 | 1.68 | 1.91 | 2.73 | 3.02 | 3.48 | 4.84 | 4.92 | 4.68 | 4.80 | 4.70 | 4.49 | 4.52 | 4.33 | 4.06 | 3.93 | 2.89 |
|  | 2 | 1.53 | 2.01 | 2.60 | 2.88 | 3.22 | 3.75 | 3.76 | 4.11 | 4.10 | 3.97 | 3.38 | 3.49 | 3.34 | 3.24 | 2.99 | 2.02 |
|  | 3 | 1.54 | 1.80 | 2.68 | 2.97 | 3.34 | 4.19 | 4.28 | 4.52 | 4.50 | 4.46 | 4.22 | 4.00 | 3.76 | 3.58 | 3.35 | 2.48 |
|  | AVG |  |  | 2.67 |  | 3.35 | 4.16 | 4.12 | 4.44 | 4.47 | 4.37 | 4.03 | 4.00 | 3.81 | 3.63 | 3.42 | 2.46 |
|  | StDev |  |  | 0.07 |  | 0.13 | 0.39 | 0.32 | 0.30 | 0.35 | 0.37 | 0.58 | 0.51 | 0.50 | 0.41 | 0.47 |  |
|  | % rsd |  |  | 2.51 |  | 3.95 | 9.45 | 7.66 | 6.71 | 7.77 | 8.51 |  |  |  |  |  |  |
| 5% 5+5+6g | 1 | 1.49 | 1.83 | 2.57 | 2.70 | 3.05 | 3.58 | 3.30 | 3.71 | 3.85 | 3.69 | 3.30 | 3.06 | 2.70 | 2.70 | 2.41 | 1.06 |
|  | 2 | 1.44 | 2.01 | 2.57 | 2.83 | 3.16 | 3.76 | 3.68 | 3.85 | 3.99 | 3.83 | 3.23 | 3.07 | 2.86 | 2.80 | 2.52 | 1.14 |
|  | 3 | 1.39 | 1.75 | 2.73 | 2.63 | 3.33 | 4.09 | 3.93 | 4.23 | 4.32 | 4.08 | 3.79 | 3.23 | 2.79 | 2.21 | 2.07 | 1.02 |
|  | AVG |  |  | 2.64 |  | 3.18 | 3.81 | 3.64 | 3.93 | 4.05 | 3.87 | 3.44 | 3.12 | 2.74 | 2.53 | 2.33 | 1.07 |
|  | StDev |  |  | 0.08 |  | 0.14 | 0.26 | 0.32 | 0.27 | 0.24 | 0.20 | 0.30 | 0.09 | 0.09 | 0.28 | 0.23 |  |
|  | % rsd |  |  | 3.16 |  | 4.31 | 6.76 | 8.82 | 6.93 | 5.89 | 5.10 |  |  |  |  |  |  |

FIG. 12

| | 30 min | 73 min | 2 hr | 17.4 hr | 1 day | 3.8 days | 4.8 days | 5.8 days | 7.8 days | 10.8 days | 11.8 days | 12.8 days | 13.8 days | 17.8 days |
|---|---|---|---|---|---|---|---|---|---|---|---|---|---|---|
| | 0.025 | 0.053 | 0.060 | 0.734 | 1d | | | | | | | | | |
| | 1.338 | 1.500 | 1.700 | 2.772 | 2.936 | 3.540 | 3.786 | 3.884 | 4.109 | 4.402 | 4.414984 | 4.184998 | 4.104045 | 3.145939 |
| | 1.270 | 1.402 | 1.558 | 2.536 | 2.695 | 3.276 | 3.483 | 3.592 | 3.797 | 4.119 | 4.149540 | 4.081253 | 3.990871 | 2.919939 |
| | 1.306 | 1.450 | 1.627 | 2.601 | 2.558 | 3.436 | 3.724 | 3.852 | 4.156 | 4.508 | 4.461564 | 4.361005 | 4.239805 | 2.972888 |
| | 1.305 | 1.431 | 1.629 | 2.656 | 2.730 | 3.437 | 3.684 | 3.763 | 4.024 | 4.363 | 4.342032 | 4.198772 | 4.120407 | 3.012739 |
| | 0.034 | 0.049 | 0.071 | 0.118 | 0.191 | 0.142 | 0.160 | 0.157 | 0.189 | 0.213 | 0.168315 | | | |
| | | | | | | | | | | | | | | |
| | 1.367 | 1.559 | 1.771 | 2.590 | 2.656 | 3.084 | 3.199 | 3.119 | 3.110 | 3.139 | 3.285 | 3.084 | 3.110 | 2.290088 |
| | 1.377 | 1.577 | 1.774 | 2.561 | 2.635 | 2.977 | 3.065 | 3.026 | 2.961 | 2.981 | 2.988 | 2.830 | 2.777 | 1.921773 |
| | 1.268 | 1.418 | 1.559 | 2.335 | 2.449 | 2.876 | 3.001 | 2.911 | 3.000 | 3.123 | 3.063 | 3.073 | 3.005 | 1.714848 |
| | 1.344 | 1.518 | 1.701 | 2.495 | 2.580 | 2.962 | 3.088 | 3.009 | 3.026 | 3.081 | 3.046 | 2.998 | 2.964 | 1.978319 |
| | 0.060 | 0.086 | 0.123 | 0.140 | 0.114 | 0.109 | 0.101 | 0.075 | 0.082 | 0.087 | 0.164 | 0.143 | 0.170 | |
| | | | | | | | | | | | | | | |
| | 1.426 | 1.474 | 1.820 | 2.370 | 2.350 | 2.446 | 2.506 | 2.456 | 2.346 | 2.360 | 2.765 | 2.119 | 2.082 | 1.510321 |
| | 1.291 | 1.436 | 1.601 | 1.865 | 1.867 | 2.041 | 2.041 | 1.973 | 1.682 | 1.734 | 1.661 | 1.611 | 1.466 | 1.020333 |
| | 1.469 | 1.660 | 1.854 | 2.320 | 2.378 | 2.513 | 2.501 | 2.476 | 2.342 | 2.221 | 2.090 | 1.991 | 1.859 | 1.378867 |
| | 1.334 | 1.552 | 1.758 | 2.167 | 2.163 | 2.333 | 2.349 | 2.301 | 2.124 | 2.105 | 2.105 | 1.907 | 1.730 | 1.298874 |
| | 1.402 | 1.518 | 1.708 | 2.495 | 2.80 | 2.962 | 3.088 | 3.009 | 3.026 | 3.081 | 3.046 | 2.998 | 2.964 | |
| | 0.061 | 0.112 | 0.157 | 0.260 | 0.260 | 0.255 | 0.267 | 0.264 | 0.382 | 0.329 | 0.311 | 0.265 | 0.288 | |
| | | | | | | | | | | | | | | |
| | 1.406 | 1.474 | 1.668 | 1.953 | 1.800 | 2.026 | 2.104 | 2.014 | 1.800 | 1.672 | 1.522 | 1.478 | 1.315 | 0.570770 |
| | 1.356 | 1.456 | 1.530 | 1.877 | 1.820 | 1.909 | 1.982 | 1.900 | 1.604 | 1.524 | 1.320 | 1.320 | 1.252 | 0.565597 |
| | 1.465 | 1.480 | 1.875 | 2.571 | 2.214 | 2.382 | 2.432 | 2.300 | 2.134 | 1.817 | 1.571 | 1.245 | 1.164 | 0.573536 |
| | 1.409 | 1.470 | 1.708 | 2.133 | 1.947 | 2.106 | 2.173 | 2.071 | 1.846 | 1.671 | 1.471 | 1.352 | 1.244 | 0.569825 |
| | 0.055 | 0.013 | 0.151 | 0.301 | 0.231 | 0.248 | 0.223 | 0.206 | 0.268 | 0.147 | 0.133 | 0.116 | 0.076 | |

FIG.13

RAPIDLY ACTING DRY SEALANT AND METHODS FOR USE AND MANUFACTURE

CROSS-REFERENCES TO RELATED APPLICATIONS

This application is a divisional of U.S. patent application Ser. No. 13/457,178 filed Apr. 26, 2012, which is a continuation of U.S. patent application Ser. No. 11/832,380 filed Aug. 1, 2007, which claims the benefit of priority from U.S. Patent Application No. 60/821,190 filed Aug. 2, 2006. This application is also related to U.S. Pat. Nos. 5,874,500, 6,063,061, 6,066,325, 6,166,130, and 6,458,889. The contents of each of these filings are hereby incorporated by reference.

BACKGROUND OF THE INVENTION

U.S. Pat. No. 5,162,430, issued Nov. 10, 1992, to Rhee et al. discusses collagen-synthetic polymer conjugates prepared by covalently binding collagen to synthetic hydrophilic polymers such as various derivatives of polyethylene glycol. U.S. Pat. No. 5,324,775, issued Jun. 28, 1994, to Rhee et al. discusses various insert, naturally occurring, biocompatible polymers (such as polysaccharides) covalently bound to synthetic, non-immunogenic, hydrophilic polyethylene glycol polymers. U.S. Pat. No. 5,328,955, issued Jul. 12, 1994, to Rhee et al. discusses various activated forms of polyethylene glycol and various linkages which can be used to produce collagen-synthetic polymer conjugates having a range of physical and chemical properties.

Ser. No. 08/403,358, filed Mar. 14, 1995, discusses a crosslinked biomaterial composition that is prepared using a hydrophobic crosslinking agent, or a mixture of hydrophilic and hydrophobic crosslinking agents. Hydrophobic crosslinking agents can include any hydrophobic polymer that contains, or can be chemically derivatized to contain, two or more succinimidyl groups.

U.S. Pat. No. 5,580,923, issued Dec. 3, 1996, to Yeung et al. discusses a composition useful in the prevention of surgical adhesions comprising a substrate material and an anti-adhesion binding agent, where the substrate material preferably comprises collagen and the binding agent preferably comprises at least one tissue-reactive functional group and at least one substrate-reactive functional group.

U.S. Pat. No. 5,614,587, issued Mar. 25, 1997, to Rhee et al. discusses bioadhesive compositions comprising collagen crosslinked using a multifunctionally activated synthetic hydrophilic polymer, as well as methods of using such compositions to effect adhesion between a first surface and a second surface, wherein at least one of the first and second surfaces can be a native tissue surface.

Japanese patent publication No. 07090241 discusses a composition used for temporary adhesion of a lens material to a support, to mount the material on a machining device, comprising a mixture of polyethylene glycol, having an average molecular weight in the range of 1000-5000, and poly-N-vinylpyrrolidone, having an average molecular weight in the range of 30,000-200,000.

West and Hubbell, Biomaterials (1995) 16:1153-1156, discuss the prevention of post-operative adhesions using a photopolymerized polyethylene glycol-co-lactic acid diacrylate hydrogel and a physically crosslinked polyethylene glycol-co-polypropylene glycol hydrogel, Poloxamer 407®.

U.S. Pat. Nos. 5,672,336 and 5,196,185 describe a wound dressing comprising a micro-particulate fibrillar collagen having a particle size of 0.5-2.0 μm. This composition generally comprises an aqueous phase and may not form a hydrogel as described in the present invention. U.S. Pat. No. 5,698,213 describes a cross-linked aliphatic poly-ester hydrogel useful as an absorbable surgical device and drug delivery vehicle. U.S. Pat. No. 5,674,275 describes an acrylate or methacrylate based hydrogel adhesive. U.S. Pat. No. 5,306,501 describes a polyoxyalkylene based thermoreversible hydrogel useful as a drug delivery vehicle.

U.S. Pat. Nos. 4,925,677 and 5,041,292 describe a hydrogel comprising a protein component cross-linked with a polysaccharide or mucopolysaccharide and useful as a drug delivery vehicle.

Biodegradable injectable drug delivery polymers are described in U.S. Pat. No. 5,384,333 and by Jeong et al. (1997) "Nature," 388:860-862. Biodegradable hydrogels for controlled released drug delivery are described in U.S. Pat. No. 4,925,677. Resorbable collagen-based drug delivery systems are described in U.S. Pat. Nos. 4,347,234 and 4,291,013. Aminopolysaccharide-based biocompatible films for drug delivery are described in U.S. Pat. Nos. 5,300,494 and 4,946,870. Water soluble carriers for the delivery of taxol are described in U.S. Pat. No. 5,648,506.

Polymers have been used as carriers of therapeutic agents to effect a localized and sustained release (Langer, et al., Rev. Macro. Chem. Phys., C23 (1), 61, 1983; Controlled Drug Delivery, Vol. I and II, Bruck, S. D., (ed.), CRC Press, Boca Raton, Fla., 1983; Leong et al., Adv. Drug Delivery Review, 1:199, 1987). These therapeutic agent delivery systems simulate infusion and offer the potential of enhanced therapeutic efficacy and reduced systemic toxicity.

Other classes of synthetic polymers which have been proposed for controlled release drug delivery include polyesters (Pitt, et al., in Controlled Release of Bioactive Materials, R. Baker, Ed., Academic Press, New York, 1980); polyamides (Sidman, et al., Journal of Membrane Science, 7:227, 1979); polyurethanes (Maser, et al., Journal of Polymer Science, Polymer Symposium, 66:259, 1979); polyorthoesters (Heller, et al., Polymer Engineering Scient, 21:727, 1981); and polyanhydrides (Leong, et al., Biomaterials, 7:364, 1986).

Collagen-containing compositions which have been mechanically disrupted to alter their physical properties are described in U.S. Pat. Nos. 5,428,024; 5,352,715; and 5,204,382. These patents generally relate to fibrillar and insoluble collagens. An injectable collagen composition is described in U.S. Pat. No. 4,803,075. An injectable bone/cartilage composition is described in U.S. Pat. No. 5,516,532. A collagen-based delivery matrix comprising dry particles in the size range from 5 μm to 850 μm which may be suspended in water and which has a particular surface charge density is described in WO 96/39159. A collagen preparation having a particle size from 1 μm to 50 μm useful as an aerosol spray to form a wound dressing is described in U.S. Pat. No. 5,196,185. Other patents describing collagen compositions include U.S. Pat. Nos. 5,672,336 and 5,356,614. A polymeric, non-erodible hydrogel that may be cross-linked and injected via a syringe is described in WO 96/06883.

The following pending applications, assigned to the assignee of the present application, contain related subject matter: U.S. Ser. No. 08/903,674, filed on Jul. 31, 1997; U.S. Ser. No. 60/050,437, filed on Jun. 18, 1997; U.S. Ser. No. 08/704,852, filed on Aug. 27, 1996; U.S. Ser. No. 08/673,710, filed Jun. 19, 1996; U.S. Ser. No. 60/011,898, filed Feb. 20, 1996; U.S. Ser. No. 60/006,321, filed on Nov. 7, 1996; U.S. Ser. No. 60/006,322, filed on Nov. 7, 1996; U.S. Ser. No. 60/006,324, filed on Nov. 7, 1996; and U.S. Ser. No. 08/481,712, filed on Jun. 7, 1995. The full disclosures of each of these applications is incorporated herein by reference. Each publication cited above and herein is incorporated herein by reference in its entirety. There are a variety of materials suitable for use as bioadhesives, for tissue augmentation, for the prevention of surgical adhesions, for coating surfaces of synthetic implants, as drug delivery matrices, for ophthalmic applications, and the like. Yet in many cases the setting time for these materials can be less than optimal, whereas for surgical and other medical applications, a rapidly acting material is often preferred. In other cases, currently available materials may exhibit swelling properties that are undesirable for certain surgical applications. Thus, what is needed is a rapidly acting material, for use as, for example, a tissue sealant for hemostatic and/or wound sealing applications. It would also be desirable to provide materials that exhibit minimal swelling properties.

BRIEF SUMMARY OF THE INVENTION

The present invention provides compositions for the achievement of hemostasis or other fluid containment in an in vivo context. The compositions of the invention comprise first and second cross-linkable components and at least one hydrogel-forming component, in a composition suitable for applying to a vertebrate to facilitate fluid containment. Compositions include rapidly acting materials, for use as, for example, a tissue sealant for hemostatic and/or wound sealing applications. Compositions exhibit minimal swelling properties.

In a first aspect, embodiments of the present invention provide a composition that includes a first cross-linkable component, a second cross-linkable component that cross-links with the first cross-linkable component under reaction enabling conditions, and a hydrogel-forming component. The first and second cross-linkable component cross-link to form a porous matrix having interstices, and the hydrogel-forming component is capable of being hydrated to form a hydrogel to fill at least some of the interstices. In some aspects, the pH of the hydrogel-forming component may affect a reaction time for forming a sealant matrix barrier. For example, in some embodiments, a composition that includes a hydrogel-forming component having a pH of 6.75 provides a slower reaction time than composition that includes a hydrogel-forming component having a pH of 9.5.

The first cross-linkable component can include multiple nucleophilic groups and the second cross-linkable component can include multiple electrophilic groups. In some aspects, the first cross-linkable component includes a multi-nucleophilic polyalkylene oxide having m nucleophilic groups, and the second cross-linkable component includes a multi-electrophilic polyalkylene oxide having n electrophilic groups, where m and n are each greater than or equal to two, and wherein m+n is greater than or equal to five. In some aspects, n is two, and m is greater than or equal to three. The multi-nucleophilic polyalkylene oxide can be tetrafunctionally activated. In some aspects, m is two, and n is greater than or equal to three. The multi-electrophilic polyalkylene oxide can be tetrafunctionally activated. In some cases, both the multi-nucleophilic polyalkylene oxide and the multi-electrophilic polyalkylene oxide are tetrafunctionally activated. The multi-nucleophilic polyalkylene oxide can include two or more nucleophilic groups, for example $NH_2$, —SH, —H, —$PH_2$, and/or —CO—NH—$NH_2$. In some cases, the multi-nucleophilic polyalkylene oxide includes two or more primary amino groups. In some cases, the multi-nucleophilic polyalkylene oxide includes two or more thiol groups. The multi-nucleophilic polyalkylene oxide can be polyethylene glycol or a derivative thereof. In some cases, the polyethylene glycol includes two or more nucleophilic groups, which may include a primary amino group and/or a thiol group. The multi-electrophilic polyalkylene oxide can include two or more electrophilic groups such as —$CO_2$N($COCH_2)_2$, —$CO_2$H, —CHO, —$CHOCH_2$, —N=C=O, —$SO_2$CH=$CH_2$, —N($COCH)_2$, and/or —S—S—($C_5H_4$N). The multi-electrophilic polyalkylene oxide may include two or more succinimidyl groups. The multi-electrophilic polyalkylene oxide may include two or more maleimidyl groups. In some cases, the multi-electrophilic polyalkylene oxide can be a polyethylene glycol or a derivative thereof.

In some aspects, the composition includes a polysaccharide or a protein. The polysaccharide can be a glycosaminoglycan, such as hyaluronic acid, chitin, chondroitin sulfate A, chondroitin sulfate B, chondroitin sulfate C, keratin sulfate, keratosulfate, heparin, or a derivative thereof. The protein can be collagen or a derivative thereof. The multi-nucleophilic polyalkylene oxide or the multi-electrophilic polyalkylene oxide, or both the multi-nucleophilic polyalkylene oxide and the multi-electrophilic polyalkylene oxide, may include a linking group. In some cases, the multi-nucleophilic polyalkylene oxide can be given by the formula: polymer-$Q^1$-$X_m$. The multi-electrophilic polyalkylene oxide can be given by the formula: polymer-$Q^2$-$Y_n$. X can be a electrophilic group and Y can be a nucleophilic group, m and n can each be 2 to 4, m+n can be ≤5, and each of $Q^1$ and $Q^2$ can be linking groups such as —O—$(CH_2)_{n'}$—, —S—, —$(CH_2)_{n'}$—, —NH—$(CH_2)_{n'}$—, —$O_2$C—NH—$(CH_2)_{n'}$—, —$O_2$C—$(CH_2)_{n'}$—, —$O_2$C—$CR^1$H, and/or —O—$R^2$—CO—NH. In some cases, n' can be 1 to 10, $R^1$ can be —H, —$CH_3$, or —$C_2H_5$, $R^2$ can be —$CH_2$— or —CO—NH—$CH_2CH_2$—, and $Q^1$ and $Q^2$ can be the same or different or can be absent. In some aspects, Y can be —$CO_2$N($COCH_2)_2$ or —$CO_2$N($COCH_2)_2$. In some cases, the multi-nucleophilic polykylene oxide or the multi-electrophilic polyalkylene oxide, or both the multi-nucleophilic polyalkylene oxide and the multi-electrophilic polyalkylene oxide, further include a biodegradable group. The biodegradable group can be a lactide, glycolide, ε-caprolactone, poly(α-hydroxy acid), poly (amino acid), or a poly(anhydride). In some aspects, the hydrogel forming component is capable of being hydrated to form a fragmented biocompatible hydrogel that includes gelatin and absorbs water when delivered to a moist tissue target site. The hydrogel can include subunits having sizes ranging from about 0.01 mm to about 5 mm when fully hydrated and an equilibrium swell ranging from about 400% to about 5000%. In some cases, the hydrogel has an in vivo degradation time of less than one year. In some cases, the hydrogel is at least partially hydrated with an aqueous medium and includes an active agent, which may include a clotting agent, such as thrombin.

In another aspect, embodiments of the present invention provide a method for delivering an active agent to a patient. The method can include administering to a target site on the patient an amount of a composition as described herein. In some aspects, embodiments include a method for delivering a sealing agent to a patient. The method can include administering to a bleeding target site an amount of a composition as described herein in an amount sufficient to inhibit bleeding. In some aspects, embodiments include a method for delivering thrombin to a patient. The method can include administering to a bleeding target site an amount of a composition as described herein in an amount sufficient to inhibit bleeding.

In still another aspect, embodiments of the present invention encompass a composition that includes a multi-nucleophilic polyalkylene oxide, a multi-electrophilic polyalkylene oxide, and a hydrogel forming component. The multi-nucleophilic polyalkylene oxide further can include at least one primary amino group and at least one thiol group. Under reaction-enabling conditions the multi-nucleophilic polyalkylene oxide and multi-electrophilic polyalkylene oxide are capable of substantially immediate cross linking. Embodiments encompass compositions where the multi-nucleophilic polyalkylene oxide includes two or more thiol groups and the multi-electrophilic polyalkylene oxide includes two or more electrophilic groups such as a succinimidyl group and/or a maleimidyl group. Embodiments also encompass compositions where the multi-nucleophilic polyalkylene oxide includes two or more nucleophilic groups such as a primary amino group and/or a thiol groups. The multi-electrophilic polyalkylene oxide can include two or more succinimidyl groups. In some cases, embodiments encompass compositions that include a first polyethylene glycol having two or more thiol groups, a second polyethylene glycol having two or more succinimidyl groups or maleimidyl groups, and a hydrogel forming component. The sum of the thiol groups and the succinimidyl or maleimidyl groups may be at least five, and under reaction-enabling conditions the first polyethylene glycol and second polyethylene glycol may be capable of substantially immediate cross linking. In some cases, the first polyethylene glycol includes four thiol groups and the second polyethylene glycol includes four succinimidyl groups. In some cases, the composition includes a protein or a polysaccharide. The polysaccharide can be a glycosaminoglycan, such as hyaluronic acid, chitin, chondroitin sulfate A, chondroitin sulfate B, chondroitin sulfate C, keratin sulfate, keratosulfate, heparin, or a derivative thereof. The protein can be collagen or a derivative thereof.

In another aspect, embodiments of the present invention include a method for sealing a tissue tract. The method can include at least partly filling a tissue tract with a composition that includes a first cross-linkable component, a second cross-linkable component that cross-links with the first cross-linkable component under reaction enabling conditions, and a hydrogel-forming component. The first and second cross-linkable components can cross-link to form a porous matrix having interstices, and the hydrogel-forming component can be capable of being hydrated to form a hydrogel to fill at least some of the interstices. In some cases, the hydrogel includes subunits that have sizes ranging from about 0.05 mm to about 5 mm when fully hydrated, that have an equilibrium swell ranging from about 400% to about 1300%, and that degrade in the tissue tract after from about 1 to about 120 days. In some cases, the first cross-linkable component includes multiple nucleophilic groups and the second polymer comprises multiple electrophilic groups.

In still another aspect, embodiments of the present invention include a method for inhibiting bleeding at a target site in a patient's body. The method can include delivering a composition to the target site in an amount sufficient to inhibit bleeding, where the composition includes a first cross-linkable component, a second cross-linkable component that cross-links with the first cross-linkable component under reaction enabling conditions, and a hydrogel-forming component. The first and second cross-linkable components can cross-link to form a porous matrix having interstices, and the hydrogel forming component may be capable of being hydrated to form a hydrogel to fill at least some of the interstices. The hydrogel can include subunits that have sizes ranging from about 0.05 mm to about 5 mm when fully hydrated, that have an equilibrium swell ranging from about 400% to about 1300%, and that degrade in the tissue tract after from about 1 to about 120 days. The first cross-linkable component can include multiple nucleophilic groups and the second cross-linkable component can include multiple electrophilic groups. In another aspect, embodiments of the present invention include a method for delivering a bioactive substance to a target site in a patient's body. The method can include delivering a composition in combination with the bioactive substance to the target site, where the composition includes a first cross-linkable component, a second cross-linkable component that cross-links with the first cross-linkable component under reaction enabling conditions, and a hydrogel-forming component. The first and second cross-linkable components can cross-link to form a porous matrix having interstices, and the hydrogel forming component may be capable of being hydrated to form a hydrogel to fill at least some of the interstices. The hydrogel can have subunits having sizes ranging from about 0.05 mm to about 5 mm when fully hydrated, an equilibrium swell ranging from about 400% to about 1300%, and can degrade in the tissue tract after from about 1 to about 120 days. In some cases, the first cross-linkable component includes a multiple nucleophilic groups and the second cross-linkable component includes multiple electrophilic groups. The bioactive substance can be a hemostatic agent, such as thrombin.

In another aspect, embodiments of the present invention include a method for delivering a swellable composition to a target site in tissue. The method can include applying the composition to the target site, where the composition includes a first cross-linkable component, a second cross-linkable component that cross-links with the first cross-linkable component under reaction enabling conditions, and a hydrogel-forming component. The first and second cross-linkable components can cross-link to form a porous matrix having interstices, and the hydrogel forming component can be capable of being hydrated to form a hydrogel to fill at least some of the interstices. The hydrogel can include subunits that have sizes ranging from about 0.05 mm to about 5 mm when fully hydrated, that have an equilibrium swell ranging from about 400% to about 1300%, and that degrade in the tissue tract after from about 1 to about 120 days. The composition may be hydrated at less than its equilibrium swell upon application to the target site where it swells to an equilibrium swell value. In some aspects, the first cross-linkable component includes multiple nucleophilic groups and the second cross-linkable component includes multiple electrophilic groups. In some aspects, the target site is in tissue can be muscle, skin, epithelial tissue, smooth, skeletal or cardiac muscle, connective or supporting tissue, nerve tissue, ophthalmic and other sense organ tissue, vascular and cardiac tissue, gastrointestinal organs and tissue, pleura and other pulmonary tissue, kidney, endocrine glands, male and female reproductive organs, adipose tissue, liver, pancreas, lymph, cartilage, bone, oral tissue, and mucosal tissue, and spleen and other abdominal organs. In some aspects, the target site includes a void region within the selected tissue, such as a tissue divot, tissue tract, intravertebral space, or body cavity. In some cases, the hydrogel has a degree of hydration in the range from 50% to 95% of the hydration at equilibrium swell. In some cases the hydrogel includes a plasticizer, such as polyethylene glycol, sorbitol, or glycerol. The plasticizer may be present at from 0.1% by weight to 30% by weight of the composition of the hydrogel component. In some cases, the hydrogel includes a cross-linked protein hydrogel. The protein can include gelatin, soluble collagen, albumin, hemoglobin, fibrogen, fibrin, casein, fibronectin, elastin, keratin, laminin, and derivatives and combinations thereof. In some cases, the hydrogel includes a cross-linked polysaccharide. The polysaccharide can include glycosaminoglycans, starch derivatives, cellulose derivatives, hemicellulose derivatives, xylan, agarose, alginate, and chitosan and combinations thereof. In some cases, the hydrogel includes a cross-linked non-biologic polymer. The cross-linked non-biologic polymer can include polyacrylates, polymethacrylates, polyacrylamides, polyvinyl resins, polyactide-glycolides, polcaprolactones, polyoxyethlenes, and combinations thereof. In some cases, the hydrogel includes at least two components selected from a group that includes cross-linked proteins, cross-linked polysaccharides, and cross-linked non-biologic polymers. The hydrogel can include a hydrogel polymer and a hydrogel cross-linking agent. The hydrogel polymer and the hydrogel cross-linking agent may have been reacted under conditions which yield cross-linking of hydrogel polymer molecules. In some cases, the hydrogel includes a molecular cross linked hydrogel polymer that has been produced by irradiation of the hydrogel under conditions which yield cross-linking of hydrogel polymer molecules. In some cases, the hydrogel includes a molecular cross linked hydrogel that has been produced by reaction of monounsaturated and polyunsaturated hydrogel monomers under conditions which yield cross-linking of hydrogel polymer molecules.

In yet another aspect, embodiments of the present invention encompass a method of forming a three dimensional synthetic polymer matrix. The method includes providing a first cross-linkable component containing m nucleophilic groups and a second cross-linkable component containing n electrophilic groups. The electrophilic groups react with the nucleophilic groups to form covalent bonds therewith, m and n are each greater than or equal to two, and m+n is greater than or equal to five. The method also includes combining the first cross-linkable component and the second cross-linkable component, adding a hydrogel forming component to the first cross-linkable component and the second cross-linkable component, and allowing the first cross-linkable component and the second cross-linkable component to become cross-linked to one another to form a three dimensional matrix. The method can also include contacting a first tissue surface and a second surface with the first cross-linkable component, the second cross linkable component, and the hydrogel forming component. In some cases, the second surface is a native tissue surface. In some cases, the second surface is a non-native tissue surface, such as a synthetic implant. The synthetic implant can be a donor cornea, an artificial blood vessel, a heart valve, an artificial organ, a bond prosthesis, an implantable lenticule, a vascular graft, a stent, or a stent/graft combination. In some cases, the first cross-linkable component, the second cross-linkable component, and the hydrogel forming component are each applied in powdered form at the first tissue surface. In some cases, the first cross-linkable component, the second cross-linkable component, and the hydrogel forming component are each applied as a powder in a single combined mixed powder formulation at the first tissue surface. The mixed powder formulation can include a protein and/or a polysaccharide. The first tissue surface may be on or in a hard tissue or a soft tissue. The first tissue surface can include, surround or be adjacent to a surgical site. The method can also include closing the surgical site. In some cases, the mixed powder formulation includes collagen. In some cases, the mixed powder formulation includes a biologically active agent. In some aspects, embodiments of the present invention encompass a mixed powder composition that includes a first cross-linkable component in powdered form having multiple nucleophilic groups, a second cross-linkable component in powdered form having multiple electrophilic groups, and a hydrogel forming component in powdered form. Under reaction-enabling conditions the first and second cross-linkable components are capable of substantially immediate cross-linking.

In a related aspect, the first cross-linkable component added to the second cross-linkable component provides a combined cross-linkable component composition. The first cross-linkable component can be present at a concentration in the range of about 0.5 to about 20 percent by weight of the combined cross-linkable component composition. In some cases, the second cross-linkable component can be present at a concentration in the range of about 0.5 to about 20 percent by weight of the combined cross-linkable component composition. A weight ratio of the first cross-linkable component to the second cross-linkable component can be in the range from about 45% to about 55%. Relatedly, a weight ratio of the first cross-linkable component to the second cross-linkable component can be about 50%. In some cases, a weight ratio between the first and second cross-linkable components and the hydrogel-forming component can be within a range from about 28% to about 42% w/w. Relatedly, a weight ratio between the first and second cross-linkable components and the hydrogel-forming component can be within a range from about 20% to about 30% w/w. In some aspects, the first cross-linkable component can be present at a concentration in the range of about 0.5 to about 20 percent by weight of the combined cross-linkable component composition. Relatedly, the second cross-linkable component can be present at a concentration in the range of about 0.5 to about 20 percent by weight of the combined cross-linkable component composition. A weight ratio of the first cross-linkable component to the second cross-linkable component can be in the range from about 45% to about 55%. Similarly, a weight ratio of the first cross-linkable component to the second cross-linkable component can be about 50%.

In another aspect, embodiments of the present invention provide sealant matrix composition kits. A kit can include, for example, a container and a mixed powder composition disposed within the container. The composition can include a first cross-linkable component having multiple nucleophilic groups and a second cross-linkable component having multiple electrophilic groups. The first cross-linkable component, the second cross-linkable component, or both, may be in powdered form. The kit can also include a hydrogel forming component in powdered form. Under reaction-enabling conditions the first and second cross-linkable components may be capable of substantially immediate cross-linking. In some cases, the container includes a syringe barrel and a syringe plunger. A kit can also include written instructions for applying the mixed powder composition to a bleeding target site in a patient. In some cases, the mixed powder includes an active agent. The active agent may include thrombin. In another aspect, a kit may include a collagen sponge or other suitable support, and a mixed powder composition fixed with a surface of the sponge or support. The composition can include a first cross-linkable component having multiple nucleophilic groups and a second cross-linkable component having multiple electrophilic groups. The first cross-linkable component, the second cross-linkable component, or both, may be in powdered form. The kit can also include a hydrogel forming component in powdered form. Under reaction-enabling conditions the first and second cross-linkable components may be capable of substantially immediate cross-linking.

For a fuller understanding of the nature and advantages of the present invention, reference should be had to the ensuing detailed description taken in conjunction with the accompanying drawings.

The present invention includes but is not limited to:

A composition comprising:
a first cross-linkable component;
a second cross-linkable component that cross-links with the first cross-linkable component under reaction enabling conditions; and
a hydrogel-forming component;
wherein the first and second cross-linkable component cross-link to form a porous matrix having interstices, and wherein the hydrogel-forming component is capable of being hydrated to form a hydrogel to fill at least some of the interstices.

The composition of paragraph 31, wherein the first cross-linkable component comprises multiple nucleophilic groups and the second cross-linkable component comprises multiple electrophilic groups.

The composition of paragraph 31, wherein the first cross-linkable component comprises a multi-nucleophilic polyalkylene oxide having m nucleophilic groups, and the second cross-linkable component comprises a multi-electrophilic polyalkylene oxide having n electrophilic groups, wherein m and n are each greater than or equal to two, and wherein m+n is greater than or equal to five.

The composition of paragraph 33, wherein n is two, and wherein m is greater than or equal to three.

The composition of paragraph 34, wherein the multi-nucleophilic polyalkylene oxide is tetrafunctionally activated.

The composition of paragraph 33, wherein m is two, and wherein n is greater than or equal to three.

The composition of paragraph 36, wherein the multi-electrophilic polyalkylene oxide is tetrafunctionally activated.

The composition of paragraph 33, wherein both the multi-nucleophilic polyalkylene oxide and the multi-electrophilic polyalkylene oxide are tetrafunctionally activated.

The composition of paragraph 33, wherein the multi-nucleophilic polyalkylene oxide further comprises two or more nucleophilic groups selected from the group consisting of $-NH_2$, $-SH$, $-H$, $-PH_2$, and $-CO-NH-NH_2$.

The composition of paragraph 33, wherein the multi-nucleophilic polyalkylene oxide further comprises two or more primary amino groups.

The composition of paragraph 33, wherein the multi-nucleophilic polyalkylene oxide further comprises two or more thiol groups.

The composition of paragraph 33, wherein the multi-nucleophilic polyalkylene oxide is polyethylene glycol or a derivative thereof.

The composition of paragraph 42, wherein the polyethylene glycol further comprises two or more nucleophilic groups selected from the group consisting of a primary amino group and a thiol group.

The composition of paragraph 33, wherein the multi-electrophilic polyalkylene oxide further comprises two or more electrophilic groups selected from the group consisting of $CO_2N(COCH_2)_2$, $-CO_2H$, $-CHO$, $-CHOCH_2$, $-N=C=O$, $-SO_2CH=CH_2$, $N(COCH)_2$, and $-S-S-(C_5H_4N)$.

The composition of paragraph 33, wherein the multi-electrophilic polyalkylene oxide further comprises two or more succinimidyl groups.

The composition of paragraph 33, wherein the multi-electrophilic polyalkylene oxide further comprises two or more maleimidyl groups.

The composition of paragraph 33, wherein the multi-electrophilic polyalkylene oxide is a polyethylene glycol or a derivative thereof.

The composition of paragraph 33 further comprising a polysaccharide or a protein.

The composition of paragraph 33 further comprising a polysaccharide, wherein the polysaccharide is a glycosaminoglycan.

The composition of paragraph 49, wherein the glycosaminoglycan is selected from the group consisting of hyaluronic acid, chitin, chondroitin sulfate A, chondroitin sulfate B, chondroitin sulfate C, keratin sulfate, keratosulfate, heparin, and derivatives thereof.

The composition of paragraph 33 further comprising a protein, wherein the protein is collagen or a derivative thereof.

The composition of paragraph 33, wherein the multi-nucleophilic polyalkylene oxide or the multi-electrophilic polyalkylene oxide, or both the multi-nucleophilic polyalkylene oxide and the multi-electrophilic polyalkylene oxide, further comprise(s) a linking group.

The composition of paragraph 33, wherein the multi-nucleophilic polyalkylene oxide is given by the formula:

$$\text{polymer-}Q^1\text{-}X_m$$

and wherein the multi-electrophilic polyalkylene oxide is given by the formula:

$$\text{polymer-}Q^2\text{-}Y_n$$

wherein X is an electrophilic group and Y is a nucleophilic group;
wherein m and n are each 2 to 4;
wherein m+n≤5;
wherein each of $Q^1$ and $Q^2$ are linking groups selected from the group consisting of $-O-(CH_2)_{n'}-$, $-S-$, $-(CH_2)_{n'}-$, $-NH-(CH_2)_{n'}-$, $-O_2C-NH-(CH_2)_{n'}-$, $-O_2C-(CH_2)_{n'}-$, $-O_2C-CR^1H$, and $-O-R^2-CO-NH$;
wherein n'=1 to 10;
wherein $R^1=-H$, $-CH_3$, or $-C_2H_5$;
wherein $R^2=-CH_2-$ or $-CO-NH-CH_2CH_2-$; and
wherein $Q^1$ and $Q^2$ may be the same or different or may be absent.

The composition of paragraph 53, wherein Y is given by the formula:

$$-CO_2N(COCH_2)_2.$$

The composition of paragraph 53, wherein Y is given by the formula:

$$-N(COCH)_2.$$

The composition of paragraph 33, wherein the multi-nucleophilic polykylene oxide or the multi-electrophilic polyalkylene oxide or both the multi-nucleophilic polyalkylene oxide and the multi-electrophilic polyalkylene oxide further comprise(s) a biodegradable group.

The composition of paragraph 56, wherein the biodegradable group is selected from the group consisting of lactide, glycolide, ε-caprolactone, poly(α-hydroxy acid), poly(amino acid), and poly(anhydride).

The composition of paragraph 31, wherein the hydrogel forming component is capable of being hydrated to form a fragmented biocompatible hydrogel that comprises gelatin and will absorb water when delivered to a moist tissue target site, and wherein the hydrogel comprises subunits having sizes ranging from about 0.01 mm to about 5 mm when fully hydrated and has an equilibrium swell ranging from about 400% to about 5000%.

The composition of paragraph 58, wherein the hydrogel has an in vivo degradation time of less than one year.

The composition of any of paragraphs 58 and 59, wherein the hydrogel is at least partially hydrated with an aqueous medium comprising an active agent.

The composition of paragraph 60, wherein the active agent is a clotting agent.

The composition of paragraph 61, wherein the clotting agent is thrombin.

A method for delivering an active agent to a patient, the method comprising administering to a target site on the patient an amount of the composition of paragraph 60.

A method for delivering a sealing agent to a patient, the method comprising administering to a bleeding target site an amount of the composition of paragraph 31 sufficient to inhibit bleeding.

A method for delivering thrombin to a patient, the method comprising administering to a bleeding target site an amount of the composition of paragraph 62 sufficient to inhibit bleeding.

A composition comprising a multi-nucleophilic polyalkylene oxide, a multi-electrophilic polyalkylene oxide, and a hydrogel forming component, wherein the multi-nucleophilic polyalkylene oxide further comprises at least one primary amino group and at least one thiol group, and wherein under reaction-enabling conditions the multi-nucleophilic polyalkylene oxide and multi-electrophilic polyalkylene oxide are capable of substantially immediate cross linking.

A composition comprising a multi-nucleophilic polyalkylene oxide, a multi-electrophilic polyalkylene oxide, and a hydrogel forming component, wherein the multi-nucleophilic polyalkylene oxide further comprises two or more thiol groups and the multi-electrophilic polyalkylene oxide further comprises two or more electrophilic groups selected from the group consisting of succinimidyl groups and maleimidyl groups, and wherein under reaction-enabling conditions the multi-nucleophilic polyalkylene oxide and multi-electrophilic polyalkylene oxide are capable of substantially immediate cross linking.

A composition comprising a multi-nucleophilic polyalkylene oxide, a multi-electrophilic polyalkylene oxide, and a hydrogel forming component, wherein the multi-nucleophilic polyalkylene oxide further comprises two or more nucleophilic groups selected from the group consisting of primary amino groups and thiol groups, and the multi-electrophilic polyalkylene oxide further comprises two or more succinimidyl groups, and wherein under reaction-enabling conditions the multi-nucleophilic polyalkylene oxide and multi-electrophilic polyalkylene oxide are capable of substantially immediate cross linking.

A composition comprising a first polyethylene glycol comprising two or more thiol groups, a second polyethylene glycol comprising two or more succinimidyl groups or maleimidyl groups, and a hydrogel forming component, wherein the sum of the thiol groups and the succinimidyl or maleimidyl groups is at least five, and wherein under reaction-enabling conditions the first polyethylene glycol and second polyethylene glycol are capable of substantially immediate cross linking.

The composition of paragraph 69, wherein the first polyethylene glycol further comprises four thiol groups and the second polyethylene glycol further comprises four succinimidyl groups.

The composition of paragraph 69 further comprising a protein or a polysaccharide.

The composition of paragraph 69 further comprising a polysaccharide, wherein the polysaccharide is a glycosaminoglycan.

The composition of paragraph 72, wherein the glycosaminoglycan is selected from the group consisting of hyaluronic acid, chitin, chondroitin sulfate A, chondroitin sulfate B, chondroitin sulfate C, keratin sulfate, keratosulfate, heparin, and derivatives thereof.

The composition of paragraph 69 further comprising a protein, wherein the protein is collagen or a derivative thereof.

A method for sealing a tissue tract, the method comprising at least partly filling a tissue tract with a composition comprising:
  a first cross-linkable component;
  a second cross-linkable component that cross-links with the first cross-linkable component under reaction enabling conditions; and
  a hydrogel-forming component;
  wherein the first and second cross-linkable components cross-link to form a porous matrix having interstices, and the hydrogel-forming component is capable of being hydrated to form a hydrogel to fill at least some of the interstices, the hydrogel comprising subunits having sizes ranging from about 0.05 mm to about 5 mm when fully hydrated, having an equilibrium swell ranging from about 400% to about 1300%, and degrading in the tissue tract after from about 1 to about 120 days.

The method of paragraph 75, wherein the first cross-linkable component comprises multiple nucleophilic groups and the second polymer comprises multiple electrophilic groups.

A method for inhibiting bleeding at a target site in a patient's body, the method comprising delivering a composition to the target site in an amount sufficient to inhibit bleeding, the composition comprising:
  a first cross-linkable component;
  a second cross-linkable component that cross-links with the first cross-linkable component under reaction enabling conditions; and
  a hydrogel-forming component;
  wherein the first and second cross-linkable components cross-link to form a porous matrix having interstices, and the hydrogel forming component is capable of being hydrated to form a hydrogel to fill at least some of the interstices, the hydrogel comprising subunits having sizes ranging from about 0.05 mm to about 5 mm when fully hydrated, having an equilibrium swell ranging from about 400% to about 1300%, and degrading in the tissue tract after from about 1 to about 120 days.

The method of paragraph 77, wherein the first cross-linkable component comprises multiple nucleophilic groups and the second cross-linkable component comprises multiple electrophilic groups.

A method for delivering a bioactive substance to a target site in a patient's body, the method comprising delivering a composition in combination with the bioactive substance to the target site, the composition comprising:
  a first cross-linkable component;
  a second cross-linkable component that cross-links with the first cross-linkable component under reaction enabling conditions; and
  a hydrogel-forming component;
  wherein the first and second cross-linkable components cross-link to form a porous matrix having interstices, and the hydrogel forming component is capable of being hydrated to form a hydrogel to fill at least some of the interstices, the hydrogel comprising subunits having sizes ranging from about 0.05 mm to about 5 mm when fully hydrated, having an equilibrium swell ranging from about 400% to about 1300%, and degrading in the tissue tract after from about 1 to about 120 days.

The method of paragraph 79, wherein the first cross-linkable component comprises multiple nucleophilic groups and the second cross-linkable component comprises multiple electrophilic groups.

A method as in paragraph 79, wherein the bioactive substance is a hemostatic agent.

A method as in paragraph 79, wherein the bioactive substance is thrombin.

A method for delivering a swellable composition to a target site in tissue, said method comprising applying the composition to the target site, the composition comprising:
  a first cross-linkable component;
  a second cross-linkable component that cross-links with the first cross-linkable component under reaction enabling conditions; and
  a hydrogel-forming component;
  wherein the first and second cross-linkable components cross-link to form a porous matrix having interstices, and the hydrogel forming component is capable of being hydrated to form a hydrogel to fill at least some of the interstices, the hydrogel comprising subunits having sizes ranging from about 0.05 mm to about 5 mm when fully hydrated, having an equilibrium swell ranging from about 400% to about 1300%, and degrading in the tissue tract after from about 1 to about 120 days, the composition being hydrated at less than its equilibrium swell upon application to the target site where it swells to an equilibrium swell value.

The method of paragraph 83, wherein the first cross-linkable component comprises multiple nucleophilic groups and the second cross-linkable component comprises multiple electrophilic groups.

The method of paragraph 83, wherein the target site is in tissue selected from the group consisting of muscle, skin, epithelial tissue, connective or supporting tissue, nerve tissue, ophthalmic and other sense organ tissue, vascular and cardiac tissue, gastrointestinal organs and tissue, pleura and other pulmonary tissue, kidney, endocrine glands, male and female reproductive organs, adipose tissue, liver, pancreas, lymph, cartilage, bone, oral tissue, and mucosal tissue, and spleen and other abdominal organs.

The method of paragraph 85, wherein the target site is a void region within the selected tissue.

The method of paragraph 86, wherein the void region is selected from the group consisting of tissue divots, tissue tracts, intravertebral spaces, and body cavities.

The method of paragraph 83, wherein the hydrogel has a degree of hydration in the range from 50% to 95% of the hydration at equilibrium swell.

The method of paragraph 83, wherein the hydrogel comprises a plasticizer.

The method of paragraph 89, wherein the plasticizer is selected from the group consisting of polyethylene glycol, sorbitol, and glycerol.

The method of paragraph 89, wherein the plasticizer is present at from 0.1% by weight to 30% by weight of the composition of the hydrogel component.

A method as in any one of paragraphs 75-91, wherein the hydrogel comprises a cross-linked protein hydrogel.

A method as in paragraph 92, wherein the protein is selected from the group consisting of gelatin, soluble collagen, albumin, hemoglobin, fibrogen, fibrin, casein, fibronectin, elastin, keratin, laminin, and derivatives and combinations thereof.

A method as in any one of paragraphs 75-91, wherein the hydrogel comprises a cross-linked polysaccharide.

A method as in paragraph 94, wherein the polysaccharide is selected from the group consisting of glycosaminoglycans, starch derivatives, cellulose derivatives, hemicellulose derivatives, xylan, agarose, alginate, and chitosan and combinations thereof.

A method as in any one of paragraphs 75-91, wherein the hydrogel comprises a cross-linked non-biologic polymer.

A method as in paragraph 96, wherein the cross-linked non-biologic polymer selected from the group consisting of polyacrylates, polymethacrylates, polyacrylamides, polyvinyl resins, polyactide-glycolides, polcaprolactones, polyoxyethylenes, and combinations thereof.

A method as in any one of paragraphs 75-91, wherein the hydrogel comprises at least two components selected from the group consisting of cross-linked proteins, cross-linked polysaccharides, and cross-linked non-biologic polymers.

A method as in any one of paragraphs 75-91, wherein the hydrogel comprises a hydrogel polymer and a hydrogel cross-linking agent, wherein the hydrogel polymer and hydrogel cross-linking agent have been reacted under conditions which yield cross-linking of hydrogel polymer molecules.

A method as in any one of paragraphs 75-91, wherein the hydrogel comprises a molecular cross linked hydrogel polymer that has been produced by irradiation of the hydrogel under conditions which yield cross-linking of hydrogel polymer molecules.

A method as in any one of paragraphs 75-91, wherein the hydrogel comprises a molecular cross linked hydrogel that has been produced by reaction of monounsaturated and polyunsaturated hydrogel monomers under conditions which yield cross-linking of hydrogel polymer molecules.

A method of forming a three dimensional synthetic polymer matrix comprising the steps of:
  providing a first cross-linkable component containing m nucleophilic groups and a second cross-linkable component containing n electrophilic groups, wherein the electrophilic groups react with the nucleophilic groups to form covalent bonds therewith, wherein m and n are each greater than or equal to two, and wherein m+n is greater than or equal to five;
  combining the first cross-linkable component and the second cross-linkable component;
  adding a hydrogel forming component to the first cross-linkable component and the second cross-linkable component;
  allowing the first cross-linkable component and the second cross-linkable component to become cross-linked to one another to form a three dimensional matrix.

The method of paragraph 102, further comprising contacting a first tissue surface and a second surface with the first cross-linkable component, the second cross linkable component, and the hydrogel forming component.

The method of paragraph 103, wherein the second surface is a native tissue surface.

The method of paragraph 103, wherein the second surface is a non-native tissue surface.

The method of paragraph 105, wherein the non-native tissue surface is a synthetic implant.

The method of paragraph 106, wherein the synthetic implant is selected from the group consisting of a donor cornea, an artificial blood vessel, a heart valve, an artificial organ, a bond prosthesis, an implantable lenticule, a vascular graft, a stent, and a stent/graft combination.

The method of paragraph 102, wherein the first cross-linkable component, the second cross-linkable component, and the hydrogel forming component are each applied in powdered form at the first tissue surface.

The method of paragraph 102, wherein the first cross-linkable component, the second cross-linkable component, and the hydrogel forming component are each applied as a powder in a single combined mixed powder formulation at the first tissue surface.

The method of paragraph 109, wherein the mixed powder formulation further comprises a protein or a polysaccharide.

The method of paragraph 102, wherein the first tissue surface is on or in a hard tissue or a soft tissue.

The method of paragraph 102, wherein the first tissue surface comprises, surrounds or is adjacent to a surgical site, and wherein the method further comprises the step of closing the surgical site.

The method of paragraph 102, wherein the mixed powder formulation further comprises collagen.

The method of paragraph 102, wherein the mixed powder formulation further comprises a biologically active agent.

A mixed powder composition comprising:
  a first cross-linkable component comprising multiple nucleophilic groups, the first cross-linkable component in powdered form;
  a second cross-linkable component comprising multiple electrophilic groups, the second cross-linkable component in powdered form; and
  a hydrogel forming component in powdered form;
  wherein under reaction-enabling conditions the first and second cross-linkable components are capable of substantially immediate cross-linking.

The mixed powder composition of paragraph 115, wherein the first cross-linkable component added to the second cross-linkable component provides a combined cross-linkable component composition, and the first cross-linkable component is present at a concentration in the range of about 0.5 to about 20 percent by weight of the combined cross-linkable component composition.

The mixed powder composition of paragraph 115, wherein the first cross-linkable component added to the second cross-linkable component provides a combined cross-linkable component composition, and the second cross-linkable component is present at a concentration in the range of about 0.5 to about 20 percent by weight of the combined cross-linkable component composition.

The mixed powder composition of paragraph 115, wherein a weight ratio of the first cross-linkable component to the second cross-linkable component is in the range from about 45% to about 55%.

The mixed powder composition of paragraph 115, wherein a weight ratio of the first cross-linkable component to the second cross-linkable component is about 50%.

The mixed powder composition of paragraph 115, wherein a weight ratio between the first and second cross-linkable components and the hydrogel-forming component is within a range from about 28% to about 42% w/w.

The mixed powder composition of paragraph 115, wherein a weight ratio between the first and second cross-linkable components and the hydrogel-forming component is within a range from about 20% to about 30% w/w.

The mixed powder composition of paragraph 121, wherein the first cross-linkable component added to the second cross-linkable component provides a combined cross-linkable component composition, and the first cross-linkable component is present at a concentration in the range of about 0.5 to about 20 percent by weight of the combined cross-linkable component composition.

The mixed powder composition of paragraph 121, wherein the first cross-linkable component added to the second cross-linkable component provides a combined cross-linkable component composition, and the second cross-linkable component is present at a concentration in the range of about 0.5 to about 20 percent by weight of the combined cross-linkable component composition.

The mixed powder composition of paragraph 121, wherein a weight ratio of the first cross-linkable component to the second cross-linkable component is in the range from about 45% to about 55%.

The mixed powder composition of paragraph 121, wherein a weight ratio of the first cross-linkable component to the second cross-linkable component is about 50%.

A kit comprising:
  a container; and
  a mixed powder composition disposed within the container, the composition comprising:
    a first cross-linkable component comprising multiple nucleophilic groups, the first cross-linkable component in powdered form;
    a second cross-linkable component comprising multiple electrophilic groups, the second cross-linkable component in powdered form; and
    a hydrogel forming component in powdered form;
    wherein under reaction-enabling conditions the first and second cross-linkable components are capable of substantially immediate cross-linking.

The kit of paragraph 126, wherein the container comprises a syringe barrel and a syringe plunger.

The kit of paragraph 126, further comprising written instructions for applying the mixed powder composition to a bleeding target site in a patient.

The kit of paragraph 126, wherein the mixed powder further comprises an active agent.

The kit of paragraph 129, wherein the active agent comprises thrombin.

A kit comprising:
  a collagen sponge; and
  a mixed powder composition fixed with a surface of the sponge, the mixed powder composition comprising:
    a first cross-linkable component comprising multiple nucleophilic groups, the first cross-linkable component in powdered form;
    a second cross-linkable component comprising multiple electrophilic groups, the second cross-linkable component in powdered form; and
    a hydrogel forming component in powdered form;
    wherein under reaction-enabling conditions the first and second cross-linkable components are capable of substantially immediate cross-linking.

A composition for the manufacture of a medicament comprising:
  a first cross-linkable component;
  a second cross-linkable component that cross-links with the first cross-linkable component under reaction enabling conditions; and
  a hydrogel-forming component;
  wherein the first and second cross-linkable component cross-link to form a porous matrix having interstices, and wherein the hydrogel-forming component is capable of being hydrated to form a hydrogel to fill at least some of the interstices.

The composition of paragraph 132, wherein the first cross-linkable component comprises multiple nucleophilic groups and the second cross-linkable component comprises multiple electrophilic groups.

The composition of paragraph 133, wherein the first cross-linkable component comprises a multi-nucleophilic polyalkylene oxide having m nucleophilic groups, and the second cross-linkable component comprises a multi-electrophilic polyalkylene oxide having n electrophilic groups, wherein m and n are each greater than or equal to two, and wherein m+n is greater than or equal to five.

The composition of paragraph 134, wherein n is two, and wherein m is greater than or equal to three.

The composition of paragraph 135, wherein the multi-nucleophilic polyalkylene oxide is tetrafunctionally activated.

The composition of paragraph 134, wherein m is two, and wherein n is greater than or equal to three.

The composition of paragraph 137, wherein the multi-electrophilic polyalkylene oxide is tetrafunctionally activated.

The composition of paragraph 134, wherein both the multi-nucleophilic polyalkylene oxide and the multi-electrophilic polyalkylene oxide are tetrafunctionally activated.

The composition of paragraph 134, wherein the multi-nucleophilic polyalkylene oxide further comprises two or more nucleophilic groups selected from the group consisting of $NH_2$, —SH, —H, —$PH_2$, and —CO—NH—$NH_2$.

The composition of paragraph 134, wherein the multi-nucleophilic polyalkylene oxide further comprises two or more primary amino groups.

A composition comprising:
a collagen sponge comprising native collagen fibers; and
a mixed powder composition fixed with a surface of the sponge, the mixed powder composition comprising:
a first cross-linkable component comprising multiple nucleophilic groups, the first cross-linkable component in powdered form and comprising about 10% of the mixed powder;
a second cross-linkable component comprising multiple electrophilic groups, the second cross-linkable component in powdered form and comprising about 10% of the mixed powder; and
a hydrogel forming component in powdered form, comprising about 80% of the mixed powder;
wherein under reaction-enabling conditions the first and second cross-linkable components are capable of substantially immediate cross-linking to form a porous matrix having interstices, and the hydrogel-forming component is capable of being hydrated to form a hydrogel to fill at least some of the interstices.

BRIEF DESCRIPTION OF THE DRAWINGS

FIG. 12 illustrates the effect of PEG concentration on swelling ratio, according to embodiments of the present invention.

FIG. 13 illustrates the effect of PEG concentration on swelling ratio, according to embodiments of the present invention.

DETAILED DESCRIPTION OF THE INVENTION

Figure 1:
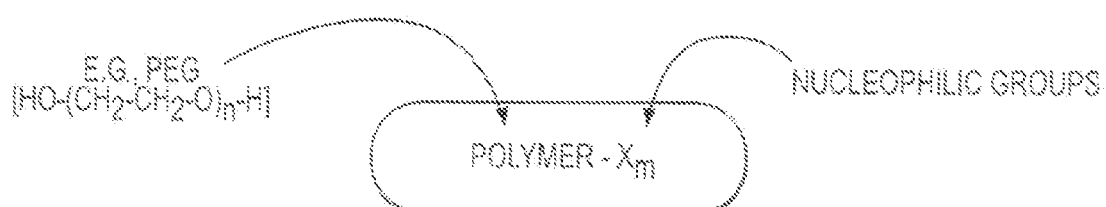
FIG. 1 illustrates a first cross-linkable component according to some embodiments of the present invention.

According to some embodiments, the present invention provides dry sealant matrix compositions for the achievement of hemostasis or other fluid containment in an in vivo context by sealing a tissue breach or defect. The compositions of some embodiments of the invention comprise first and second cross-linkable components and at least one hydrogel-forming component, in a dry composition suitable for applying to a tissue of a vertebrate to facilitate fluid containment. The first and second components in the compositions of the invention react under in-vivo conditions to form a cross-linked matrix, while the hydrogel-forming component rapidly absorbs the biological fluid coming through the tissue breach, as well as strengthening the resultant physical sealant matrix barrier formed as the first and second components cross-link. As described in this application, "sealant matrix compositions" may refer to compositions of the invention before application to the tissue site in vivo, and "sealant matrix barrier" may refer to the resulting matrix barrier after the compositions of the invention contact biological fluids and the first and second components cross-link to form a porous cross-linked matrix containing the hydrogel. Sealant matrix compositions may be produced in a variety of formats, including powders, cakes, pads, and the like. Cake embodiments include sealant matrix composition powder samples that have been heated or baked to form an aggregate body. Pad embodiments include sealant matrix composition powder samples that have been placed on a sponge such as a collagen sponge or other support, which is then baked to created a solidified powder that is fused to the sponge or support.

Although the present invention may be used to contain non-blood biological fluids (e.g., lymph or spinal fluid), the sealant matrix formed by the compositions of some embodiments of the present invention may also be called a "hemostatic matrix," as this is a primary use described herein.

In addition to providing rapid hemostasis and a barrier with high adherence to surrounding tissues, the sealant matrix of some embodiments of the present invention has several advantages over previously disclosed materials used to achieve hemostasis. First, the sealant matrix of some embodiments of the present invention may be used under conditions where the tissue breach is quite wet (e.g., rapidly oozing or spurting arterial bleeds, such as abrasive or sharp trauma to an internal organ). In comparison, many compositions currently marketed for hemostasis require a relatively dry site for proper adherence of the composition and the maintenance of hemostasis. For example, in some cases certain PEG mixtures may be placed in a rapidly bleeding site, however it is likely that they could be washed away. Similarly, in some cases certain gelatin compositions could hydrate in a rapidly bleeding site, however it is likely that they could have difficulty remaining at the site. Advantageously, it has been discovered that preparations which include a first cross-linkable component, a second cross-linkable component, and a hydrogel-forming component can provide a material that in reaction enabling conditions remains immobilized even with substantial bleeding to form a mechanically stable clot-like material to staunch the bleeding. Second, the sealant matrix of some embodiments of the present invention functions by physically sealing the tissue breach, without reliance on any endogenous clotting capacity of the vertebrate. Thus, the sealant matrix can be utilized on vertebrates with low fibrinogen concentration in their blood, or even with blood substitutes that contain no fibrinogen. For example, when first and second cross-linkable components are combined with a hydrogel forming component and applied to a bleeding surface, a synergistic interaction between the cross-linkable components and the hydrogel forming component can occur. According to some embodiments, the first and second cross-linkable components can, in the presence of they hydrogel forming component, react and cross-link at the bleeding target site to form a relatively rigid framework. Relatedly, the hydrogel forming component can fill in the relatively rigid framework and mediate the formation of a physical seal.

In accordance with some embodiments of the present invention, sealant matrix compositions can be prepared mixing a first cross-linkable component with a second cross-linkable component and a hydrogel-forming component under conditions in which the first and second cross-linkable components do not cross-link (i.e., lack of moisture, proper pH, temperature, etc.). Upon contact with the biological fluid, or in other reaction enabling conditions, the cross-linkable first and second components cross-link to form a porous matrix having interstices, and the hydrogel-forming component is hydrated to form a hydrogel filling at least some of the interstices. Optionally, the cross-linkable components may also cross-link with the hydrogel-forming component and/or surrounding tissues.

I. SEALANT MATRIX CROSS-LINKABLE COMPONENTS

Often, the first cross-linkable component contains two or more nucleophilic groups and the second cross-linkable component contains two or more electrophilic groups capable of covalently binding with the nucleophilic groups on the first cross-linkable component. The first and second components can cross-link to form a porous matrix. Exemplary first and second components and porous matrices are described in U.S. Pat. Nos. 5,874,500; 6,166,130; 6,312,725; 6,328,229; and 6,458,889; the contents of which are hereby incorporated by reference.

The first and second components are typically selected to be non-immunogenic and, as such, may not require a "skin test" prior to starting treatment. Further, these components and the hydrogel-forming component may be selected to resist enzymatic cleavage by matrix metalloproteinases (e.g., collagenase) to provide greater long-term persistence in vivo than currently available collagen compositions. Alternatively, the first and second components and the hydrogel-forming components may be selected to be eliminated or resorbed during wound healing in order to avoid the formation of fibrous tissue around the sealant matrix in vivo.

In one embodiment, the first component may be a synthetic polymer containing multiple nucleophilic groups (represented below as "X") which can react with a second component synthetic polymer containing multiple electrophilic groups (represented below as "Y"), resulting in a covalently bound polymer network, as follows:

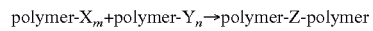

wherein
$m \geq 2$, $n \geq 2$, and $m+n \geq 5$;
$X = -NH_2$, $-SH$, $-OH$, $-PH_2$, $-CO-NH-NH_2$, etc., and can be the same or different;
$Y = -CO_2N(COCH_2)_2$, $-CO_2H$, $-CHO$, $-CHOCH_2$, $-N=C=O$, $SO_2$ $CH=CH_2$, $-N(COCH)_2$, $-S-S-(C_5H_4N)$, etc., and can be the same or different; and
$Z$ = functional group resulting from the union of a nucleophilic group (X) and an electrophilic group (Y).

Figure 2:
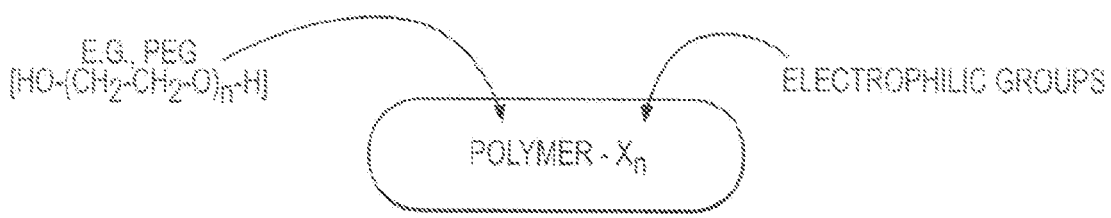
FIG. 2 illustrates a second cross-linkable component according to some embodiments of the present invention.

As noted above, X and Y may be the same or different, i.e., the first component may have two different nucleophilic groups and/or the second component may have two different electrophilic groups. An exemplary first component polymer or first cross-linkable component is illustrated in FIG. 1. An exemplary second component polymer or second cross-linkable component is illustrated in FIG. 2.

The backbone of the first and second component polymers can be an alkylene oxide, particularly, ethylene oxide, propylene oxide, and mixtures thereof. Examples of difunctional alkylene oxides can be represented by:

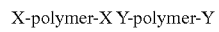

wherein X and Y are as defined above, and the term "polymer" represents $-(CH_2CH_2O)_n-$ or $-(CH(CH_3)CH_2O)_n-$ or $-(CH_2CH_2O)_n-(CH(CH_3)CH_2O)_n-$.

The functional group X or Y is commonly coupled to the polymer backbone by a linking group (represented below as "Q"), many of which are known or possible. Although the components of the invention have two or more functional groups, the examples below show only one functional group and the resulting cross-linking for the sake of simplicity. There are many ways to prepare the various functionalized polymers, some of which are listed below:

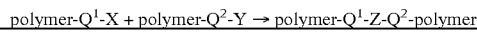

| wherein Q = | whole structure = |
|---|---|
| $-O-(CH_2)_n-$ | polymer-$O-(CH_2)_n-X$ (or Y) |
| $-S-(CH_2)_n-$ | polymer-$S-(CH_2)_n-X$ (or Y) |
| $-NH-(CH_2)_n-$ | polymer-$NH-(CH_2)_n-X$ (or Y) |
| $-O_2C-NH-(CH_2)_n-$ | polymer-O $O_2C-NH-(CH_2)_n-X$ (or Y) |
| $-O_2C-(CH_2)_n-$ | polymer-$O_2C-(CH_2)_n-X$ (or Y) |
| $-O_2C-CR^1H-$ | polymer-$O_2C-CRH-X$ (or Y) |
| $-O-R^2-CO-NH-$ | polymer-$O-R-CO-NH-X$ (or Y) | wherein
$n = 1\text{-}10$ in each case;
$R^1 = H$, $CH_3$, $C_2H_5$, $\ldots$ $C_pH_{2p+1}$;
$R^2 = CH_2$, $CO-NH-CH_2CH_2$.
$Q^1$ and $Q^2$ may be the same or different.
For example, when $Q^2 = OCH_2CH_2$ (there is no $Q_1$ in this case); $Y = -CO_2N(COCH_2)_2$; and $X = -NH_2$, $-SH$, or $-OH$, the resulting reactions and Z groups would be as follows:

polymer-NH₂+polymer-OCH₂CH₂CO₂—
   N(COCH₂)₂→—NH—OCH₂CH₂CO-polymer
   (amide)

polymer-SH+polymer-OCH₂CH₂CO₂—
   N(COCH₂)₂→—S—OCH₂CH₂CO-polymer
   (thioester)

polymer-OH+polymer-OCH₂CH₂CO₂—
   N(COCH₂)₂→—O—OCH₂CH₂CO-polymer
   (ester)

An additional group, represented below as "D", can be inserted between the polymer and the linking group to increase degradation of the crosslinked polymer composition in vivo, for example, for use in drug delivery applications:

polymer-D-Q-X+polymer-D-Q-Y→polymer-D-Q-Z-Q-D-polymer-

Some useful biodegradable groups "D" include lactide, glycolide, ε-caprolactone, poly(α-hydroxy acid), poly(amino acids), poly(anhydride), and various di- or tripeptides.

A. First and Second Components with Polymer Backbones

As noted above, in order to prepare the compositions of the present invention, it is useful to provide a first component polymer containing two or more nucleophilic groups, such as primary amino groups or thiol groups, and a second component polymer containing two or more electrophilic groups capable of covalently binding with the nucleophilic groups on the first component polymer. The first and second component polymers can be synthetic.

As used with respect to first and second component polymers, the term "polymer" refers inter alia to polyalkyls; di-, tri-, oligo-, and polyamino acids; and tri-, oligo-, or polysaccharides.

As used with respect to first and second component polymers, the term "synthetic polymer" encompasses polymers that are not naturally occurring and that are produced via chemical synthesis. As such, naturally occurring proteins such as collagen and naturally occurring polysaccharides such as hyaluronic acid may be excluded. Synthetic collagen, and synthetic hyaluronic acid, and their derivatives, are included. Synthetic polymers containing either nucleophilic or electrophilic groups encompass "multifunctionally activated synthetic polymers". The term "multifunctionally activated" (or, simply, "activated") can refer to synthetic polymers which have, or have been chemically modified to have, two or more nucleophilic or electrophilic groups which are capable of reacting with one another (i.e., the nucleophilic groups react with the electrophilic groups) to form covalent bonds. Types of multifunctionally activated synthetic polymers include difunctionally activated, tetrafunctionally activated, and star-branched polymers.

Multifunctionally activated synthetic polymers for use in the present invention often contain at least two, or at least three, functional groups in order to form a three-dimensional crosslinked network with synthetic polymers containing multiple nucleophilic groups (i.e., "multi-nucleophilic polymers"). In other words, they are typically at least difunctionally activated, or trifunctionally or tetrafunctionally activated. If the first synthetic polymer is a difunctionally activated synthetic polymer, the second synthetic polymer typically contains three or more functional groups in order to obtain a three-dimensional crosslinked network. Both the first and the second component polymer may contain at least three functional groups.

B. First Component Polymer

First component polymers containing multiple nucleophilic groups are also referred to generically herein as "multi-nucleophilic polymers". For use in the present invention, multi-nucleophilic polymers often contain at least two, or at least three, nucleophilic groups. If a synthetic polymer containing only two nucleophilic groups is used, a synthetic polymer containing three or more electrophilic groups will often be used in order to obtain a three-dimensional crosslinked network.

Multi-nucleophilic polymers for use in the compositions and methods of the present invention include synthetic polymers that contain, or have been modified to contain, multiple nucleophilic groups such as primary amino groups and thiol groups. Such multi-nucleophilic polymers can include: (i) synthetic polypeptides that have been synthesized to contain two or more primary amino groups or thiol groups; and (ii) polyethylene glycols that have been modified to contain two or more primary amino groups or thiol groups. In general, reaction of a thiol group with an electrophilic group tends to proceed more slowly than reaction of a primary amino group with an electrophilic group.

Multi-nucleophilic polypeptides can be synthetic polypeptides that have been synthesized to incorporate amino acids containing primary amino groups (such as lysine) and/or amino acids containing thiol groups (such as cysteine). For instance, the first component polymer can be a dilysine, trilysine, quatralysine, pentalysine, or a dicysteine, tricysteine, quatracysteine, pentacystein, or oligopeptides or polypeptides comprising two or more lysines or cysteines and other amino acids (e.g., glycine, alanine,), preferably non-hydrophobic amino acids. Poly(lysine), a synthetically produced polymer of the amino acid lysine (145 MW), is often used. Poly(lysine)s have been prepared having anywhere from 6 to about 4,000 primary amino groups, corresponding to molecular weights of about 870 to about 580,000. Poly(lysine)s of varying molecular weights are commercially available from Peninsula Laboratories, Inc. (Belmont, Calif.).

Polyethylene glycol can be chemically modified to contain multiple primary amino or thiol groups according to methods set forth, for example, in Chapter 22 of Poly(ethylene Glycol) Chemistry: Biotechnical and Biomedical Applications, J. Milton Harris, ed., Plenum Press, N.Y. (1992). Polyethylene glycols which have been modified to contain two or more primary amino groups are referred to herein as "multi-amino PEGs". Polyethylene glycols which have been modified to contain two or more thiol groups are referred to herein as "multi-thiol PEGs". As used herein, the term "polyethylene glycol(s)" includes modified and or derivatized polyethylene glycol(s).

Various forms of multi-amino PEG are commercially available from Shearwater Polymers (Huntsville, Ala.) and from Texaco Chemical Company (Houston, Tex.) under the name "Jeffamine" Multi-amino PEGs useful in the present invention include Texaco's Jeffamine diamines ("D" series) and triamines ("T" series), which contain two and three primary amino groups per molecule, respectively.

Polyamines such as ethylenediamine ($H_2N—CH_2CH_2—NH_2$), tetramethylenediamine ($H_2N—(CH_2)_4—NH_2$), pentamethylenediamine (cadaverine) ($H_2N—(CH_2)_5—NH_2$), hexamethylenediamine ($H_2N—(CH_2)_6—NH_2$), bis(2-hydroxyethyl)amine ($HN—(CH_2CH_2OH)_2$), bis(2)aminoethyl)amine ($HN—(CH_2CH_2NH_2)_2$), and tris(2-aminoethyl)amine ($N—(CH_2CH_2NH_2)_3$) may also be used as the first component synthetic polymer containing multiple nucleophilic groups.

C. Second Component Polymer

Second component polymers containing multiple electrophilic groups are also referred to herein as "multi-electrophilic polymers." For use in the present invention, the multi-electrophilic polymers often contain at least two, or at least three, electrophilic groups in order to form a three-dimensional crosslinked network with multi-nucleophilic polymers.

Multi-electrophilic polymers for use in the compositions of the invention can be polymers which contain two or more succinimidyl groups capable of forming covalent bonds with nucleophilic groups on other molecules. Succinimidyl groups are highly reactive with materials containing primary amino ($—NH_2$) groups, such as multi-amino PEG, poly(lysine), or collagen. Succinimidyl groups are slightly less reactive with materials containing thiol (—SH) groups, such as multi-thiol PEG or synthetic polypeptides containing multiple cysteine residues.

As used herein, the term "containing two or more succinimidyl groups" is meant to encompass polymers which are commercially available containing two or more succinimidyl groups, as well as those that are chemically derivatized to contain two or more succinimidyl groups. As used herein, the term "succinimidyl group" is intended to encompass sulfosuccinimidyl groups and other such variations of the "generic" succinimidyl group. The presence of the sodium sulfite moiety on the sulfosuccinimidyl group serves to increase the solubility of the polymer.

D. Hydrophilic Polymers for Use as First or Second Component Backbones

Hydrophilic polymers and, in particular, various polyethylene glycols, can be used in the first and second component polymer backbones according to some embodiments of the present invention. As used herein, the term "PEG" encompasses polymers having the repeating structure $(OCH_2CH_2)_n$.

Figure 3:
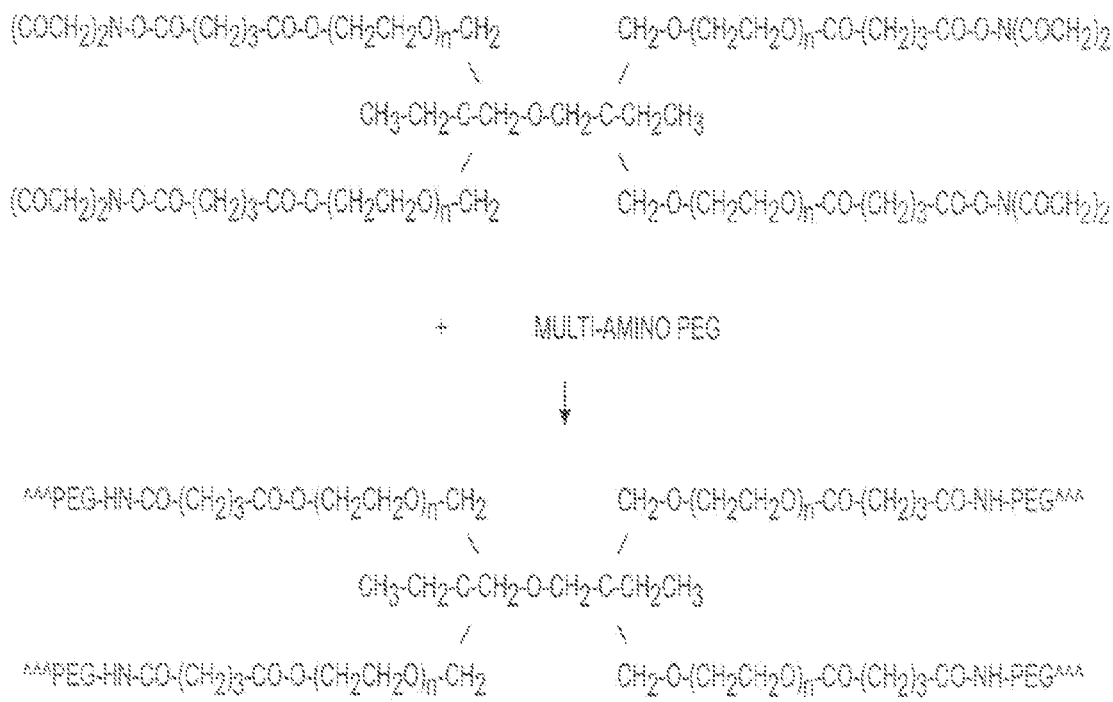
FIG. 3 shows the formation of a crosslinked matrix composition from a hydrophilic polymer according to some embodiments of the present invention.
Figure 4:
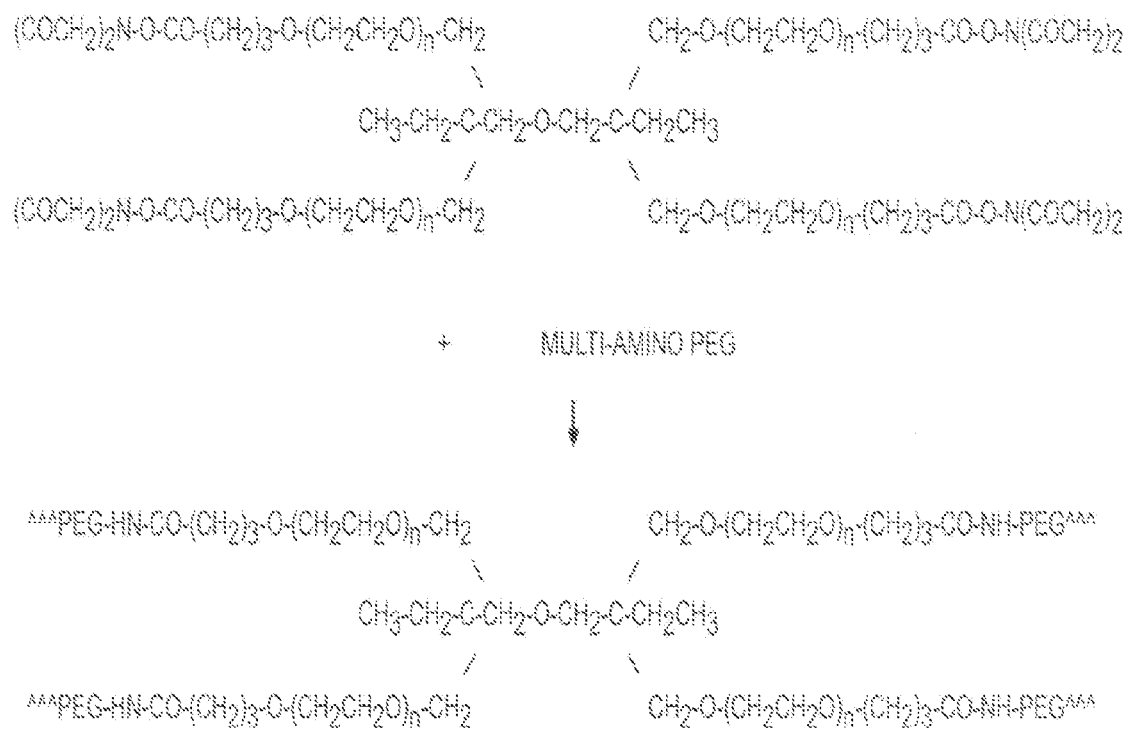
FIG. 4 shows the formation of a crosslinked matrix composition from a hydrophobic polymer according to some embodiments of the present invention.

A structure for a tetrafunctionally activated form of PEG is shown in FIG. 3, as is a generalized reaction product obtained by reacting a tetrafunctionally activated PEG with a multi-amino PEG. As depicted in the figure, the succinimidyl group is a five-member ring structure represented as $—N(COCH_2)_2$. In FIG. 3, the symbol ˆˆˆ denotes an open linkage.

Embodiments include the reaction of tetrafunctionally activated PEG succinimidyl glutarate, referred to herein as SG-PEG, with multi-amino PEG, and the reaction product obtained thereby. Another activated form of PEG is referred to as PEG succinimidyl propionate (SE-PEG). Embodiments include tetrafunctionally activated SE-PEG and the reaction product obtained by reacting it with multi-amino PEG. In some embodiments there are three repeating $CH_2$ groups on either side of the PEG. Further embodiments encompass a conjugate which includes an "ether" linkage which is less subject to hydrolysis. This is distinct from the conjugate shown in FIG. 3, wherein an ester linkage is provided. The ester linkage is subject to hydrolysis under physiological conditions. Other functionally activated forms of polyethylene glycol are contemplated by embodiments of the present invention, as are the conjugates formed by reacting tetrafunctionally activated PEGs with a multi-amino PEG. In some embodiments, a conjugate includes both an ether and an amide linkage. These linkages are stable under physiological conditions.

Another functionally activated form of PEG is referred to as PEG succinimidyl succinamide (SSA-PEG). Embodiments include the tetrafunctionally activated form of this compound and the reaction product obtained by reacting it with multi-amino PEG. These and related compounds may also be used in compositions according to embodiments of the invention. Embodiments also encompass a conjugate which includes an "amide" linkage which, like the ether linkage previously described, is less subject to hydrolysis and is therefore more stable than an ester linkage. Yet another activated form of PEG is provided in a compound embodiment referred to as PEG succinimidyl carbonate (SC-PEG). Embodiments include tetrafunctionally activated SC-PEG and the conjugate formed by reacting it with multi-amino PEG.

As discussed above, activated polyethylene glycol derivatives for use in embodiments of the invention can contain succinimidyl groups as the reactive group. However, different activating groups can be attached at sites along the length of the PEG molecule. For example, PEG can be derivatized to form functionally activated PEG propion aldehyde (A-PEG). Embodiments encompass the tetrafunctionally activated form as well as the conjugate formed by the reaction of A-PEG with multi-amino PEG. The linkage may be referred to as a $—(CH_2)_m$, —NH— linkage, where m=1-10.

Yet another form of activated polyethylene glycol is functionally activated PEG glycidyl ether (E-PEG). Embodiments encompass the tetrafunctionally activated compound, as well as the conjugate formed by reacting such with multi-amino PEG. Another activated derivative of polyethylene glycol is functionally activated PEG-isocyanate (I-PEG). Embodiments include conjugate formed by reacting such with multi-amino PEG. Another activated derivative of polyethylene glycol is functionally activated PEG-vinylsulfone (V-PEG). Embodiments include the conjugate formed by reacting such with multi-amino PEG.

Multifunctionally activated polyethylene glycols for use in compositions and other embodiments of the present invention can include polyethylene glycols containing succinimidyl groups, such as SG-PEG and SE-PEG, which can be in trifunctionally or tetrafunctionally activated form. Many of the activated forms of polyethylene glycol described above are now available commercially from Shearwater Polymers, Huntsville, Ala., and Union Carbide, South Charleston, W. Va.

E. Derivatization of the First and Second Component Polymers to Contain Functional Groups Certain polymers, such as polyacids, can be derivatized to contain two or more functional groups, such as succinimidyl groups. Polyacids for use in the present invention include, without limitation, trimethylolpropane-based tricarboxylic acid, di(trimethylol propane)-based tetracarboxylic acid, heptanedioic acid, octanedioic acid (suberic acid), and hexadecanedioic acid (thapsic acid). Many of these polyacids are commercially available from DuPont Chemical Company.

According to a general method, polyacids can be chemically derivatized to contain two or more succinimidyl groups by reaction with an appropriate molar amount of N-hydroxysuccinimide (NHS) in the presence of N,N'-dicyclohexylcarbodiimide (DCC).

Polyalcohols such as trimethylolpropane and di(trimethylol propane) can be converted to carboxylic acid form using various methods, then further derivatized by reaction with NHS in the presence of DCC to produce trifunctionally and tetrafunctionally activated polymers, respectively, as described in U.S. application Ser. No. 08/403,358. Polyacids such as heptanedioic acid ($HOOC—(CH_2)_2—COOH$), octanedioic acid ($HOOC—(CH_2)_2—COOH$), and hexadecanedioic acid ($HOOC—(CH_2)_{14}—COOH$) are derivatized by the addition of succinimidyl groups to produce difunctionally activated polymers.

Polyamines such as ethylenediamine ($H_2N—CH_2CH_2—NH_2$), tetramethylenediamine ($H_2N—(CH_2)_4—NH_2$), pentamethylenediamine (cadaverine) ($H_2N—(CH_2)_5—NH_2$), hexamethylenediamine ($H_2N—(CH_2)_6—NH_2$), bis(2-hydroxyethyl)amine ($HN—(CH_2CH_2OH)_2$), bis(2)aminoethyl)amine ($HN—(CH_2CH_2NH_2)_2$), and tris(2-aminoethyl)amine (N—(CH$_2$CH$_2$NH$_2$)$_3$) can be chemically derivatized to polyacids, which can then be derivatized to contain two or more succinimidyl groups by reacting with the appropriate molar amounts of N-hydroxysuccinimide in the presence of DCC, as described in U.S. application Ser. No. 08/403,358. Many of these polyamines are commercially available from DuPont Chemical Company.

In some embodiments, a first cross-linkable component (e.g. multi-amino PEG) is present at a concentration in the range of about 0.5 to about 20 percent by weight of the total cross-linkable component composition, and a second cross-linkable component is present at a concentration in the range of about 0.5 to about 20 percent by weight of the total cross-linkable component composition. For example, a final cross-linkable component composition having a total weight of 1 gram (1000 milligrams) could contain between about 5 to about 200 milligrams of the first cross-linkable component (e.g. multi-amino PEG), and between about 5 to about 200 milligrams of the second cross-linkable component.

In some embodiments, the weight ratio of the first cross-linkable component to the second cross-linkable component is in the range from about 20% to about 80%. In related embodiments, this ratio is in the range from about 45% to about 55%. In some cases, the ratio is about 50%. The weight ratio is determined on the basis of a gel strength test. The first cross-linkable component and the second cross-linkable component may have the same molecular weight.

II. HYDROGEL-FORMING COMPONENTS FOR USE IN THE SEALANT MATRIX COMPOSITION

Hydrogel-forming components for use according to the present invention can include resorbable biocompatible molecular cross-linked gels and hydrogels as discussed in U.S. Pat. Nos. 4,640,834; 5,209,776; 5,292,362; 5,714,370; 6,063,061; and, 6,066,325, which are hereby incorporated by reference. Materials made by the techniques described in these patents are commercially available under the FLO-SEAL trademark from the Baxter Healthcare Corporation, in a kit for mixture with thrombin solution for use as a hemostatic agent. Alternatively, any hydratable cross-linked polymers may be used as hydrogel-forming components in the invention. For example, alginates, agaroses, gelatins (e.g., SURGIFOAM™ powder), or other synthetic, carbohydrate or protein-based hydratable cross-linked polymers may be used. The primary characteristics of useful hydrogel-forming components are biocompatibility, rapid absorption and retention of fluid. Thus, although polyacrylamide may be used as a hydrogel-forming component in the invention, it would be less preferred due to its poor biocompatibility in many internal applications. Often, the hydratable cross-linked polymers for use as the hydrogel-forming component have a particle size of about 70 to about 300 microns, and a pH of about 6.8 to about 9.5. Hydrogel-forming components can provide mechanical stability to the first and second cross-linkable components, particularly when a sealant matrix is subject to forces, pressures, or dilutions.

In some embodiments, the weight ratio between the first and second cross-linkable components, and the hydrogel-forming component, is within a range from about 28% to about 42% w/w. In some cases, a composition may contain a concentration of combined first and second cross-linkable components that is about 5% to about 75% of the total mass of the composition, and a concentration of hydrogel forming component that is about 95% to about 25% of the total mass of the composition. Relatedly, a composition may contain a concentration of combined first and second cross-linkable components that is about 5% to about 40% of the total mass of the composition, and a concentration of hydrogel forming component that is about 95% to about 60% of the total mass of the composition. Similarly, a composition may contain a concentration of combined first and second cross-linkable components that is about 10% to about 30% of the total mass of the composition, and a concentration of hydrogel forming component that is about 90% to about 70% of the total mass of the composition. For example, a composition may contain about 20% combined first and second cross-linkable components, and about 80% hydrogel forming component. In some embodiments, a combined first and second cross-linkable component composition can have a fixed weight ratio of 50:50%, and the w/w ratio of the combined first and second cross-linkable component composition to the hydrogel-forming component can be with a range from about 20% to about 30%. The w/w ratio of the combined first and second cross-linkable component composition to the hydrogel-forming component can be selected based on a gel strength/adherence test. The hydrogel-forming component can act as an absorbent to provide a semi-dry surface for the first and second cross-linkable components to polymerize. Embodiments of the present invention encompass dry sealant matrix composition kits that include cross-linkable components and hydrogel-forming components in amounts according to these ratios.

According to some embodiments, the term "biocompatible" refers to materials that meet the criteria in standard #ISO 10993-1 promulgated by the International Organization for Standardization (NAMSA, Northwood, Ohio). According to some embodiments, the term "resorbable" refers to compositions that degrade or solubilize, when placed directly into a target site in a patient's body (and not protected within an implant device such as a breast implant), over a time period of less than one year, usually from 1 to 120 days. Protocols for measuring resorption and degradation are known. According to some embodiments, the term "molecular cross-linked" refers to materials that include polymer molecules (i.e. individual chains) which are attached by bridges composed of either an element, a group, or a compound, where the backbone atoms of the polymer molecules are joined by primary chemical bonds. Cross-linking may be effected in a variety of ways, as will be described in greater detail below.

According to some embodiments, the term "hydrogel" encompasses compositions that include a single phase aqueous colloid in which a biologic or non-biologic polymer, as defined in more detail below, absorbs water or an aqueous buffer. A hydrogel can comprise multiple sub-networks, where each sub-network is a molecular cross-linked hydrogel having dimensions which depend on the degree of hydration and are within the ranges set forth above. Often, the hydrogels will have little or no free water, i.e., water cannot be removed from the hydrogel by simple filtration.

"Percent swell" can be defined as the dry weight is subtracted from the wet weight, divided by the dry weight and multiplied by 100, where wet weight is measured after a wetting agent has been removed as completely as possible from the exterior of the material, e.g., by filtration, and where dry weight is measured after exposure to an elevated temperature for a time sufficient evaporate the wetting agent, e.g., 2 hours at 120° C.

"Equilibrium swell" can be defined as the percent swell at equilibrium after the hydratable cross-linked polymer material has been immersed in a wetting agent for a time period sufficient for water content to become constant, typically 18 to 24 hours.

"Target site" is typically the location to which the sealant matrix composition is to be delivered, usually a tissue breach or defect. Often, the target site will be the tissue location of interest, but in some cases the sealant matrix composition may be administered or dispensed to a location near the location of interest, e.g., when the material swells in situ to cover the location of interest.

The hydratable cross-linked polymers for use as hydrogel-forming components in at least some embodiments of the present invention may be formed from biologic and non-biologic polymers. Suitable biologic polymers include proteins, such as gelatin, soluble collagen, albumin, hemoglobin, casein, fibrinogen, fibrin, fibronectin, elastin, keratin, laminin, and derivatives and combinations thereof. Soluble non-fibrillar collagen is similarly suitable. Exemplary gelatin formulations are set forth below. Other suitable biologic polymers include polysaccharides, such as glycosaminoglycans (e.g., hyaluronic acid and chondroitin sulfate), starch derivatives, xylan, cellulose derivatives, hemicellulose derivatives, agarose, alginate, chitosan, and derivatives and combinations thereof. Suitable non-biologic polymers can be selected to be degradable by either of two mechanisms, i.e. (1) break down of the polymeric backbone or (2) degradation of side chains which result in aqueous solubility. Exemplary nonbiologic polymers include synthetics, such as polyacrylates, polymethacrylates, polyacrylamides, polyvinyl resins, polylactide-glycolides, polycaprolactones, polyoxyethylenes, and derivatives and combinations thereof.

The hydratable cross-linked polymer molecules for use as hydrogel-forming components may be cross-linked in any manner suitable to form an aqueous hydrogel. For example, these polymeric molecules may be cross-linked using bi- or poly-functional cross-linking agents which covalently attach to two or more polymer molecules chains. Exemplary bifunctional cross-linking agents include aldehydes, epoxies, succinimides, carbodiimides, maleimides, azides, carbonates, isocyanates, divinyl sulfone, alcohols, amines, imidates, anhydrides, halides, silanes, diazoacetate, aziridines, and the like. Alternatively, cross-linking may be achieved by using oxidizers and other agents, such as periodates, which activate side-chains or moieties on the polymer so that they may react with other side-chains or moieties to form the cross-linking bonds. An additional method of cross-linking comprises exposing the polymers to radiation, such as gamma radiation, to activate the side polymer to permit cross-linking reactions. Dehydrothermal cross-linking methods are also suitable. Dehydrothermal cross-linking of gelatin can be achieved by holding it at an elevated temperature, typically 120° C., for a period of at least 8 hours. Increasing the extent of cross-linking, as manifested in a decline in percent swell at equilibrium, can be achieved by elevating the holding temperature, extending the duration of the holding time, or a combination of both. Operating under reduced pressure can accelerate the cross-linking reaction. Preferred methods for cross-linking gelatin molecules are described below.

Hydrogels may include a plasticizer to increase the malleability, flexibility, and rate of degradation of the hydrogel. The plasticizer may be an alcohol, such as polyethylene glycol, sorbitol, or glycerol. Often, the plasticizer will be polyethylene glycol having a molecular weight ranging from about 200 to 1000 D, or having a molecular weight of about 400 D. The plasticizers can be present in the hydrogel at from about 0.1% by weight to about 30% by weight, preferably from 1% by weight to 5% by weight of the polymer composition. The plasticizers can be particularly beneficial for use with hydrogels having a high solids content, typically above 10% by weight of the composition (without plasticizer).

Exemplary methods for producing molecular cross-linked gelatins are as follows. Gelatin is obtained and placed in an aqueous buffer to form a non-cross-linked gel, typically having a solids content from about 1% to about 70% by weight, or from about 3% to about 10% by weight. The gelatin is cross-linked, typically by exposure to either glutaraldehyde (e.g. 0.01% to 0.05% w/w, overnight at 0° C. to 15° C. in aqueous buffer), sodium periodate (e.g. 0.05 M, held at 0° C. to 8° C. for 48 hours) or 1-ethyl-3-(3-dimethylaminopropyl) carbodiimide ("EDC") (e.g., 0.5% to 1.5% w/w, overnight at room temperature), or by exposure to about 0.3 to 3 megarads of gamma or electron beam radiation. Alternatively, gelatin particles can be suspended in an alcohol, such as methyl alcohol or ethyl alcohol, at a solids content of about 1% to about 70% by weight, or about 3% to about 10% by weight, and cross-linked by exposure to a cross-linking agent, typically glutaraldehyde (e.g., 0.01% to 0.1% w/w, overnight at room temperature). In the case of aldehydes, the pH is typically held from about 6 to about 11, or from about 7 to about 10. When cross-linking with glutaraldehyde, the cross-links are formed via Schiff bases which may be stabilized by subsequent reduction, e.g. by treatment with sodium borohydride. After cross-linking, the resulting granules may be washed in water and optionally rinsed in an alcohol, dried and resuspended to a desired degree of hydration in an aqueous medium having a desired buffer and pH. The resulting hydrogels may then be loaded into the applicators of the present invention, as described in more detail hereinafter. Alternatively, the hydrogels may be mechanically disrupted prior to or after cross-linking, also as described in more detail hereinafter.

Figures 5, 6:
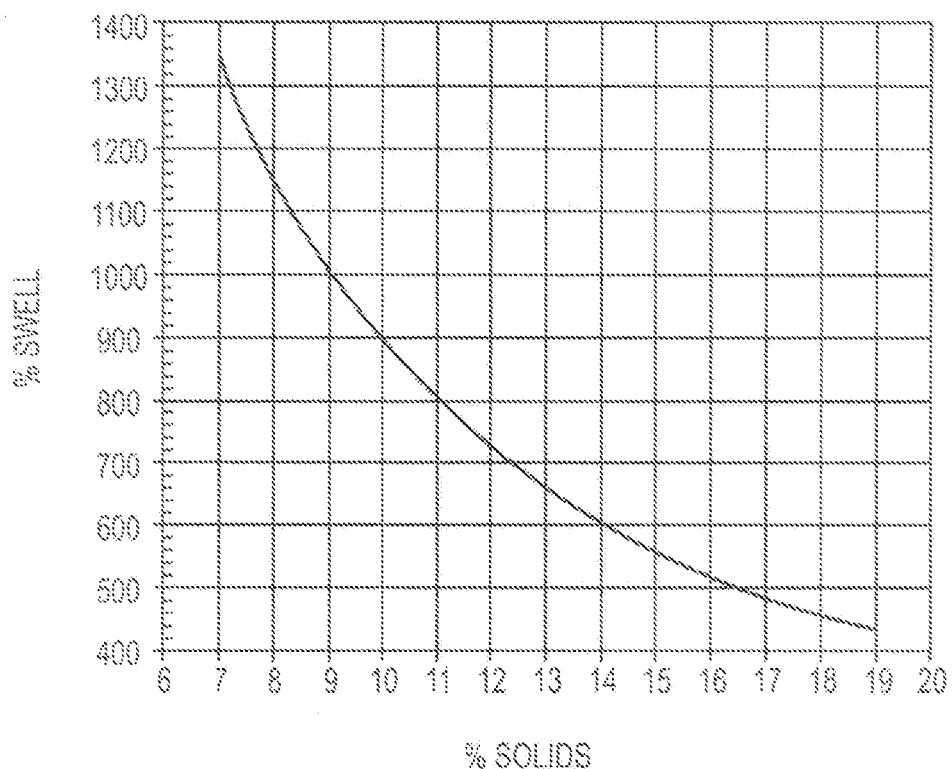
FIG. 5 illustrates a hydrogel-forming component subunit according to some embodiments of the present invention.
FIG. 6 illustrates the correlation between percent swell and the percent solids of a fragmented crosslinked polymeric gel useful as a hydrogel-forming component in a sealant composition according to some embodiments of the present invention.

Exemplary methods for producing molecular cross-linked gelatin compositions having equilibrium percent swells in the range from about 400% to about 1300%, or from about 600% to about 950%, are as follows. Gelatin is obtained and placed in an aqueous buffer (typically at a pH of about 6 to about 17, or at a pH between about 7 and about 10) containing a cross-linking agent in solution (often glutaraldehyde, typically at a concentration of 0.01% to 0.1% w/w) to form a gel, typically having a solids content from 1% to 70% by weight, usually from 3% to 10% by weight. The gel is well mixed and held overnight at 0° to 15° C. as cross-linking takes place. It is then rinsed three times with deionized water, twice with an alcohol (preferably methyl alcohol, ethyl alcohol, or isopropyl alcohol) and allowed to dry at room temperature. Optionally, the gel may be treated with sodium borohydride to further stabilize the cross-linking. In some cases, the hydrogel-forming component can include a gelatin having, for example, a large number of glycine residues (e.g. 1 in 3 arranged every third residue), proline residues, and 4-hydroxyproline residues. An exemplary gelatin subunit is shown in FIG. 5. Gelatin embodiments include molecules having an amino acid composition of: glycine 21%, proline 12%, hydroxyproline 12%, glutamic acid 10%, alanine 9%, arginine 8%, aspartic acid 6%, lysine 4%, serine 4%, leucine 3%, valine 2%, phenylalanine 2%, threonine 2%, isoleucine 1%, hydroxylysine 1%, methionine and histidine<1% and tyrosine<0.5%. FIG. 6 illustrates the correlation between percent swell and the percent solids of a fragmented crosslinked polymeric gel embodiment useful as a hydrogel-forming component in a sealant composition.

The molecular cross-linked hydrogels are preferably mechanically disrupted in a batch process prior for use as a hydrogel-forming component. The primary purpose of this mechanical disruption step is to create multiple subunits of hydrogel having a size which enhances the ability to fill and pack the space to which it is being delivered. Without mechanical disruption, the molecular cross-linked hydrogels will have difficulty conforming to and filling the irregularly shaped target spaces which are being treated. By breaking the hydrogel down to smaller sized sub-units, such spaces can be filled much more efficiently while retaining the mechanical integrity and persistence of the cross-linked hydrogel.

Molecular cross-linking of the polymer chains of the hydrogel can be performed before or after its mechanical disruption. The hydrogels may be mechanically disrupted in batch operations, such as mixing, so long as the hydrogel composition is broken down into sub-units having a size in the 0.01 mm to 5.0 mm range set forth above. Other batch mechanical disruption processes include pumping through a homogenizer or mixer or through a pump which compresses, stretches, or shears the hydrogel to a level which exceeds a fractural yield stress of the hydrogel. In some cases, extrusion of the polymeric composition causes the hydrogel to be converted from a substantially continuous network, i.e. a network which spans the dimensions of the original hydrogel mass, to a collection of sub-networks or sub-units having dimensions in the ranges set forth above.

In a presently preferred embodiment, the hydratable cross-linked polymer may be initially prepared (e.g. by spray drying) and/or be mechanically disrupted prior to being cross-linked, often usually prior to hydration to form a hydrogel. The hydratable cross-linked polymer may be provided as a finely divided or powdered dry solid which may be disrupted by further comminution to provide particles having a desired size, usually being narrowly confined within a small range. Further size selection and modification steps, such as sieving, cyclone classification, etc., may also be performed. For the exemplary gelatin materials described hereinafter, the dry particle size is preferably in the range from about 0.01 mm to about 1.5 mm, more preferably from about 0.05 mm to about 1.0 mm. An exemplary particle size distribution will be such that greater than about 95% by weight of the particles are in the range from about 0.05 mm to about 0.7 mm. Methods for comminuting the polymeric starting material include homogenization, grinding, coacervation, milling, jet milling, and the like. Powdered polymeric starting materials may also be formed by spray drying. The particle size distribution may be further controlled and refined by conventional techniques such as sieving, aggregation, further grinding, and the like.

The dry powdered solid may then be suspended in an aqueous buffer, as described elsewhere herein, and cross-linked. In other cases, the hydratable cross-linked polymer may be suspended in an aqueous buffer, cross-linked, and then dried. The cross-linked, dried polymer may then be disrupted, and the disrupted material subsequently resuspended in an aqueous buffer. In all the cases, the resulting material comprises a cross-linked hydrogel having discrete sub-networks having the dimensions set forth above.

The hydratable cross-linked polymers useful as hydrogel-forming components, after mechanical disruption, will typically be resorbable, i.e., they will biodegrade in the patient's body, in a period of less than one year, usually from 1 to 120 days, preferably from 1 to 90 days, and more preferably from 2 to 30 days following their initial application. Techniques for measuring the length of time required for resorption are known.

III. PREPARATION AND USE OF ONE GROUP OF EMBODIMENTS OF THE SEALANT MATRIX Compositions: Combination of Porous Matrix and Hydratable Cross-Linked Polymer Compositions according to the present invention comprise a first cross-linkable component combined with a second cross-linkable component which are capable of cross-linking to form a porous matrix having interstices, which is combined with a hydratable cross-linked polymer that is capable of being hydrated to form a hydrogel to fill at least some of the interstices. It will be appreciated that the compositions of the present invention can be used for a variety of biomedical applications, including each of the applications discussed above with reference to altering the (1) the first and second components (i.e. porous matrix); and, (2) the hydratable cross-linked polymer. For example, such compositions can act as a mechanical sealant to stop or inhibit bleeding by forming a rapid physical barrier to blood. Accordingly, some embodiments of the present invention can provide results without a direct "hemostatic" effect (e.g., biochemical effect on clotting cascade; involving clotting initiators).

The hydrogel-forming component can serve as an absorbent (e.g. for blood and other fluids and tissues). By absorbing blood, the hydrogel-forming component can ensure that a higher concentration of the first and second cross-linkable components is maintained at the treatment site, and can ensure that a semi-dry surface is provided for the first and second cross-linkable components to cross-link with each other and to the surrounding tissues. In some embodiments, the first and second components can cross-link at the same time the hydrogel-forming component is absorbing blood. This absorbtion and cross-linking can occur within a matter of seconds, and the resulting sealant matrix barrier can reach full strength at 30 minutes to one hour.

Generally, the sealant matrix compositions are "dry," although some minimal moisture content may be present, e.g., in the hydrogel-forming component. In some cases, it is possible to partially pre-hydrate the hydratable cross-linked polymer prior to application, although it may be necessary to do so at a higher pH than physiological pH, or under other conditions which will prevent the first and second components from cross-linking prior to application at the target site. Often, sealant matrix compositions will be in a powdered or fused-cake form.

The concentrations of the first component and the second component used to prepare the sealant matrix compositions may vary depending upon a number of factors, including the types and molecular weights of the particular cross-linkable components used and the desired end use application. In some embodiments, the weight ratio of the first and second components to the hydrogel-forming component ranges from 10-50% w/w, 15-45% w/w, 20-42% w/w, 30-40% w/w and 28 to about 42% w/w. In some embodiments, particle sizes for the first and second polymers can range from about 50 to about 90 microns. In some embodiments, particle sizes for the hydratable cross-linked polymer can range from about 250 to about 400 microns.

In some embodiments, the first and second components may be provided as in dry particulate or powder form. In this form the first and second components may be mixed together, and further may be mixed with the hydrogel-forming component, also in dry particulate or powder form. Mixture of the components may be accomplished by any mechanical admixture means, such as milling blade mixing. The resulting dry powder sealant matrix composition may then be packaged in various containers, e.g., cartons, envelops, jars, and the like. Admixture and filling may be done under aseptic conditions, or the sealant matrix composition may be sterilized after packaging, e.g., by gamma radiation. The dry powder embodiments of the invention are then ready for use. The first and second cross-linkable polymers will react to cross-link under physiological conditions (e.g., blood pH,) and so the three component sealant matrix composition of the composition may be applied directly at the desired site in dry form to seal a tissue defect, provided that sufficient hydrating bodily fluid is present. Thus, the powdered sealant matrix composition may simply be poured onto and into the tissue defect target site, and held in place (e.g., with a gauze pad or surgical glove) until the sealant matrix barrier forms. This is particularly useful and convenient in trauma situations (e.g., in an emergency suite or battlefield) where ready-to-use products that can be used with various tissue defect sizes are desirable.

In other embodiments, the first and second components and the hydrogel-forming component may be immobilized on a support, or backing, forming a "sealant matrix pad". In these embodiments, a support, such as a collagen sponge, is provided, and then the sealant matrix composition is fixed onto the support for use. Because the sealant matrix compositions bond easily with tissues, organic materials, and synthetic materials, these embodiments can be advantageous in that a more easily handled support may be used to apply the sealant matrix composition. Due to the fact that a relatively small amount of sealant matrix composition is required to create an effective sealant matrix barrier, a relatively thin layer of sealant matrix composition may be fixed to the support. For instance, in the examples set forth below, only about 0.5-1.0 g of sealant matrix composition fixed on the surface created a 3 cm×3 cm pad with very good haemostatic properties. As will be appreciated by those skilled in the surgical arts, these embodiments are desirable in situations where the size of the tissue defect is anticipated, and when improved handling characteristics as compared to a powder are desired. Like the dry powder embodiments, the sealant matrix pad embodiments of the sealant matrix compositions may be applied directly to the tissue defect without further preparation by pressing the sealant matrix composition side of the pad against the tissue defect until the cross-linkable components have cross-linked.

The support for the sealant matrix pad embodiments of the invention may be any biocompatible material. Although collagen supports are described in detail herein, other materials for supports may be used. For example, other protein or polysaccharide support material which are biocompatible may be used. These support materials may degrade at approximately the same rate in vivo as the sealant matrix barrier, or may degrade at different rates from the sealant matrix barrier. Collagen sponges and their preparation are well known in the surgical arts, and the preparation and handling of collagen is described fully below. Likewise, sponges prepared from fibrin may be used. Carbohydrate based materials such as cellulose (for external applications) or chitosan may also be used. In addition, biocompatible and biodegradable synthetic polymers may be used. Those of skill in the surgical arts will recognize that forms other than sponges may be used for supports in the sealant matrix pad embodiments of the invention. For example, a sheet or film of collagen or other materials may be used. In addition, the support may take any useful shape, such as cones, hemispheres, rods, wedges, and the like, in order to provide a pad that will more closely approximate the shape of the tissue defect. For example, a sealant matrix pad which utilizes a cone-shaped collagen sponge as a support may be useful in treating a gunshot wound.

Typically, such supports will act as a structural or mechanical component. The supports may have some degree of porosity, to allow blood or other liquids to seep into the support and have increased contact with the compositions. Such constructions may have a swelling factor of about 1.3× to about 1.5×, and therefore can be ideal for surgical applications. For example, the sponge-supported compositions can be used in neurosurgery to seal dura, where excessive swelling can place unwanted pressure on the brain. In general, the supports should be flexible enough to conform to a typical tissue defect, and should have good handling properties in the surgical context.

The sealant matrix compositions may be immobilized on the support by a variety of means. In some embodiments described below, gentle heat is sufficient to immobilize powdered sealant matrix compositions containing 4-arm PEG first and second components, and a cross-linked gelatin hydrogel-forming component. In these embodiments, the powdered sealant matrix composition was placed onto a collagen sponge, and heated to 60-70° C. for about 1-2 minutes. The dry powder matrix melted slightly at this heat, fixing it to the surface of the collagen sponge. Alternatively, the sealant matrix composition may be fixed to the support using binding agents, or other excipients known in the pharmaceutical arts. In general, the technique used to fix the sealant matrix composition to the support will depend on the first and second components and the hydrogel-forming component of the sealant matrix composition. The method used to fix the sealant matrix composition onto the support should not appreciably decrease the ability of the first and second component to cross-link when exposed to physiological conditions, or the ability of the hydrogel-forming component to absorb biological fluids.

In other embodiments, the sealant matrix composition may be formed into a sheet or film without a support. Such forming of the sealant matrix composition may be achieved using the methods described above for fixing a sealant matrix composition to a support for the sealant matrix pad embodiments.

IV. ADDITION OF ADDITIONAL COMPONENTS IN THE SEALANT MATRIX COMPOSITION

In additional embodiments of the present invention, components other than the first and second cross-linkable components and the hydrogel-forming component may be added to the sealant matrix compositions of the invention. In general, these additional components may be admixed with the first and second and hydrogel-forming components in dry form. Additional components may add further mechanical strength or otherwise improve the performance of the sealant matrix compositions of the invention for particular applications. For instance, because it is opaque and less tacky than nonfibrillar collagen, fibrillar collagen may sometimes be less preferred for use in bioadhesive compositions. However, as disclosed in U.S. Pat. No. 5,614,587, fibrillar collagen, or mixtures of nonfibrillar and fibrillar collagen, may be preferred for use in adhesive compositions intended for long-term persistence in vivo. Various deacetylated and/or desulfated glycosaminoglycan derivatives can be incorporated into the composition in a similar manner as that described above for collagen.

Naturally occurring proteins, such as collagen, and derivatives of various naturally occurring polysaccharides, such as glycosaminoglycans, can be incorporated into the sealant matrix barrier when the first and second components of the invention react under physiological conditions to cross-link. When these other components also contain functional groups which will react with the functional groups on the synthetic polymers, their presence during crosslinking of the first and second components at the target site will result in formation of a crosslinked synthetic polymer-naturally occurring polymer matrix. In particular, when the naturally occurring polymer (protein or polysaccharide) also contains nucleophilic groups such as primary amino groups, the electrophilic groups on the second cross-linkable component will react with the primary amino groups on these components, as well as the nucleophilic groups on the first cross-linkable component, to cause these other components to become part of the sealant matrix barrier.

In general, glycosaminoglycans are typically chemically derivatized by deacetylation, desulfation, or both in order to contain primary amino groups available for reaction with electrophilic groups on the second cross-linkable component. Glycosaminoglycans that can be derivatized according to either or both of the aforementioned methods include the following: hyaluronic acid, chondroitin sulfate A, chondroitin sulfate B (dermatan sulfate), chondroitin sulfate C, chitin (can be derivatized to chitosan), keratan sulfate, keratosulfate, and heparin. Derivatization of glycosaminoglycans by deacetylation and/or desulfation and covalent binding of the resulting glycosaminoglycan derivatives with synthetic hydrophilic polymers is described in further detail in commonly assigned, allowed U.S. Pat. No. 5,510,418, the contents of which are hereby incorporated by reference.

Similarly, electrophilic groups on the second cross-linkable component may react with primary amino groups on lysine residues or thiol groups on cysteine residues of certain naturally occurring proteins. Lysine-rich proteins such as collagen and its derivatives are especially reactive with electrophilic groups on synthetic polymers. As used herein, the term "collagen" is intended to encompass collagen of any type, from any source, including, but not limited to, collagen extracted from tissue or produced recombinantly, collagen analogues, collagen derivatives, modified collagens, and denatured collagens such as gelatin. Covalent binding of collagen to synthetic hydrophilic polymers is described in detail in commonly assigned U.S. Pat. No. 5,162,430, issued Nov. 10, 1992, to Rhee et al.

In general, collagen from any source may be used in the compositions of the invention; for example, collagen may be extracted and purified from human or other mammalian source, such as bovine or porcine corium and human placenta, or may be recombinantly or otherwise produced. The preparation of purified, substantially non-antigenic collagen in solution from bovine skin is well known in the art. U.S. Pat. No. 5,428,022, issued Jun. 27, 1995, to Palefsky et al., discloses methods of extracting and purifying collagen from the human placenta. U.S. Pat. No. 5,667,839 discloses methods of producing recombinant human collagen in the milk of transgenic animals, including transgenic cows. The term "collagen" or "collagen material" as used herein refers to all forms of collagen, including those which have been processed or otherwise modified.

Collagen of any type, including, but not limited to, types I, II, III, IV, or any combination thereof, may be used in the compositions of the invention, although type I is often preferred. Either atelopeptide or telopeptide-containing collagen may be used; however, when collagen from a xenogeneic source, such as bovine collagen, is used, atelopeptide collagen is often preferred, because of its reduced immunogenicity compared to telopeptide-containing collagen.

Collagen that has not been previously crosslinked by methods such as heat, irradiation, or chemical crosslinking agents can be used in the compositions of the invention, and previously crosslinked collagen may be used as well. Non-crosslinked atelopeptide fibrillar collagen is commercially available from Collagen Corporation (Palo Alto, Calif.) at collagen concentrations of 35 mg/ml and 65 mg/ml under the trademarks Zyderm® I Collagen and Zyderm II Collagen, respectively. Glutaraldehyde crosslinked atelopeptide fibrillar collagen is commercially available from Collagen Corporation at a collagen concentration of 35 mg/ml under the trademark Zyplast® Collagen. Collagens for use in the present invention are generally in dry lyophilized powder form.

Because of its tacky consistency, nonfibrillar collagen is typically used in compositions of the invention that are intended for use as bioadhesives. The term "nonfibrillar collagen" encompasses any modified or unmodified collagen material that is in substantially nonfibrillar form at pH 7, as indicated by optical clarity of an aqueous suspension of the collagen.

Collagen that is already in nonfibrillar form may be used in the compositions of the invention. As used herein, the term "nonfibrillar collagen" is intended to encompass collagen types that are nonfibrillar in native form, as well as collagens that have been chemically modified such that they are in nonfibrillar form at or around neutral pH. Collagen types that are nonfibrillar (or microfibrillar) in native form include types IV, VI, and VII.

Chemically modified collagens that are in nonfibrillar form at neutral pH include succinylated collagen and methylated collagen, both of which can be prepared according to the methods described in U.S. Pat. No. 4,164,559, issued Aug. 14, 1979, to Miyata et al., which is hereby incorporated by reference in its entirety. Due to its inherent tackiness, methylated collagen is typically used in bioadhesive compositions, as disclosed in U.S. Pat. No. 5,614,587.

Collagens for use in the sealant matrix compositions of the present invention may start out in fibrillar form, then be rendered nonfibrillar by the addition of one or more fiber disassembly agents. The fiber disassembly agent is typically present in an amount sufficient to render the collagen substantially nonfibrillar at pH 7, as described above. Fiber disassembly agents for use in the present invention include, without limitation, various biocompatible alcohols, amino acids, inorganic salts, and carbohydrates, with biocompatible alcohols being particularly preferred. Preferred biocompatible alcohols include glycerol and propylene glycol. In some cases, non-biocompatible alcohols, such as ethanol, methanol, and isopropanol, may not be desirable for use in the first and second polymers of the present invention, due to their potentially deleterious effects on the body of the patient receiving them. Examples of amino acids include arginine. Examples of inorganic salts include sodium chloride and potassium chloride. Although carbohydrates, such as various sugars including sucrose, may be used in the practice of the present invention, they are not as preferred as other types of fiber disassembly agents because they can have cytotoxic effects in vivo.

For use in tissue adhesion, in addition to sealing, it may also be desirable to incorporate proteins such as albumin, fibrin or fibrinogen into the sealant matrix composition to promote cellular adhesion. In addition, the introduction of hydrocolloids such as carboxymethylcellulose may promote tissue adhesion and/or swellability.

The sealant matrix compositions of the present invention may also comprise one or more additional biologically active agents or compounds. In one embodiment, biologically active agents such as taxol derivatives may be added to the sealant matrix composition to prevent adhesion at the tissue defect site. In other embodiments, biologically active agents such as antibiotic or antimicrobial agents may be added to the sealant matrix for use, e.g., in trauma-induced wound situations (e.g., knife or bullet wounds) where pathogenic organisms may have entered the tissue defect site, or wound. In other embodiments, biologically active agents such as growth factors may be delivered from the composition to a local tissue site in order to facilitate tissue healing and regeneration. In further embodiments, blood clotting agents, such as thrombin, may be added to further improve sealing and tissue regeneration by activating the clotting cascade. Exemplary bioactive components include, but are not limited to, proteins, carbohydrates, nucleic acids, and inorganic and organic biologically active molecules such as enzymes, antibiotics, antineoplastic agents, bacteriostatic agents, anti-adhesion formation agents (such as taxol derivatives,) bacteriocidal agents, antiviral agents, hemostatic agents, local anesthetics, anti-inflammatory agents, hormones, antiangiogenic agents, antibodies, neurotransmitters, psychoactive drugs, drugs affecting reproductive organs and oligonucleotides, such as antisense oligonucleotides. The term "biologically active agent" or "active agent" as used herein encompasses organic or inorganic molecules which exert biological effects in vivo. Examples of active agents include, without limitation, enzymes, receptor antagonists or agonists, hormones, growth factors, autogenous bone marrow, antibiotics, anti-adhesion formation agents, antimicrobial agents, other pharmaceutical agents, and antibodies. The term "active agent" is also intended to encompass combinations or mixtures of two or more active agents, as defined above.

Such bioactive components will typically be present at relatively low concentrations, typically below 10% by weight of the compositions, usually below 5% by weight, and often below 1% by weight. Two or more of such active agents may be combined in a single composition and/or two or more compositions may be used to deliver different active components where said components may interact at the delivery site. Exemplary hemostatic agents include thrombin, fibrinogen and clotting factors. Hemostatic agents like thrombin may be added in concentrations ranging, for example, from about 50 to about 10,000 Units thrombin per ml hydrogel, or from about 100 to about 1000 Units thrombin per ml hydrogel.

The crosslinked first and second polymer compositions can also be prepared to contain various imaging agents such as iodine or barium sulfate, or fluorine, in order to aid visualization of the compositions after administration via X-ray, or $^{19}$F-MRI, respectively.

Preferred active agents for use in the compositions of the present invention include growth factors, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are particularly preferred. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Biologically active agents may be incorporated into the sealant matrix composition by admixture. In one embodiment, active agents may be mixed into powdered sealant matrix compositions in a dry or lyophilized form. In another embodiment, this admixture may be fixed onto a solid support such as collagen as described above for the sealant matrix compositions. In other embodiments, the agents may be incorporated into the sealant matrix compositions, as described above, by binding these agents with the functional groups on the first or second component synthetic polymers. Processes for covalently binding biologically active agents such as growth factors using functionally activated polyethylene glycols are described in commonly assigned U.S. Pat. No. 5,162,430, issued Nov. 10, 1992, to Rhee et al. Such compositions preferably include linkages that can be easily biodegraded, for example as a result of enzymatic degradation, resulting in the release of the active agent into the target tissue, where it will exert its desired therapeutic effect.

A simple method for incorporating biologically active agents containing nucleophilic groups into the crosslinked polymer composition involves mixing the active agent with the first component, second component, and hydrogel forming component prior to administration in a dry state. Upon application of the sealant matrix composition to the tissue defect and contact with biological fluid, the biologically active agent will react with the second component and be cross-linked into the porous cross-linked matrix of the first and second components, as the hydrogel-forming component absorbs the biological fluid. This procedure will result in covalent binding of the active agent to the crosslinked component polymer matrix portion of the sealant matrix barrier which is formed, producing a highly effective sustained release composition.

The type and amount of active agent used will depend, among other factors, on the particular site and condition to be treated and the biological activity and pharmacokinetics of the active agent selected.

V. USE OF SEALANT MATRIX COMPOSITIONS AS BIOADHESIVES

The sealant matrix compositions of the present invention are generally adhesive and bond to tissues strongly, as the electrophilic groups of the second cross-linkable component react with nucleophilic groups of collagen in the tissue of the target site. Some porous matrix compositions of the invention can have unusually high tackiness. Thus, in addition to use as a barrier matrix for hemostasis, the sealant matrix compositions of the present invention are useful as bioadhesives to bond wet or moist tissues under physiological conditions. As used herein, the terms "bioadhesive", "biological adhesive", and "surgical adhesive" may be used interchangeably to encompass biocompatible compositions capable of effecting temporary or permanent attachment between the surfaces of two native tissues, or between a native tissue surface and a non-native tissue surface or a surface of a synthetic implant.

In a general method for effecting the attachment of a first surface to a second surface, the sealant matrix composition (for example, in dry powder or sheet form) is applied to a first surface. The first surface is then contacted with the second surface, preferably immediately, to effect adhesion between the two surfaces. At least one of the first and second surfaces is preferably a native tissue surface. When a mechanically stable hydrogel forming component is used in the composition, such as the crosslinked gelatin used in the examples, the resulting porous matrix exhibits increased mechanical strength as opposed to a composition containing the first and second cross-linkable components alone. Thus, the strength of the adhesion between the two tissue surfaces is also increased, as the layer of porous matrix between the tissues will be less likely to separate internally under physiological mechanical stresses.

The two surfaces may be held together manually, or using other appropriate means, while the crosslinking reaction is proceeding to completion. Crosslinking is typically complete within 5 to 60 minutes after applying the sealant matrix composition. However, the time required for complete crosslinking to occur is dependent on a number of factors, including the types and molecular weights of the first and second cross-linkable components and, most particularly, the effective concentrations of the two components at the target site (i.e., higher concentrations result in faster crosslinking times).

At least one of the first and second surfaces is preferably a native tissue surface. As used herein, the term "native tissue" encompasses biological tissues that are native to the body of the specific patient being treated. As used herein, the term "native tissue" encompasses biological tissues that have been elevated or removed from one part of the body of a patient for implantation to another part of the body of the same patient (such as bone autografts, skin flap autografts, etc.). For example, the compositions of some embodiments of the invention can be used to adhere a piece of skin from one part of a patient's body to another part of the body, as in the case of a burn victim.

The other surface may be a native tissue surface, a non-native tissue surface, or a surface of a synthetic implant. As used herein, the term "non-native tissue" encompasses biological tissues that have been removed from the body of a donor patient (who may be of the same species or of a different species than the recipient patient) for implantation into the body of a recipient patient (e.g., tissue and organ transplants). For example, the crosslinked polymer compositions of the present invention can be used to fix a xenograft heart valve into the heart of a patient and seal around the heart valve to prevent leakage.

As used herein, the term "synthetic implant" encompasses any biocompatible material intended for implantation into the body of a patient not encompassed by the above definitions for native tissue and non-native tissue. Synthetic implants include, for example, artificial blood vessels, heart valves, artificial organs, bone prostheses, implantable lenticules, vascular grafts, stents, and stent/graft combinations, etc.

VI. USE OF THE SEALANT MATRIX COMPOSITIONS TO PREVENT ADHESIONS

Another use of the sealant compositions of the invention is to coat tissues in order to prevent the formation of adhesions following surgery or injury to internal tissues or organs. In a general method for coating tissues to prevent the formation of adhesions following surgery, the first and second synthetic polymers are mixed with the hydratable crosslinked polymer or premixed, then a thin layer of the reaction mixture is applied to the tissues comprising, surrounding, and/or adjacent to the surgical site before substantial crosslinking has occurred between the nucleophilic groups on the first synthetic polymer and the electrophilic groups on the second synthetic polymer. Application of the reaction mixture to the tissue site may be by extrusion, sprinkling, brushing, spraying (as described above) for powdered compositions, by placement of a thin film or sheet of the sealant matrix composition onto the tissue, or by any other convenient means.

Following application of the reaction mixture to the surgical site, crosslinking is allowed to continue in situ prior to closure of the surgical incision. Once crosslinking has reached equilibrium, tissues which are brought into contact with the coated tissues will not stick to the coated tissues. At this point in time, the surgical site can be closed using conventional means (sutures, etc.).

In general, compositions that achieve complete crosslinking within a relatively short period of time (i.e., 5-15 minutes following mixture of the first synthetic polymer and the second synthetic polymer) may be preferred for use in the prevention of surgical adhesions, so that the surgical site may be closed relatively soon after completion of the surgical procedure. Furthermore, it is preferred that a hydratable crosslinked polymer with a relatively high mechanical strength be used in the compositions, such as the crosslinked gelatin used in the examples, to increase the mechanical stability of the coating.

The following examples describe the production and characterization of a first cross-linkable component with a second cross-linkable component and a hydrogel-forming component to form sealant matrix compositions, and are put forth so as to provide those of ordinary skill in the art with a complete disclosure and description of how to make the preferred embodiments of the conjugates, compositions, and devices and are not intended to limit the scope of what the inventors regard as their invention. Efforts have been made to ensure accuracy with respect to numbers used (e.g., amounts, temperature, molecular weight, etc.) but some experimental errors and deviation should be accounted for. Unless indicated otherwise, parts are parts by weight, molecular weight is weight average molecular weight, temperature is in degrees Centigrade, and pressure is at or near atmospheric.

VII. EXAMPLES

Example 1

First and Second Component Compositions for Use in Sealant Matrix: Preparation of Crosslinked Multi-Amino PEG Compositions The following stock solutions of various di-amino PEGs were prepared: Ten (10) grams of Jeffamine ED-2001 (obtained from Texaco Chemical Company, Houston, Tex.) was dissolved in 9 ml of water. Ten (10) grams of Jeffamine ED-4000 (also obtained from Texaco Chemical Company) was dissolved in 9 ml of water. 0.1 grams of di-amino PEG (3400 MW, obtained from Shearwater Polymers, Huntsville, Ala.) was dissolved in 300 µl of water. Each of the three di-amino PEG solutions prepared above was mixed with aqueous solutions of trifunctionally activated SC-PEG (TSC-PEG, 5000 MW, also obtained from Shearwater Polymers) as set forth in Table 1, below.

TABLE 1

Preparation of Crosslinked Polymer Compositions

| Di-amino PEG | TSC-PEG + Aqueous Solvent |
|---|---|
| 50 µl | 0 mg + 50 µl water |
| 50 µl | 10 mg + 50 µl PBS |
| 50 µl | 10 mg + 100 µl PBS |
| 250 µl | 50 mg + 500 µl PBS |

The solutions of di-amino PEG and TSC-PEG were mixed using syringe-to-syringe mixing. Each of the materials was extruded from the syringe and allowed to set for 1 hour at 37° C. Each of the materials formed a gel. In general, the gels became softer with increasing water content; the gels containing the least amount of aqueous solvent (water or PBS) were firmest.

Example 2

First and Second Component Compositions for Use in Sealant Matrix: Preparation of Crosslinked Poly(Lysine) Compositions Ten (10) milligrams of poly-L-lysine hydrobromide (8,000 MW, obtained from Peninsula Laboratories, Belmont, Calif.) in 0.1 ml phosphate buffer (0.2M, pH=6.6) was mixed with 10 mg of tetrafunctionally activated SE-PEG (10,000 MW, obtained from Shearwater Polymers, Huntsville, Ala.) in 0.1 ml PBS. The composition formed a soft gel almost immediately.

Example 3

First and Second Component Compositions for Use in Sealant Matrix: Effect of pH on Gel Formation of Tetra-Amino PEG/Tetra SE-PEG Formulations Gels comprising various concentrations of tetra-amino PEG and tetra SE-PEG at pH 6, 7, and 8 were prepared in petri dishes. Following mixing of the tetra-amino PEG and tetra SE-PEG, the dishes were tilted repeatedly; the gelation time was considered to be the point at which the formulation ceased to flow. The effect of pH on gelation time of the various tetra-amino PEG/tetra SE-PEG formulations at room temperature is shown in Table 2, below.

TABLE 2

Effect of pH on Gel Formation of Tetra-amino PEG/Tetra SE-PEG Formulations

| Tetra-amino PEG Conc. (mg/ml) | Tetra SE-PEG Conc. (mg/ml) | pH | Gelation Time |
|---|---|---|---|
| 20 | 20 | 6 | >90.0 min |
| 20 | 20 | 7 | 20.0 min |
| 20 | 20 | 8 | 1.4 min |
| 50 | 50 | 6 | 24.0 min |
| 50 | 50 | 7 | 3.5 min |
| 50 | 50 | 8 | 10.0 sec |
| 100 | 100 | 6 | 9.0 min |
| 100 | 100 | 7 | 47.0 sec |
| 100 | 100 | 8 | 10.0 sec |
| 200 | 200 | 6 | 2.0 min |
| 200 | 200 | 7 | 9.0 sec |
| 200 | 200 | 8 | 5.0 sec |

The time required for gel formation decreased with increasing pH and increasing tetra-amino PEG and tetra SE-PEG concentrations.

Example 4

Evaluation of Hydrogel-Forming Component Materials and Methods of Cross-Linking and Measuring Percent Swell Gelatin particles were allowed to swell in an aqueous buffer (e.g., 0.2 M sodium phosphate, pH 9.2) containing a cross-linking agent (e.g., 0.005 to 0.5% by weight glutaraldehyde). The reaction mixture was held refrigerated overnight and then rinsed three times with deionized water, twice with ethyl alcohol, and allowed to dry at ambient temperature. The dried, cross-linked gelatin was resuspended in an aqueous buffer at a low solids concentration (2-3%) at ambient temperature for a fixed period of time. Buffer was in substantial excess of the concentration needed for equilibrium swelling, and two phases (a hydrogel phase and a buffer) were present. The suspension containing wet hydrogel was then filtered by applying vacuum on a 0.8 μm nominal cut-off filter membrane (Millipore, Bedford, Mass.). After removal of extraneous buffer, the combined weight of the retained wet hydrogel and wet filter membrane was recorded. The hydrogel and membrane were then dried at approximately 120° C. for at least two hours, and the combined weight of the dried hydrogel residue and dried filter membrane was recorded. Several measurements of samples of wet filter membrane without hydrogel residue and dried filter membrane without hydrogel were also performed and were used to deduce the net weight of wet hydrogel and dry hydrogel. "Percent swell" was then calculated as follows:

$$\text{percent swell} = 100 \times [(\text{wet weight of hydrogel} - \text{dry weight of hydrogel})/\text{dry weight of hydrogel}]$$

Swell measurements were conducted at least in triplicate and averaged for a given sample of gelatin. The value of percent swell for samples resuspended in buffer for 18 to 24 hr prior to measuring wet weight was defined as "equilibrium swell."

The resulting cross-linked gelatin materials displayed equilibrium swell values in the range from 400% to 1300%. The degree of equilibrium swell depended on the method and extent of cross-linking.

Example 5

Hydrogel-Forming Components for Use in the Sealant Matrix: Fragmented Hydratable Cross-Linked Polymeric Product Composed of Gelatin Cross-Linked Using EDC Gelatin (Atlantic Gelatin, General Foods Corp., Woburn, Mass.) was allowed to dissolve in distilled water at 1 to 10% solids (w/w) (more preferably at 8%) at 70° C. 1-Ethyl-3-(3-dimethylaminopropyl) carbodiimide (EDC) (Sigma, St. Louis, Mo.) at 0.2% to 3.5% (or 0.2% to 0.3%) was then added. The resultant hydrogel formed on stirring was left at room temperature for one hour. The hydrogel was dried using a Freezone 12 freeze dry system, (Labconco, Mo.) and ground finely using a Waring Blender model No. 31BC91 (VWR, Willard, Ohio). The dried polymeric composition was then loaded into syringes and equilibrated with buffer. The equilibrium swell was determined to be at least 1000%. The results are shown in Table 3.

TABLE 3

| Gelatin (mg) | EDC | Swell (%) |
|---|---|---|
| 500 (8%) | 13.5 mg (0.25%) | 1080 |
| 500 (8%) | 13.5 mg (0.25%) | 1126 |
| 100 (7.4%) | 0.945 mg (0.35%) | 1620 |
| 100 (7.4%) | 9.45 mg (3.5%) | 1777 |

Example 6

Hydrogel-Forming Components for Use in the Sealant Matrix: Fragmented Hydratable Cross-Linked Polymeric Product Composed of Gelatin and Poly(L)Glutamic Acid, Cross-Linked Using EDC Gelatin (Atlantic Gelatin, General Foods Corp., Woburn, Mass.) was allowed to dissolve in distilled water at 1 to 10% solids (w/w) (more preferably at 6 to 8%) at 70° C., 0 to 10% (w/w) (more preferably 2-5%) Poly(L)glutamic acid (PLGA) (Sigma, St. Louis, Mo.) and 1-Ethyl-3-(3-dimethylaminopropyl) carbodiimide (EDC) (Sigma) at 0.2 to 3.5% (or 0.2 to 0.4%) were then added. The resultant hydrogel formed on stirring was left at room temperature for one hour. The hydrogel was allowed to swell in excess saline for a fixed period of time (for example 20 hr). The hydrogel was then filtered by applying vacuum on a filter membrane (Millipore, Bedford, Mass.). The equilibrium swell was determined to be at least 1500%. The results are shown in Table 4.

TABLE 4

| Gelatin (mg) | PLGA (mg) | EDC | Swell (%) |
|---|---|---|---|
| 375 (6%) | 125 (2%) | 13.5 mg (.25%) | 1510 |
| 375 (6%) | 125 (2%) | 13.5 mg (.25%) | 1596 |
| 250 (4%) | 250 (4%) | 13.5 mg (.25%) | 2535 |
| 250 (4%) | 250 (4%) | 13.5 mg (.25%) | 2591 |
| 250 (4%) | 250 (4%) | 13.5 mg (.25%) | 2548 |
| 250 (4%) | 250 (4%) | 13.5 mg (.25%) | 2526 |
| 200 (3.2%) | 300 (4.8%) | 13.5 mg (.25%) | 2747 |
| 200 (3.2%) | 300 (4.8%) | 13.5 mg (.25%) | 2677 |
| 200 (3.2%) | 300 (4.8%) | 13.5 mg (.25%) | 2669 |
| 150 (2.4%) | 350 (5.6%) | 13.5 mg (.25%) | 3258 |
| 150 (2.4%) | 350 (5.6%) | 13.5 mg (.25%) | 3434 |
| 150 (2.4%) | 350 (5.6%) | 13.5 mg (.25%) | 3275 |
| 75 (5.5%) | 25 (1.9%) | 0.945 mg (0.35%) | 2437 |
| 50 (3.7%) | 50 (3.7%) | 0.945 mg (0.35%) | 2616 |
| 25 (1.9%) | 75 (5.5%) | 0.945 mg (0.35%) | 5383 |
| 75 (5.5%) | 25 (1.9%) | 9.45 mg (3.5%) | 1976 |
| 50 (3.7%) | 50 (3.7%) | 9.45 mg (3.5%) | 2925 |
| 25 (1.9%) | 75 (5.5%) | 9.45 mg (3.5%) | 4798 |

Example 7

Hydrogel-Forming Components for Use in the Sealant Matrix: Production of a Fragmented Hydratable Cross-Linked Polymeric Hydrogel Bovine Corium (Spears Co. PA) was agitated in an aqueous sodium hydroxide (Spectrum Chemical Co., CA) solution (0.1 M to 1.5 M, or 0.4 to 1.2M) for a period of one to 18 hours (or one to four hours) at a temperature of 2° C. to 30° C. (preferably 22° C. to 30° C.). The corium slurry was then neutralized using an inorganic acid such as hydrochloric acid, phosphoric acid or sulfuric acid (Spectrum Chemical Co., CA.) and the neutralized liquid phase was then separated from the insoluble corium by filtration through a sieve. The corium was then washed with non-pyrogenic water and an alcohol such as isopropyl alcohol (Spectrum Chemical Co., CA.). After three to twelve washes, the corium was suspended in non-pyrogenic water and the corium, water slurry may be then heated to 50° C. to 90° C. preferably 60° C. to 80° C. to thermally gelatinize the corium. During the gelatinization cycle, the pH of the corium, water slurry was adjusted and controlled from pH 3 to pH 11, or pH 7 to pH 9. Also, the insoluble corium in the slurry may be disrupted by agitation and/or homogenization. The disruption can occur before or after the thermal gelatinization cycle. Thermal gelatinization was conducted for one to six hours. After gelatinization, the slurry was clarified by filtration. The gelatin slurry was dewatered by drying in air at 15° C. to 40° C., preferably 20° C. to 35° C. The dry gelatin, where dry implies a moisture content less than 20% by weight, was then disrupted by grinding.

Dry gelatin was added to a cold (5° C. to 15° C.) aqueous solution of containing glutaraldehyde (Amresco Inc., OH.) at 0.0025% to 0.075% by weight and at a pH between 7 and 10. The concentration of gelatin in this solution was between 1% and 10% by weight. The glutaraldehyde cross-links the gelatin granules over a period of one to 18 hours after which the gelatin was separated from the aqueous phase by filtration or sedimentation. The gelatin particles were then added to an aqueous solution containing 0.00833% to 0.0667% by weight sodium borohydride (Spectrum Chemical Co., CA.) with the gelatin concentration again being between 1% and 10% by weight and the pH being between 7 and 12, or between 7 to 9. After one to six hours, the cross-linked gelatin was separated from the aqueous phase by filtration or sedimentation. The gelatin may then be resuspended in non-pyrogenic water with the gelatin concentration being between 1% and 10% by weight to remove residual cross-linking and reducing agents followed by separation from the aqueous phase by filtration or sedimentation. Final collection of the cross-linked gelatin was done on a filter mesh or sieve and the gelatin was given a final rinse with non-pyrogenic water. The wet, cross-linked gelatin was then placed in a drying chamber at 15° C. to 40° C. Dry, cross-linked gelatin (i.e. cross-linked gelatin with a moisture content below 20% by weight) was removed from the drying chamber and then ground using a mechanical, grinding mill to produce a powder with a typical particle size distribution from 0.020 mm to 2.000 mm.

Example 8

Rapidly Acting Dry Hemostatic Sealant Powder

A rapidly acting dry hemostatic sealant powder was prepared by combining a first cross-linkable component, a second cross-linkable components, and a hydrogel-forming component. The first cross-linkable polymer (PEG-A) was a PEG-succinimidyl powder, the second cross-linkable polymer (PEG-B) was a PEG-thiol powder, and the hydrogel-forming component was a cross-linked gelatin powder.

Example 9

Rapidly Acting Dry Sealant Pad

A rapidly acting dry sealant pad was prepared by combining a first cross-linkable component, a second cross-linkable components, and a hydrogel-forming component. The resulting composition, a powdered sealant matrix composition, was placed onto a lyophilized collagen sponge, and heated to 60-70° C. for about 1-2 minutes. The dry powder matrix melted slightly at this heat, fixing it to the surface of the collagen sponge, thus forming a sealant matrix pad. Alternatively, the sealant matrix composition may be fixed to the support using binding agents, or other excipients known in the pharmaceutical arts. In general, the technique used to fix the sealant matrix composition to the support may depend on the first and second components and the hydrogel-forming component of the sealant matrix composition. Sealant matrix pad embodiments of the present invention provide a convenient format by which sealant matrix compositions may be handled and delivered to a surgical site via a sponge or other suitable support means.

Example 10

Sealant Powder to Treat Splenic Artery Puncture

Figure 7A:
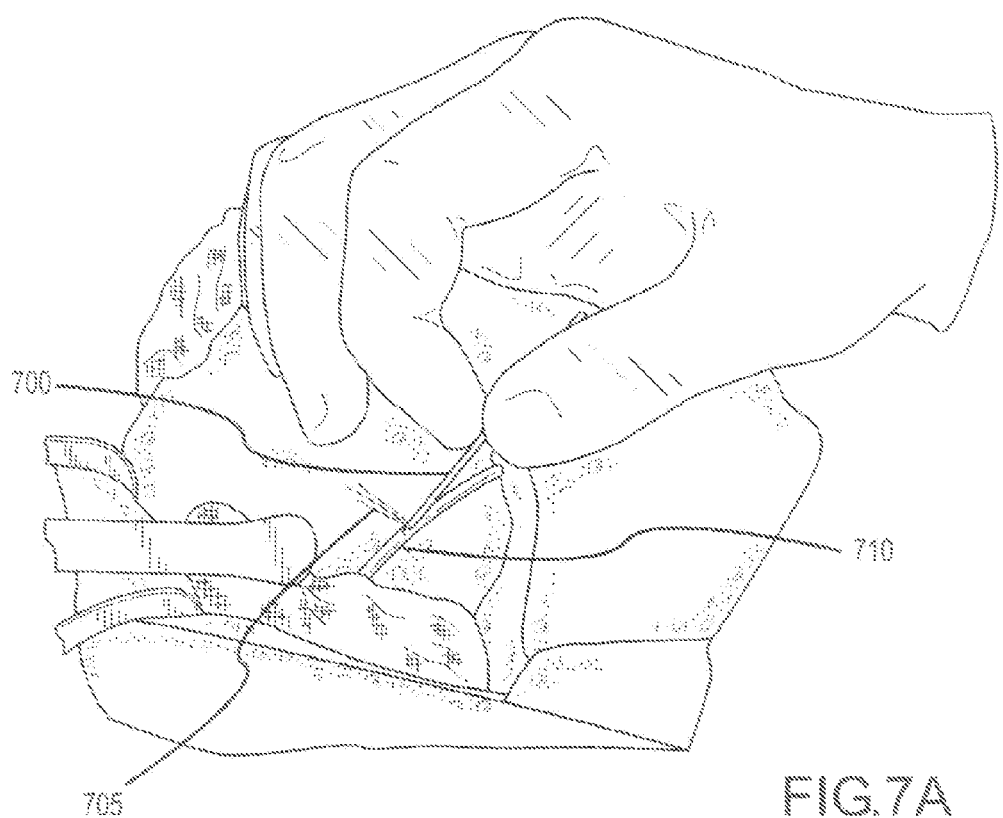
FIGS. 7A-E illustrate the application of a sealant matrix composition to treat a splenic artery puncture according to embodiments of the present invention.
Figure 7B:
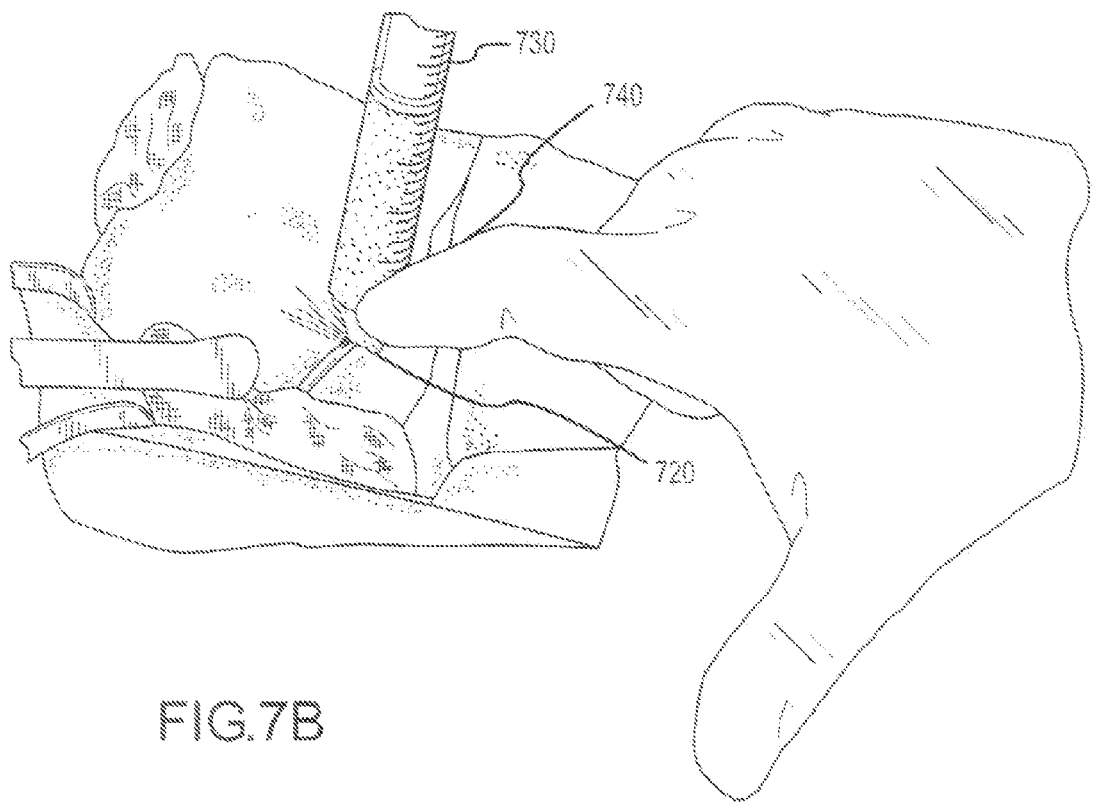
Figure 7C:
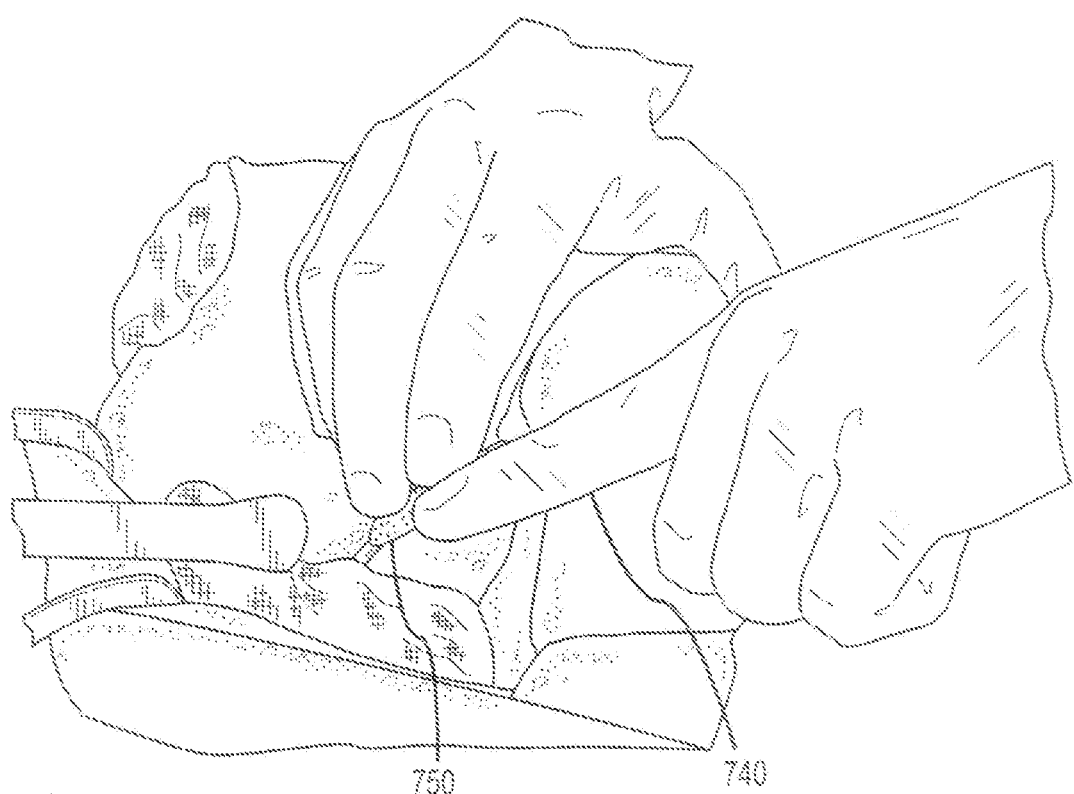
Figure 7D:
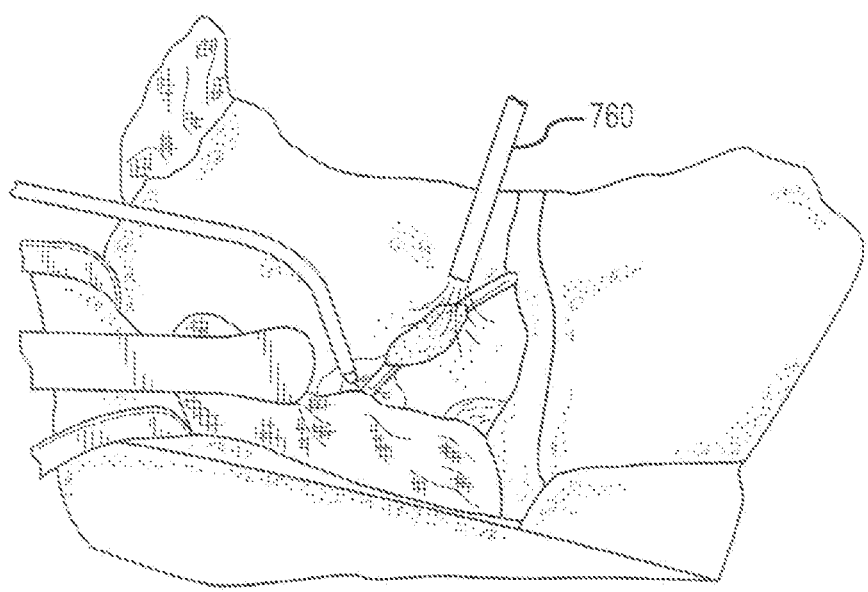
Figure 7E:
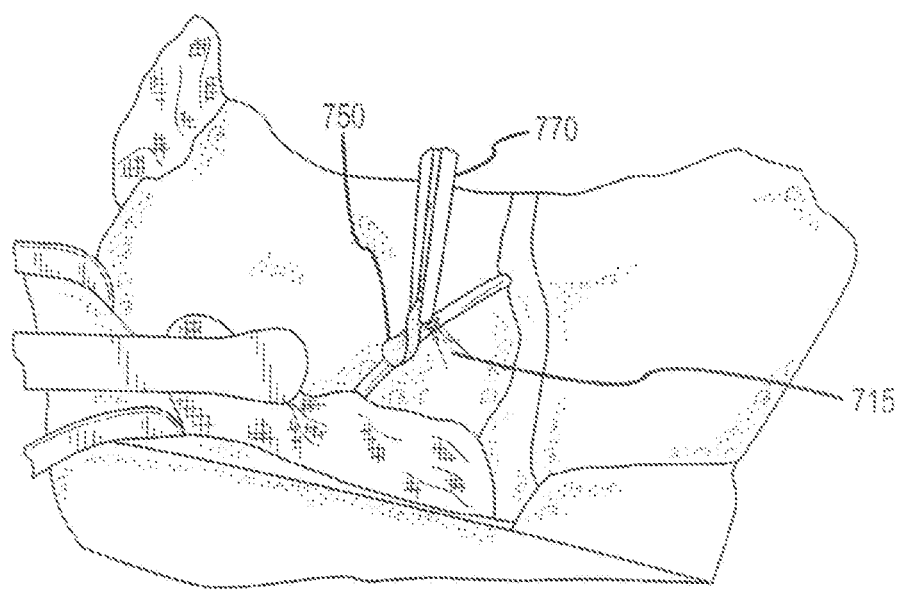

FIGS. 7A-E illustrate the application of a sealant matrix composition to treat a splenic artery puncture according to embodiments of the present invention. The pig was heparinized to approximately 3× baseline. As depicted in FIG. 7A, a splenic artery puncture was surgically induced in a pig with an 18 g needle 700. Following the puncture, excessive bleeding 705 was observed from the artery 710. As shown in FIGS. 7B and 7C, approximately 700 mg of a sealant powder matrix composition 720 was applied to the puncture site via a syringe 730, and gently compressed or placed against the site for two minutes using a gloved finger 740. The sealant powder formed a coagulum 750 that was observed to adequately stop the bleeding. The site was irrigated at 5 minutes post-application with an irrigation device 760, as illustrated in FIG. 7D, and excess powder composition was washed away. When the coagulum was grasped with forceps, it appeared to adhere quite well to the tissue and had good integrity. As shown in FIG. 7E, the coagulum 750 was removed at 44 minutes post-application, by peeling off with forceps 770, and resumed bleeding 715 was observed.

Example 11

Sealant Powder to Treat Hepatic Resection

Figure 8A:
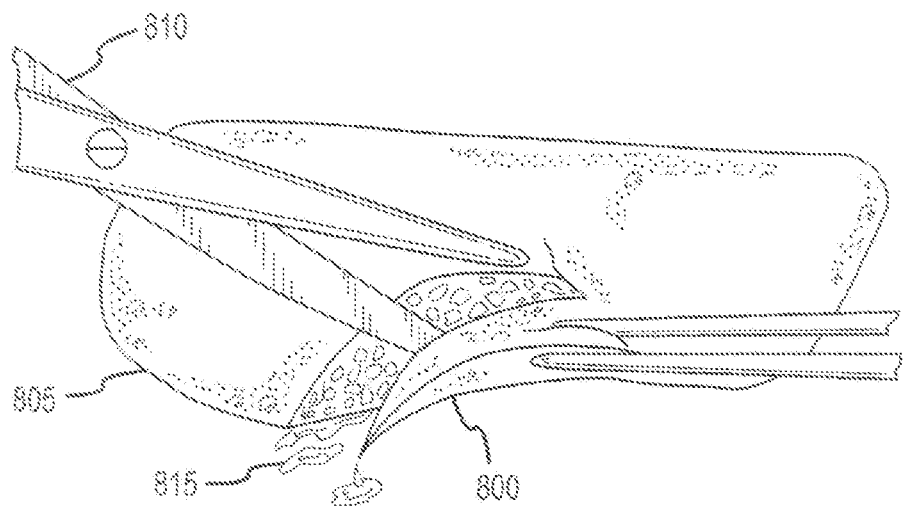
FIGS. 8A-E illustrate the application of a sealant matrix composition to treat a hepatic resection according to embodiments of the present invention.
Figure 8B:
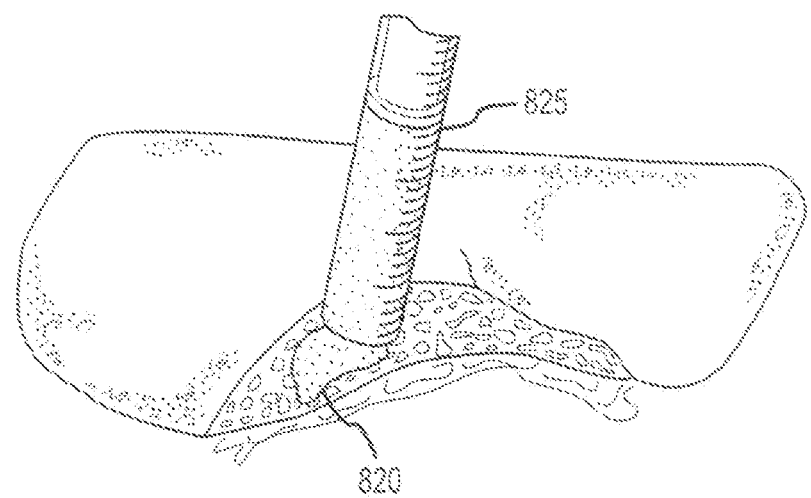
Figure 8C:
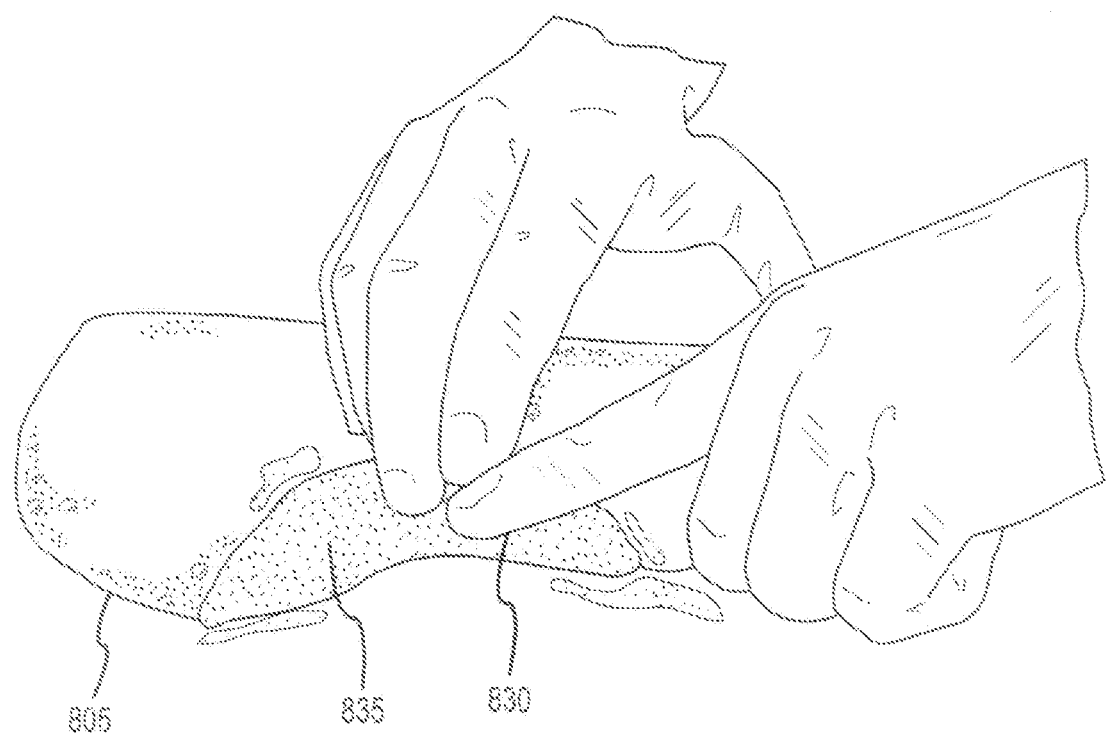
Figure 8D:
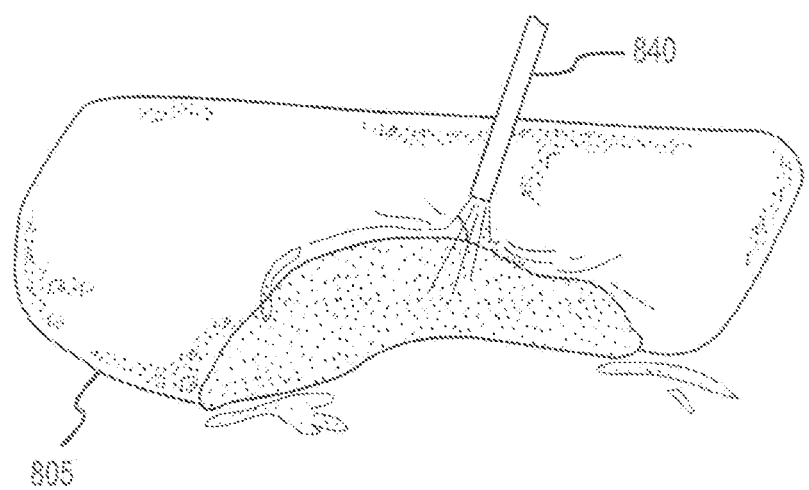
Figure 8E:
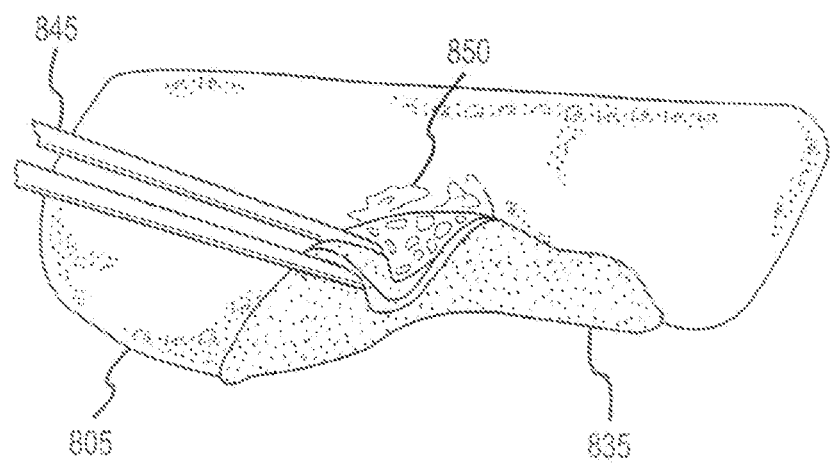

FIGS. 8A-E illustrate the application of a sealant matrix composition to treat a hepatic resection according to embodiments of the present invention. A pig was heparinized to approximately 3× baseline. As shown in FIG. 8A, the tip 800, or edge, of the middle lobe of the liver 805 was resected in the pig using scissors 810. Following the resection, excessive bleeding 815 was observed from the site. As depicted in FIG. 8B, approximately 6 ml (2 g) of a sealant matrix composition 820 was applied to the site, and held in place with the tip of a syringe 825 for 2 minutes. As shown in FIG. 8C, a gloved finger can be used to compress or hold the powder against the lesion. The sealant powder formed a coagulum 835 that was observed to adequately stop the bleeding. The site was irrigated at 8 minutes post-application with an irrigation device 840, as illustrated in FIG. 8D. When the coagulum was grasped with forceps, it appeared to adhere quite well to the tissue and had good integrity. The coagulum 835 was removed at 28 minutes post-application, by peeling off with forceps 845, and resumed bleeding 850 was observed.

Example 12

Sealant Powder to Treat Splenic Lesion

A splenic lesion was surgically induced in a pig with a 6 mm biopsy tissue punch, and the tissue core was removed with scissors. The pig was heparinized to approximately 2.5× baseline. Following the tissue punch, excessive bleeding was observed from the spleen. Approximately 700 mg (2 ml) of a sealant matrix composition powder was applied to the puncture using the edge of a 12 ml syringe. No compression was used to hold the material in place. The sealant powder formed a coagulum that was observed to adequately stop the bleeding. The site was irrigated at 4 minutes post-application. When the coagulum was grasped with forceps, it appeared to adhere quite well to the tissue and had good integrity. The coagulum was removed at 25 minutes post-application, by peeling off, and resumed bleeding was observed.

Example 13

Mechanical Stress Test

Sealant matrix barrier was prepared by reacting 0.60 to 0.65 g of a sealant matrix composition powder with 1 ml porcine plasma in a plastic mold. The mixture was allowed to cure at room temperature for approximately 30 minutes. Both ends of a 3×1×0.3 cm block of gel were taped with cyanoacrylate glue to create gripping spaces for pulling apart (1×1 cm). The tape ends were gripped with the pre-mounted grips. A Chatillon TCD2000 tester was used to apply a normal stress test to the rectangular gel shape until fracture, to determine the tensile strength. Peak force (N) and deflection at maximum load (mm) were measured to extend the gel until break. The effective surface area of the gel was 1×0.3 cm, and the original effective length of the gel was 1 cm. The tensile strength of the sealant gel was approximately 15.3 N/cm$^2$. A similar test was performed on a gel composition including a first cross-linkable component and a second cross-linkable component, in the absence of a hydrogel-forming component, and the observed tensile strength was approximately 5.1 N/cm$^2$.

Example 14

Peel Strength Test

In some embodiments, a mixed powder includes first and second cross-linkable components and a hydrogel-forming component, and is self-polymerizing as it dissolves in a physiological liquid such as blood or another body fluid. The material can tightly adhere to a tissue or another application site by covalent bonding. The mechanical strength of tissue adherence can be examined using a mechanical jig to pull a sealant matrix from a tissue such as skin. In this example, multiple tensile tests were run following formation of sealant matrix barriers as follows. A series of three component powders containing a first cross-linkable component (pentaerythritol poly(ethylene glycol)ether tetra-succinimidyl glutarate) and a second cross-linkable component (pentaerythritol poly(ethylene glycol)ether tetra-thiol), and a cross-linked gelatin (FloSeal™) were prepared, by mixing the cross-linkable components and the cross-linked gelatin at three different concentrations (10%, 20%, and 30% of the cross-linkable component). About 0.40 g to about 0.45 g of the three component powder was added to about 0.6 ml of porcine plasma in a 3×1×0.3 cm plastic mold disposed on top of a chicken skin sample, and allowed to cure at room temperature for approximately 60 minutes. A sealant matrix barrier formed and tightly adhered to the skin. The formed sealant matrix barrier was glued to a plate that was clamped to a Chatillon TCD200 tester. Maximum peak force (N) was measured as skin was pulled from the sealant matrix barrier. An increase in adhering strength was observed to almost linearly correlate with an increase in concentration of the PEG mixture (first and second cross-linkable components). Results are as shown in Table 4A.

TABLE 4A

| Conc. of PEG mixture | Skin | Speed, mm/min | Curing Time, min | Pulling side, cm | Force N |
|---|---|---|---|---|---|
| 10% | chicken | 12.7 | 80 | 1 | 2.00 |
| 10% | chicken | 12.7 | 80 | 1 | 2.10 |
| 10% | chicken | 12.7 | 80 | 1 | 1.70 |
| | | | | | 1.93 Avg. |
| | | | | | 0.21 Std. Dev. |
| 20% | chicken | 12.7 | 60 | 1 | 3.24 |
| 20% | chicken | 12.7 | 60 | 1 | 2.13 |
| 20% | chicken | 12.7 | 60 | 1 | 3.41 |
| 20% | chicken | 12.7 | 70 | 1 | 2.10 |
| | | | | | 2.72 Avg. |
| | | | | | 0.71 Std. Dev. |
| 30% | chicken | 12.7 | 70 | 1 | 3.86 |
| 30% | chicken | 12.7 | 70 | 1 | 7.86 |
| 30% | chicken | 12.7 | 80 | 1 | 1.53 |
| 30% | chicken | 12.7 | 80 | 1 | 2.65 |
| 30% | chicken | 12.7 | 80 | 1 | 2.59 |
| 30% | chicken | 12.7 | 80 | 1 | 3.83 |
| 30% | chicken | 12.7 | 105 | 1 | 3.32 |
| 30% | chicken | 12.7 | 107 | 1 | 3.00 |
| | | | | | 3.58 Avg. |
| | | | | | 1.89 Std. Dev. |

Example 15

Preparation of Fibrillar Collagen for Sponge Backing of Fused Pad

A first fibrillar collagen sample was prepared as follows. 40 g of NaOH was dissolved in 450 cc $H_2O$ at a temperature of 25° C. Approximately 50 g of sliced bovine corium was added to the NaOH solution. The corium was stirred for 80 minutes. The NAOH solution was decanted and the corium was washed with $H_2O$. The corium was dissolved with 2M HCl to bring the pH in the range of 2.3 to 2.4. Stirring was continued for 18 hours. 1250 ml of thick collagen in solution (CIS) was titrated to pH 7.25 with 1M NaOH at 18° C. Collagen fiber was formed over a period of 10 hours, and filtered. 240 ml of was precipitated at pH 7.4, and cross-linked with 33 µl of 25% glutaraldehyde (GA) solution at 8° C. for 23 hours. Fibrillar collagen was lyophilized using a Virtis Lyophilizer by a recipe cycle.

A second fibrillar collagen sample was prepared as follows. Fibrillar collagen was cross-linked using 240 g of viscous solution (e.g. CIS). The solution was diluted by adding 60 cc of $H_2O$. The pH was raised to 9.2 by adding about 1.8 cc of 2M NaOH. The temperature of the solution was adjusted to 8° C., and 33 µl of 25% GA was added. The solution was stirred for 23 hours, and about 54 g of precipitated fibers were obtained. Fibrillar collagen was lyophilized using a Virtis Lyophilizer by a recipe cycle.

Example 16

De-Buffering the Hydrogel-Forming Component

In some embodiments, it may be desirable to remove phosphate salt from a hydrogel-forming component such as FloSeal™ so that the pH of the hydrogel-forming component can be easily influenced by the surrounding liquid. In-situ cross-linking of hydrogel-forming components can help a sealant matrix compound adhere to tissue following application. In some cases, the adhesion may be more effective at certain pH values. For example, some gelatin-based materials may undergo adhesion more readily at pH values lower than 6 or 7. FloSeal™ was washed with $H_2O$ in a ratio of 1:50, and the slurry was pH adjusted or acidified with 0.01 M HCl or 0.01 M NaOH to a pH between 2 and 7. Wet gelatin cake was filtered and dried in a forced air oven at 32° C. for 12 to 20 hours and lightly ground with mortar and pestle. Dried gelatin powder was added to a solution of mixed PEG for in situ crosslinking. A slurry was mixed for 30 seconds and immediately applied to the surface of weighing paper fully saturated with 25 mM of phosphate buffer at pH 7.4. Polymerization times were recorded, and the results are shown in Table 5.

TABLE 5

| Sample | pH of FloSeal ™ | pH of buffer for PEG (A/B) | Time (minutes) gelation |
|---|---|---|---|
| 1 | 7.6 | 6 | 3 |
| 2 | 7.6 | 6 | 5 |
| 3 | 6.0 | 6 | 30 |
| 4 | 6.5 | 6 | 20 |
| 5 | 4.0 | 6 | 90 |

Example 17

Preparation of PEG Cake

In one embodiment, 0.8 g PEG-succinimide powder and 0.8 g PEG-thiol powder were thoroughly mixed by shaking, and placed in a 100 ml round bottom flask which was fully charged with $N_2$. The mixed powder was melted in a 40° C.-50° C. oil bath with gentle manual stirring for 30 minutes, and allowed to cool. A solid film was removed from the flask using a spatula. In another embodiment, a mixed powder of PEG-succinimide and PEG-thiol was dissolved in an acidic solution of collagen (e.g. 0.3%) or gelatin (e.g. 2%), and lyophilized. It is thought that the fibrillar collagen or gelatin may help to loosen the matrix and improve handling of the PEG cake.

In a comparative composition, 1.2 g of collagen fiber was dissolved in 100 cc of pH 2 HCl, warmed in a 35° C. water bath for 1 to 2 hours, and diluted with pH 2 HCl to achieve a 0.3% CIS product. 0.2 g PEG-succinimide and 0.2 g PEG-thiol were dissolved in 2 cc of the 0.3% CIS. The resulting mixture was poured into a tray, and lyophilized through a 22 hour cycle to produce a PEG cake. In yet another embodiment, 2 g of gelatin was dissolved in 100 cc pH 2 HCl, in a water bath at 35° C. 4 g of a two component PEG powder mixture was dissolved in 2 cc of the gelatin solution, and lyophilized to provide a PEG cake.

In a related embodiment, PEG cakes were prepared by lyophilizing mixed solutions of PEG-SG, PEG-SH, and collagen at pH 2.0. Animal studies were performed on abraded liver capsules in a heparinized porcine model. Two drops of 0.2M phosphate buffer (pH 9.0) were added to the liver surface, which was bleeding slowly. A piece of cake was placed on the site without any compression. At 5 and 10 minutes, the adhesion of each of the PEG cakes to the site were tested. It was observed that the activity of PEG-SG was not reduced during the preparation process, and that the PEG cakes adhered to the abraded liver tissue by covalent bonding. The composition and in vivo performance of the tested samples are summarized in Table 6.

TABLE 6

| Sample | Conc. of PEG-GS (%, w/v) | Conc. of PEG-SH (%, w/v) | Conc. of gelatin (%, w/v) | Conc. of CIS (%, w/v) | Mass % collagen in PEG after lyophilization | In vivo performance (adhesion) |
|---|---|---|---|---|---|---|
| 1 | 20 | 20 | 2 | 0 | 1.0% | Excellent |
| 2 | 20 | 20 | 0 | 0.29 | 1.5% | Excellent |
| 3 | 20 | 20 | 0 | 0.52 | 2.6% | Good |

Example 18

Figure 9:
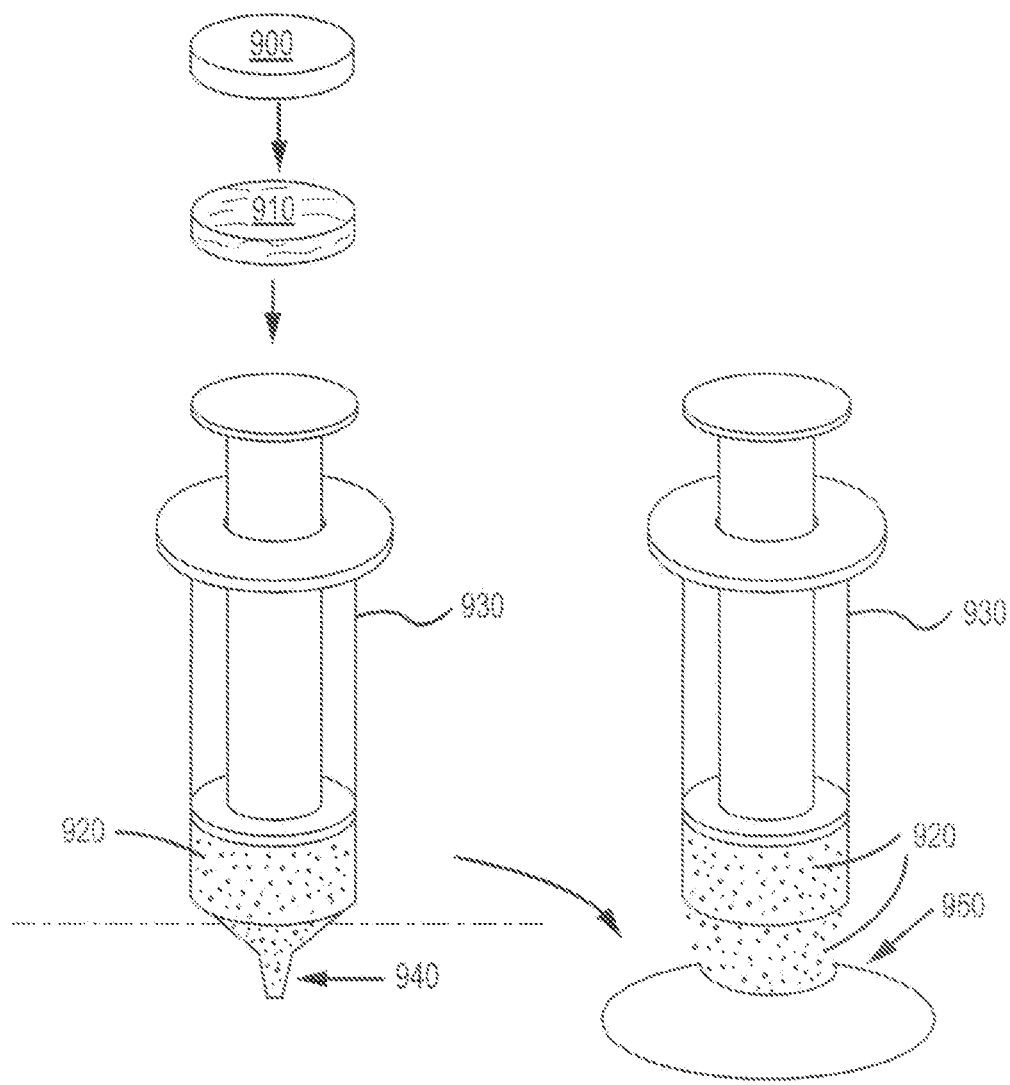
FIG. 9 illustrates the processing and packaging of a sealant matrix composition according to embodiments of the present invention.

Pulverized PEG Cake Material 400 mg premixed CoSeal™, 1 g FloSeal™ (e.g. pH 7.1 to 9.5; particle diameter 70 to 400 nm), and 2 to 3 cc of $H_2O$ were combined into a mixed paste, and lyophilized under a 22 hour cycle to form a cake. As depicted in FIG. 9, the cake 900 was then cracked 910, crushed, and broken powder form 920, and placed in a syringe 930 (e.g. 5 cc or 10 cc syringe). The tip 940 of the syringe barrel was removed with a blade, the powdered mixture 920 was applied to an injury site 950, and sealant activity was observed in situ. Exemplary results are discussed in Examples 10-12. In another embodiment, cake were prepared from a three component slurry as described in Table 7.

TABLE 7

| Sample | Premixed Two-Component PEG | FloSeal ™ | $H_2O$ | PEG % |
|---|---|---|---|---|
| 1 | 360 mg | 500 mg | 2.3 cc | 42% |
| 2 | 200 mg | 500 mg | 1.2 cc | 48% |

Test results on exemplary formulations according to some embodiments revealed the following characteristics shown in Table 8.

TABLE 8

| Sample | FloSeal ™ pH | Weight of (ratio) FloSeal ™ | Weight of Mixed PEG | Particle Diameter FloSeal ™ |
|---|---|---|---|---|
| 1 | 9.2 | 5 g | 2.5 g | 294 μm |
| 2 | 7.7 | 5 g | 2.5 g | 308 μm |

Example 19

Preparation of Sealant Matrix Composition Fused Pads

Figure 10:
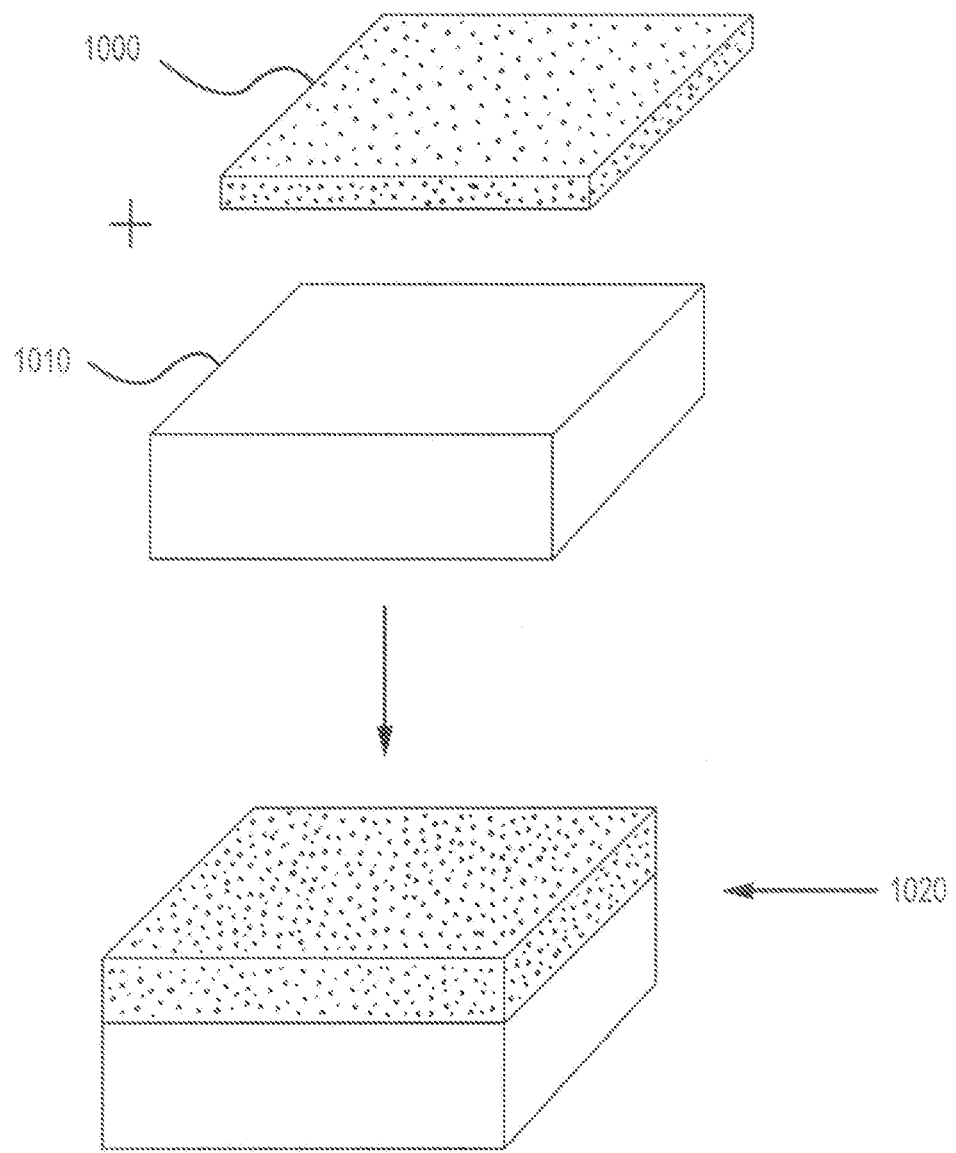
FIG. 10 illustrates the processing and packaging of a sealant matrix composition according to embodiments of the present invention.

PEG pads were prepared with melted CoSeal™ premixtures. Three component powders were prepared by mixing FloSeal™ powder of different pH values and premixed CoSeal™ (e.g. both PEG components in powder form) according to various weight ratios. Lyophilized collagen sponges were used as a back-up support pad to mount the melted three component mixture. In one embodiment, as depicted in FIG. 10, 0.5 to 1 g of sealant matrix composition 1000 was placed on top of a 3×3 $cm^2$ section of sponge 1010. The sponge and sealant matrix were baked in an oven at 60 to 70° C. for 1 to 2 minutes, and allowed to cool in a desiccator to minimize or prevent contact with the air. The sealant matrix powder was observed to form a coarse film and attach to the sponge to form a fused pad 1020. In related embodiments, several sponges were prepared, each having dimensions of 3×3×0.3 $cm^3$. Some sponges were coated with a three component mixture of first and second cross-linkable components and a hydrogel-forming component. Some sponges were coated only with a two component mixture of first and second cross-linkable components. All fused pads were tested in situ on a liver lesion site. Results are shown in Table 9.

TABLE 9

| Fused cake sponge sample | Formulations of three components | | | | In vivo performance Bleeding flow |
|---|---|---|---|---|---|
| | FloSeal ™ pH | FloSeal ™ wt. (g) | CoSeal ™ wt. (g) | Wt. of three components mounted on sponge (g) | |
| 1 | 9 | 0.5 | 0.2 | 0.4 | minimal or no seal |
| 2 | 8 | 0.5 | 0.2 | 0.4 | minimal or no seal |
| 3 | 8 | 0.5 | 0.2 | 0.4 | minimal or no seal |
| 4 | n/a | 0 | 0.5 | 0.4 | minimal or no seal |
| 5 | n/a | 0 | 0.5 | 0.4 | minimal or no seal |
| 6 | 9 | 1 | 0.4 | 0.8 | seal |

In related embodiments, several powdered compositions were prepared. Some compositions included a three component mixture of first and second cross-linkable components and a hydrogel-forming component. Some compositions included only a two component mixture of first and second cross-linkable components. All compositions were tested in situ on a liver lesion site. Results are shown in Table 10.

TABLE 10

| Sample | FloSeal™ pH | FloSeal™ wt. (g) | CoSeal™ wt. (g) | Wt. of three components applied to lesion (g) | In vivo performance Bleeding flow |
|---|---|---|---|---|---|
| 1 | 9 | 0.5 | 0.2 | 0.4 to 0.5 | minimal or no seal |
| 2 | 8 | 0.5 | 0.2 | 0.4 to 0.5 | minimal or no seal |
| 3 | 9 | 0.5 | 0.2 | 0.4 to 0.5 | minimal or no seal |
| 4 | n/a | 0 | 0.5 | 0.4 to 0.5 | minimal or no seal |
| 5 | n/a | 0.01 lysine | 0.5 | 0.4 to 0.5 | minimal or no seal |

Example 20

Effect of γ-Radiation on In Vivo Performance

Powdered sealant matrix compositions and sponge-mounted sealant matrix compositions were prepared and some were γ-radiated to determine the effects of γ-rays on in vivo performance. No effects were observed, as shown in Table 11.

TABLE 11

| | FloSeal™ pH | FloSeal™ wt. (g) | CoSeal™ wt. (g) | Wt. of three components mounted on sponge (g) | In vivo performance Bleeding flow |
|---|---|---|---|---|---|
| Sponge Sample | | | | | |
| 1 | 9 | 0.5 | 0.2 | 0.7 | seal |
| 2 | 8 | 0.5 | 0.2 | 0.7 | seal |
| 3 (γ) | 9 | 0.5 | 0.2 | 0.7 | seal |
| 4 (γ) | 8 | 0.5 | 0.2 | 0.7 | seal |
| 5 | 9 | 0.5 | 0.2 | 0.7 | seal |
| 6 | 8 | 0.5 | 0.2 | 0.65 | seal |
| 7 | 8 | 0.5 | 0.2 | 0.6 | seal |
| Powder Sample | | | | | |
| 1 | 9 | 0.5 | 0.2 | 0.5 | seal |
| 2 | 8 | 0.5 | 0.2 | 0.5 | seal |
| 3 (γ) | 9 | 0.5 | 0.2 | 0.5 | seal |
| 4 (γ) | 8 | 0.5 | 0.2 | 0.5 | seal |

Example 21

Effect of pH on In Vivo Performance

In vivo studies were performed to evaluate the effect of pH values of a hydrogel-forming component, and the effect of manual application methods, on in situ cross-linking. A Floseal™ of pH 6.75 in a first sealant composition and a FloSeal™ of pH 9.5 in a second sealant composition were compared. In some cases, the sealant matrix composition was manually held against the lesion, and in other cases the sealant matrix composition was applied to or placed on the lesion without holding. The composition having Floseal™ of pH 6.75 appeared to provide about 10 to 30 seconds slower reaction time than the composition having Floseal™ of pH 9.5. Exemplary study results are shown in Table 12. It is thought that the pH of a hydrogel-forming component may play a role in the early stages of a cross-linking reaction. The pH of a hydrogel-forming component may effect the speed of gel formation in a wet environment (e.g. where bleeding is already occurring). In some cases, if cross-linking does not occur quickly enough, the sealant composition may be pushed away from the lesion site.

TABLE 12

| Powder Sample | FloSeal™ pH | FloSeal™ wt. (g) | CoSeal™ wt. (g) | Wt. of three components applied to lesion (g) | Bleeding flow | Application site/method |
|---|---|---|---|---|---|---|
| P | 7 | 0.5 | 0.2 | 0.5 | no seal | liver square (w/o holding) |
| P | 9 | 0.5 | 0.2 | 0.5 | seal | liver square (w/o holding) |

TABLE 12-continued

Formulations of three components

| Powder Sample | FloSeal™ pH | FloSeal™ wt. (g) | CoSeal™ wt. (g) | Wt. of three components applied to lesion (g) | Bleeding flow | Application site/method |
|---|---|---|---|---|---|---|
| P | 7 | 0.5 | 0.2 | 0.5 | seal | liver square (w/ holding) |
| P | 9 | 0.5 | 0.2 | 0.5 | seal | liver square (w/ holding) |
| P | 7 | 0.5 | 0.2 | 0.5 | seal | splenic vein (w/ holding) |
| P | 9 | 0.5 | 0.2 | 0.5 | seal | splenic vein (w/ holding) |

Example 22

Use of SURGIFOAM™ as Hydrogel-Forming Component

Mixtures of powdered COH102 (pentaerythritoltetrakis-[1-(1'-oxo-5' succinylpentate)-2-poly(oxyethylene)glycol] ether), powdered COH206 (pentaerythritol tetrakis-[mercaptoethyl-poly(oxyethylene)glycol]ether), and SURGIFOAM™ Absorbable Gelatin Powder (Ethicon, Somerville, N.J.) were blended at ratios of 1:1:2, 1:1:4, and 1:1:8 by weight and filled into modified 5 mL syringes. The resulting mixtures were substantially dry, free-flowing powders. For each composition, two grams were applied with gentle compression to a surgically created lesion (approximately 1 cm×1 cm×0.3 cm deep) on the liver of a pig. For each of the compositions, compression was removed after one minute. The COH102 and COH206 in each composition reacted with each other in the wet environment of the lesion, creating a cross-linked hydrogel that incorporated the SURGIFOAM™ powder and physically sealed the lesion site. No bleeding was observed from any of the sites treated with the compositions. After irrigating the treated lesions with saline solution 5 minutes after application, no rebleeding was observed. Examination of the treated sites two hours later also showed no bleeding.

Example 23

In Vivo Performance of Sealant Matrix Composition with Clotting Agent

A sealant matrix composition powder was prepared, containing FloSeal™ and CoSeal™ (pre-mixed) in a 4:1 weight ratio. In some embodiments, this ratio provides a degree of cross-linking effective to achieve desired levels of chemical polymerization and adherence of the composition to tissue. Thrombin powder was added to the sealant matrix composition powder at various concentrations. The resulting mixture was tested in an animal study that involved measuring bleeding scores in liver squares and comparing hemostatic efficiency of the resulting mixture with sealant matrix compositions that did not contain thrombin.

Testing materials included 0.1 g of pentaerythritol tetrakis [merkaptoethylpoly(oxyethylene)]ether, 0.1 g of Pentaerythritol tetrakis[1-1'-oxo-5'-succinimidylpentanoate)-2-poly(oxoethylene)glycole]ether, 0.8 g of crosslinked gelatin particle (FloSeal™), and various concentrations (5 k, 2.5 k, 1.25 k, and 0.625 k u/g) of thrombin. In a mixing experiment, the four components of the resulting mixture were mixed with a tumble mixer. In a reconstitution experiment, four ml of thrombin solution (1250 u/ml) was mixed with 0.8 g of FloSeal, and then freeze fried for 22 hrs. Then dried mixture was mixed with CoSeal™ powder using a tumbler mixer. Without being bound to any particular theory, it is thought that the reconstituted thrombin formulation contains thrombin molecules that have penetrated into the matrix of FloSeal™ so that thrombin may remain in the sealant matrix barrier to enhance hemostatic efficacy. In a pad experiment, a pad was prepared by mounting the resulting four component mixture (sealant matrix composition plus thrombin) on top of a Gelfoam sponge, melting the mixture, and allowing it to cool and solidify. The oven temperature was set at about 60° C. to about 65° C. for about one minute.

In an in vivo test, an animal was heparinized to activate clotting time to reach 3-5 times higher than base line. Formulations were examined on the bleeding space of liver square (1 cm×1 cm×0.2 cm) that was surgically produced on a porcine liver. The lesion was irrigated immediately after the 5 minute reading to remove excess powder. Treated lesions areas were scored at 1, 5, 10, and 30 minutes. Materials were polymerized upon the contact with blood then tightly adhered to the lesion. The sealant matrix barrier mechanically sealed the bleeding areas to act as a mechanical sealant by bonding to the tissues. In an in vitro test, thrombin was heated at about 60° C. for 5 minutes and found to be fully active. In a prepared Gelfoam pad, it was found that thrombin activity was lost.

Results of an acute in-vivo evaluation are provided in Table 13. Bleeding from the lesions were scored from "0" as no bleeding to "4" as severe bleeding. Based on the observed bleeding scores here, all samples tested showed no bleeding. No significant advantage was observed from the addition of thrombin to the sealant matrix composition. The use of thrombin did not show any benefits in primary hemostasis, although it may augment secondary hemostasis/clot formation and wound healing.

TABLE 13

| Lot No. | Sealant Matrix Composition | Thrombin (unit/g) Mixed or Reconstituted | 1' | 5' | 10' | 20' |
|---|---|---|---|---|---|---|
| 1 | no thrombin | 0 | 0 | 0 | 0 | |
| 2 | with thrombin | 625, mixed | 0 | 0 | 0 | 0 |
| 3 | with thrombin | 2500, mixed | 0 | 0 | 0 | 0 |
| 4 | with thrombin | 5000, mixed | 0 | 0 | 0 | 0 |
| 5 | with thrombin | 1250, mixed | 0 | 0 | 0 | 0 |
| 1 | no thrombin | 0 | 0 | 0 | 0 | 0 |
| 5 | with thrombin | 1250, mixed | abort | | | |
| 5 | with thrombin | 1250, mixed | 0 | 0 | 0 | 0 |
| 4 | with thrombin | 5000, mixed | 0 | 0 | 0 | 0 |
| 4 | with thrombin | 5000, mixed | 0 | 0 | 0 | 0 |
| 1 | no thrombin | 0 | 0 | 0 | 0 | 0 |
| 6 | with thrombin | 625, reconstituted | 0 | 0 | 0 | 0 |
| 7 | with thrombin | 2500, reconstituted | abort | | | |
| 7 | with thrombin | 2500, reconstituted | 0 | 0 | 0 | 0 |

TABLE 13-continued

| Lot No. | Sealant Matrix Composition | Thrombin (unit/g) Mixed or Reconstituted | 1' | 5' | 10' | 20' |
|---|---|---|---|---|---|---|
| 7 | with thrombin | 2500, reconstituted | 0 | 0 | 0 | 0 |
| 8 | no thrombin (sponge) | 0 | 0 | 0 | 0 | 0 |
| 9 | with thrombin (sponge) | 2500, mixed | 0 | 0 | 0 | 0 |

Example 24

Effect of PEG Concentration on Gel Strength

Figure 11:
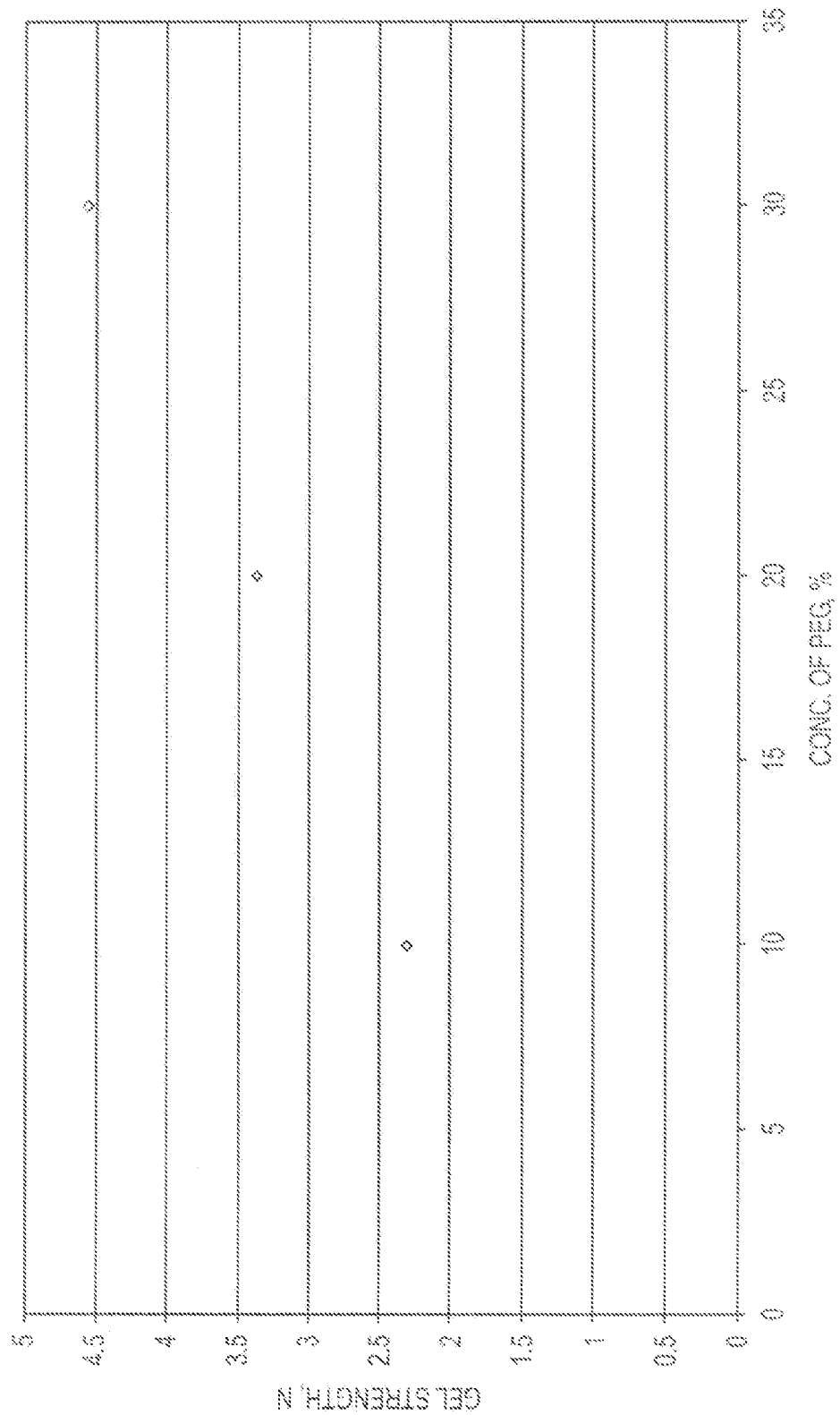
FIG. 11 illustrates the effect of PEG concentration on gel strength, according to embodiments of the present invention.

The effect of PEG concentration on gel strength is shown in Table 14 and FIG. 11, according to one embodiment of the present invention. Tensile tests were run following the gel formation. Gels were prepared by allowing reaction of three components powder (e.g. sealant matrix composition that includes first and second cross-linkable components and a hydrogel-forming component) in plastic molds (3×1×0.3 cm). Porcine plasma (1 ml, Baxter animal number S-264) was added to a sealant matrix composition powder (0.60-0.65 g) to initiate gel formation then allowed to cure at room temperature for approximately 30 minutes. Both ends of the gel were taped with scotch tape using cyanoacrylate glue to create the gripping spaces for pulling apart (1×1 cm). From the tensile testing, Peak force (N) and deflection at maximum load (cm) were measured to extend the gel until the break. 1×0.3 cm is the effective surface area. The original effective length of gel is 1.0 cm. Applying a normal stress to the rectangular shape of gel until it breaks by Chatillon TCD200 tester was the determination factor of the tensile strength. Results of the test showed that a higher concentration of polymer can increase the strength of the sealant matrix composition gel.

TABLE 14

| Sample Number | Material Tested | Effective Area, cm square | Speed mm/min | Curing time min | Force N | F/0.3 cm2 | F/0.1 cm2 |
|---|---|---|---|---|---|---|---|
| 334-25-1 | 10% PEG | 1 × 0.3 | 12.7 | 60 | 2.69 | | 8.97 |
| 334-25-2 | 10% PEG | 1 × 0.3 | 12.7 | 60 | 2.12 | | 7.07 |
| 334-25-3 | 10% PEG | 1 × 0.3 | 12.7 | 60 | 2.11 | | 7.03 |
| Ave. | | | | | 2.31 | | 7.69 |
| Stdev. | | | | | 0.33 | | 1.11 |
| 334-25-4 | 20% PEG | 1 × 0.3 | 12.7 | 55 | 3.80 | | 12.67 |
| 334-25-5 | 20% PEG | 1 × 0.3 | 12.7 | 60 | 3.93 | | 13.10 |
| 334-25-6 | 20% PEG | 1 × 0.3 | 12.7 | 55 | 3.47 | | 11.57 |
| 334-25-7 | 20% PEG | 1 × 0.3 | 12.7 | 60 | 2.33 | | 7.76 |
| Ave. | | | | | 3.38 | | 11.28 |
| Stdev. | | | | | 0.73 | | 2.43 |
| 316-80-1 | 30%, PEG | 1 × 0.3 | 12.7 | 70 | 4.04 | | 13.46 |
| 316-80-2 | 30%, PEG | 1 × 0.3 | 12.7 | 60 | 4.55 | | 15.17 |
| 316-80-3 | 30%, PEG | 1 × 0.3 | 12.7 | 60 | 5.12 | | 17.06 |
| 316-80-4 | 30%, PEG | 1 × 0.3 | 12.7 | 60 | 4.68 | | 15.60 |
| 316-80-5 | 30%, PEG | 1 × 0.3 | 12.7 | 55 | 4.49 | | 14.97 |
| 316-80-6 | 30%, PEG | 1 × 0.3 | 12.7 | 60 | 4.52 | | 15.07 |
| Ave. | | | | | 4.57 | | 15.68 |
| Stdev. | | | | | 0.35 | | 0.97 |

Example 25

Effect of PEG Concentration on Swelling Ratio

Figure 14:
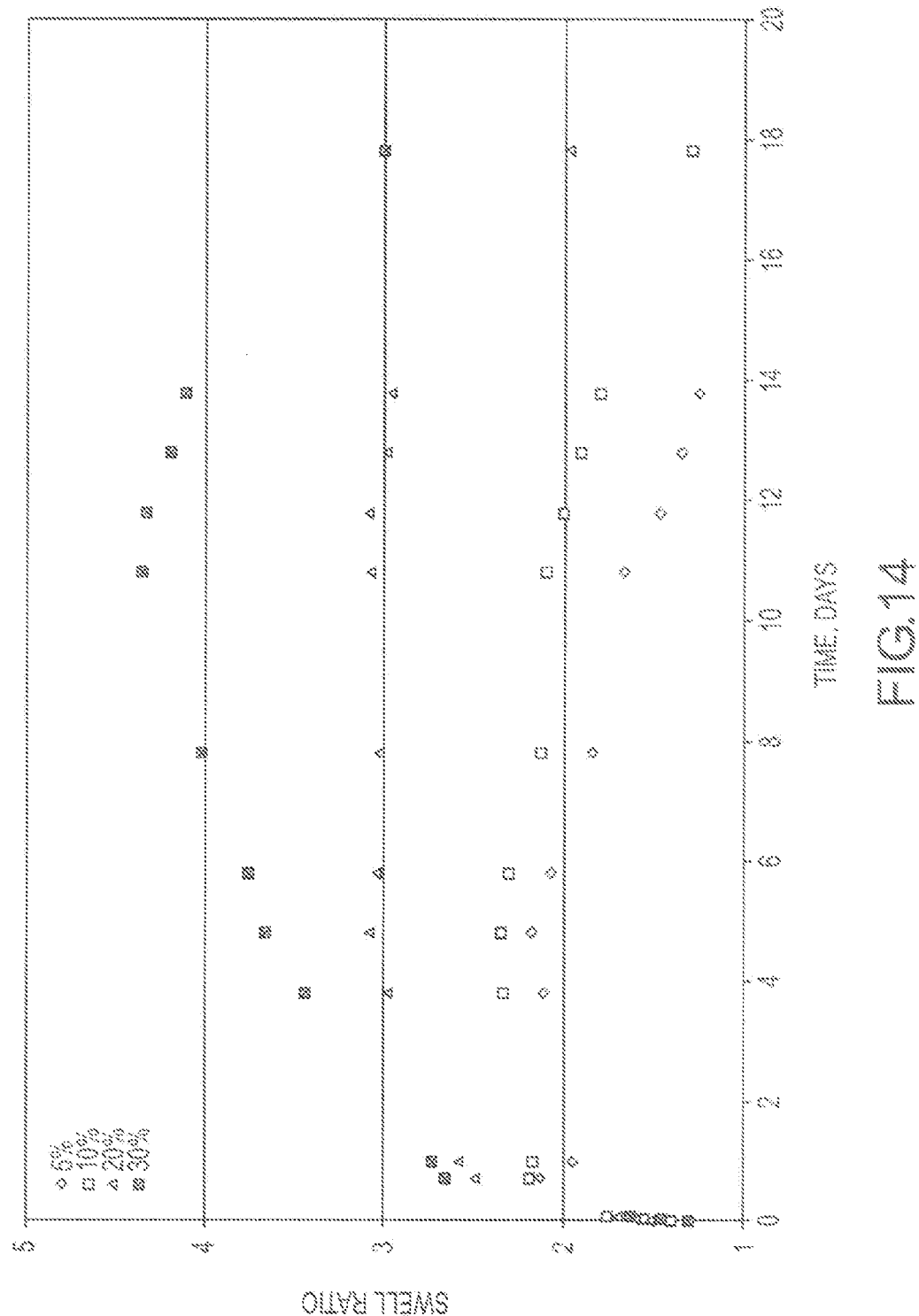
FIG. 14 illustrates the effect of PEG concentration on swelling ratio, according to embodiments of the present invention.

The effect of PEG concentration on swelling ratio is shown in FIGS. 12, 13, and 14, according to one embodiment of the present invention. Swelling studies were carried out for the characterization of sealant matrix composition gels. When in contact with an aqueous environment, the hydrophilic polymer swells to form a hydrogel. Once a gel is formed, water molecules diffuse freely through a rather loose network formed by swollen FloSeal™ particles. Upon further addition of water, COH102-COH206 contacts are broken and individual polymer molecules are dissolved in water. Sealant matrix composition gels were prepared by mixing CoSeal™ and FloSeal™ at four different concentrations (5%, 10%, 20%, and 30% w/w) of polymer and by reactions with the same amount of porcine plasma (1.7 ml/g powders). The gel was cured for 30 minutes and then allowed to swell in saline at room temperature. Periodically, buffer was drained and the weight of the remaining gel was determined. The change in the weight of gel was monitored. The swelling ratio, Q, was calculated from the following equation:

$$Q = W^*/W$$

where $W^*$ is the wet weight and $W$ is the original weight. The swelling ratio increased with increasing of polymer concentration. Without being bound by any particular theory, the apparent decline in swell ratio may be interpreted as a loss of gel material, as the gel slowly eroded. The end of the experiment is scored as the time when the gel disintegrates into several small pieces or becomes so slimy and weak that it is impossible to decant the free buffer from the gel. Water continues to penetrate toward the core and finally gel is converted to a viscous solution of PEG and gelatin particles. It took about 2-3 weeks for all materials to fall apart (FIG. 14). It appears that percent CoSeal™ in a sealant matrix composition powder can have a profound impact on the stability of a sealant matrix composition gel. The dissolution rate of the sealant matrix composition gel varies depending on the crosslinking degree of polymers. Results showed that the higher concentration of CoSeal™ can cause a stronger gel stability and can also cause more swell. The relative persistence of such gel in vitro may be expected to be similar to that in vivo.

The above examples provide ample illustration that compositions according to the present invention can be effective sealants. The compositions can polymerize in situ with physiological liquid or blood, and can seal or adhere to tissue very tightly.

Although the foregoing invention has been described in some detail by way of illustration and example, for purposes of clarity of understanding, it will be obvious that certain changes and modifications may be practiced within the scope of the appended claims. All patents, publications, articles, books, and other references materials discussed herein are incorporated by reference for all purposes.

Example 26

Assessment of Hemostatic Properties in Animal Models of Certain Formulations

Formulation No. 334-77

One gram of PEG-A powder (Pentaerythritol tetrakis [merkaptoethylpoly-oxyethylene]ether, MW 10,000), 1 g of PEG-B powder (Pentaerythritol tetrakis[1-1'-oxo-5'-succinimidylpentanoate-2-poly-oxoethyleneglycole]ether, MW 10,000), and 8 g of FloSeal™ were placed in a mixing bottle (50 ml size) and loaded into the Inversina Tumbler Mixer for mixing. Mixture of three components were blended for 10 minutes until fully mixed. Six syringes (5 ml size) were filled with about 1.5 g of the mixture.

Formulation No. 334-77-1

A 1.5 g sample of Formulation No. 334-77 was mounted on a piece of Gelfoam (3×4 cm², Compressed Gelfoam, Upjohn manufactured, NDC 0009-0353-01). Gelfoam topped with the sample was baked in a vacuum oven at 60-65° C. for 1 min until the sample began to melt. The material was then allowed to cool and solidify. Two pieces of the resulting cake on Gelfoam were placed in a pouch inserted with desiccant and sealed.

Formulation No. 334-77-4

A sample of Formulation No. 334-77 was placed on a piece of collagen sponge and baked. Sponges were prepared by lightly crosslinking collagen fibers by glutaraldehyde solution (5 k ppm) and by freeze-drying collagen solution (1.0%) using VirTis Genesis Freeze Dryers. A collagen pad (3×4 cm$^2$) was carefully layered with a 1.5 g sample of Formulation No. 334-77, then heated in a vacuum oven at 60-65° C. for 1 min until the sample began to melt. The material was then allowed to cool and solidify. Each resulting collagen pad was placed in a pouch inserted with desiccant and sealed.

Methods:

Surgical Procedures:

Animals (NZW rabbits, female, weight approximately 3 kg) were anesthetized and received intravenous heparinization at a dose of 4.000 IU/kg 30 minutes prior to partial liver resection.

Liver Resection Model:

A median laparotomy was performed and the left lobe of the liver exposed and clamped. Part of the left lateral liver lobe was resected. Oozing was controlled by application of the test item. Application and setting time was standardized not to exceed 300 seconds. The hemostatic clamp was removed five minutes later when primary hemostasis was expected to be achieved.

Liver Abrasion Model:

A median laparotomy was performed and the left lobe of the liver exposed. A superficial circular lesion with a diameter of 2 cm and a depth of 2 mm was abraded on the surface of the liver lobe. This was accomplished using a drilling machine with a grinding disc attachment (bore grinder PROXXON FBS 230/E; grit size P40, rotational speed 5.000/min). The resultant small vessel or capillary bleeding or oozing thus generated was treated with one of the formulations.

After allowing an observation period of 15 minutes, the left liver lobe was returned to its original position in the abdominal cavity. If hemostasis is achieved, the abdomen will be closed and the Omentum resected (Synthofil® 2/0). The muscle and skin incision will be sutured separately using Synthofil® 2/0 as interrupted sutures in a two-level manner.

After 24 hours, the animals were sacrificed in anesthesia by an overdose of Pentobarbital Natrium (approx. 320 mg i.v./animal). After euthanization an autopsy was performed. The abdomen was visually inspected for the presence of blood and/or blood clots resulting from rebleeding. If present, blood and/or blood clots were swabbed using pre-weighed surgical swabs, and the weight determined. If no hemostasis was achieved, animals were sacrificed by an overdose of Pentobarbital Natrium (approx. 320 mg i.v./animal) and only primary endpoints will be evaluated.

Results:

The present study was aimed to assess the hemostatic properties of formulations #334-77, #334-77-1 and #334-77-4). Two very harsh hemostasis models were used: (1) the liver resection and (2) the liver surface model in highly heparinized rabbits.

After applying formulation #334-77 powder onto the bleeding wound it was found helpful to press the formulation onto the wound surface to obtain hemostasis. It was difficult to achieve this pressure with a dry surgical latex glove, since the powder had more adherence to the glove than to the wound. However, application of pressure with a wet glove was easier. The formulation formed a tight membrane after it came into contact with the moisture of blood. After application it lead to hemostasis in many cases, even in the harsh models used in this example. If hemostasis was not completely achieved after the first application, and there was an oozing bleeding underneath the layer formed, it was difficult to adequately stop the bleeding simply by the application of more formulation #334-77. It may be difficult to restrict application of the formulation only to the place where it is needed to stop the bleeding as the powdered formulation can fall into the abdominal cavity and adhere to the abdominal cavity if sufficient care is not taken. Therefore, proper application of formulation #334-77 is helpful.

In contrast, formulation #344-77-4 could easily be applied in a layer of constant thickness over a large area of tissue and with sufficient pressure in order to obtain hemostasis. Formulation #344-77-4, with the native collagen pad backing, remained adherent to the liver lobe after application and acted as a hemostat and glue, gluing the pad onto the wound and the liver capsule. Such a biodegradable backing can add more efficacy to the powder component in achieving hemostasis. The biodegradable backing can also confer flexibility to the formulation, allowing the formulation to be bent over edges of a resection during application. Two animals were treated with this formulation, one in the surface model and one in the resection model. Acute hemostasis was obtained in both models. Only the animal treated in the surface model survived with no postsurgical bleedings for 24 h. The collagen fleece was still at the site of application after 24 h. The animal treated in the resection model bled overnight to death and the fleece was detached. A difference between the two experiments was that in the first the fleece was pressed in the dry state onto the wound and in the second pressure with a wet gauze swab was used. The findings are shown in Table 15.

TABLE 15

| Animal | Experiment | |
|---|---|---|
| 1 | 1a | Liver resection model: (#334-77-1) Left liver lobe. Application without clamping. During application the Gelfoam pad was brittle and stiff and could not be bent in dry state around the edges of the resection. Was pressed 2 min with a wetted gauze swab (0.9% NaCl) on the resection surface and the intact liver capsule around the resection. The powder adhered firmly to the wound surface but not to the Gelfoam backing. Non-adhering powder was rinsed with 0.9% NaCl. Bleeding was stopped with exception of one point on the edge of the resection were oozing bleeding was observed. |
| | 1b | Surface model: (#334-77-1) Left median liver lobe. Application without clamping. Formulation #334-77-1 was pressed 2 min with a wetted gauze swab (0.9% NaCl) on the wound surface. The Gelfoam backing was removed. The formulation was adhering to the wound. Bleeding was stopped. |
| 2 | 2a | Liver resection model: (#334-77) Left lateral liver lobe. Formulation #334-77 was applied to the bleeding surface and pressed with the dry latex glove. The powder adhered more |

TABLE 15-continued

| Animal | Experiment | |
|---|---|---|
| | 2b | strongly to the glove as to the wound surface. The formulation layer was removed with the glove.<br>Liver resection model: (#334-77)<br>Same left lateral liver lobe as in 2a. #334-77 was applied with the wet glove and pressed 10 s to the wound surface. No adherence of powder to the glove. A layer was formed over the wound surface. Oozing bleeding beneath the powder was observed. |
| | 2c | Liver resection model (#334-77)<br>Left median liver lobe, application with clamping. Formulation #334-77 was applied on the bloody surface and pressed on the surface with a metal foil. The clamp was released after 5 min. Slight oozing bleeding at the edge of the resection. It was tried to stop this bleeding by applying more formulation. Bleeding could not be stopped completely. The powder layer was removed. The layer formed a tight membrane but with only little adherence to the wound surface. |
| | 2d | Liver resection model: (#WR334-77)<br>Same liver lobe as in 2c, but a new cut was done in order to promote bleeding. Application after clamping the liver lobe. Formulation was pressed 2 min with the scalpel on the wound. Bleeding could not be stopped |
| 3 | 3a | Surface model: #WR334-77 + equine collagen pad.<br>#344-77 powder was spread on a thin layer of an equine collagen pad. Holes were punctured in the collagen pad with an injection needle from the side with the formulation layer. Some formulation pressed into the holes. The formulation layer was thinner than as in the formulation variants. The fleece was applied dry, without clamping the liver lobe. The fleece was pressed with the glove for 2 min. No bleeding was observed. The pad was removed. Good adherence to the liver capsule and less adherence to the wound surface was observed. |
| | 3 b | Surface model: Formulation-Collagen-Pad (#334-77-4)<br>Same wound as in 3a. The pad was applied in dry state and pressed for 2 min on the wound surface. The pad was more flexible (bendable) compared to the fleece with the Gelfoam backing. This was favorable for the ease of application. The formulation did not detach from the collagen pad. The whole formulation-collagen pad was adhering to the wound and liver capsule. No bleeding was observed). The collagen pad was wetted with 0.9% NaCl and the rabbit closed. The animal survived 24 h than it was sacrificed. In the post mortem examination the fleece was on place and no bleeding occurred during 24 h. |

What is claimed is:

1. A method of treating a tissue of an individual, the method comprising:
    applying a dry solid sealant composition to the tissue of the individual, the sealant composition comprising a first cross-linkable component, a second cross-linkable component, and a hydrogel-forming component characterized by an equilibrium swell value of between about 400% and about 1300%; wherein:
    the concentration of combined first and second cross-linkable components is from 5% to 75% of the total mass of the sealant composition and the concentration of the hydrogel-forming component is from 95% to 25% of the total mass of the sealant composition;
    the first and second cross-linkable components are configured to react by cross-linking upon contact between the sealant composition and a tissue to form a porous matrix having interstices, and the hydrogel-forming component is configured to swell, by absorption of moisture following the tissue contact to form a hydrogel to fill at least some of the interstices;
    the first cross-linkable component comprises a multi-nucleophilic polyalkylene oxide having m nucleophilic groups, and the second cross-linkable component comprises a multi-electrophilic polyalkylene oxide having n electrophilic groups, wherein m and n are each greater than or equal to two, and wherein m+n is greater than or equal to five; and
    the tissue comprises a bleeding site, and the matrix and interstitial hydrogel are configured to seal the bleeding site.

2. The method according to claim 1, wherein each of the first and second components is present as a gel.

3. The method according to claim 1, wherein the hydrogel forming component comprises a biologic polymer selected from the group consisting of gelatin, collagen, albumin, hemoglobin, fibrogen, fibrin, casein, fibronectin, elastin, keratin, laminin, and derivatives and combinations thereof.

4. The method according to claim 1, wherein the sealant composition is fixed on a support, and wherein the support is porous and comprises a member selected from the group consisting of a pad, a sheet, a film, and a sponge.

5. The method according to claim 4, wherein the support comprises a member selected from the group consisting of collagen, fibrin, cellulose, and chitosan.

6. The method according to claim 1, wherein the first component nucleophilic polymer comprises a member selected from the group consisting of a dilysine, a trilysine, a quatralysine, a pentalysine, a dicysteine, a tricysteine, a quatracysteine, a pentacystein, and an oligopeptide or polypeptide comprising two or more lysines or cysteines.

7. The method according to claim 1, wherein the second component electrophilic polymer comprises two or more succinimidyl groups.

8. The method according to claim 1, wherein the second component comprises a polyethylene glycol containing a succinimidyl group.

9. The method according to claim 1, wherein the sealant composition further comprises an active agent.

10. The method according to claim 1, wherein the sealant composition further comprises a hemostatic agent selected from the group consisting of thrombin, fibrinogen, and a clotting agent.

11. A method of treating a tissue of a living individual, the method comprising:
obtaining a dry solid sealant composition, the sealant composition comprising a first cross-linkable component, a second cross-linkable component and a hydrogel-forming component characterized by an equilibrium swell value of between about 400% and about 1300%, wherein:
the first and second cross-linkable components are capable of substantially immediate cross-linking to form a porous matrix having interstices upon contacting the mixed powder composition to a tissue, and the hydrogel-forming component does not cross-link with the first cross-linkable component or the second cross-linkable component and is configured to swell by absorption of moisture following the tissue contact;
the first cross-linkable component comprises a multi-nucleophilic polyalkylene oxide having m nucleophilic groups, and the second cross-linkable component comprises a multi-electrophilic polyalkylene oxide having n electrophilic groups, wherein m and n are each greater than or equal to two, and wherein m+n is greater than or equal to five;
the hydrogel-forming component is in a concentration of between 25% and 95% mass percent of the composition; and
the tissue comprises a bleeding site, and the matrix and interstitial hydrogel are configured to seal the bleeding site; and
applying the sealant composition to the tissue of the individual.

12. The method according to claim 11, wherein the sealant composition is fixed on a support, and wherein the support is configured to degrade at approximately the same rate in vivo as the sealant composition.

13. The method according to claim 11, wherein the sealant composition is fixed on a support, and wherein the support comprises a swelling factor of about 1.3 to about 1.5 times.

14. The method according to claim 11, wherein the first and second components cross-link under physiological conditions.

15. The method according to claim 11, wherein the sealant composition is applied to the tissue of the individual in the absence of a high pH buffer.

16. A method of treating a tissue of a living individual, the method comprising:
applying a dry solid sealant composition to the tissue of the individual, the sealant composition comprising a first cross-linkable component, a second cross-linkable component, and a hydrogel-forming component characterized by an equilibrium swell value of between about 400% and about 1300%, wherein the sealant composition is fixed on a biocompatible support comprising a member selected from the group consisting of a protein, a carbohydrate, and a synthetic polymer, and wherein:
the concentration of combined first and second cross-linkable components is from 5% to 75% of the total mass of the sealant composition and the concentration of the hydrogel-forming component is from 95% to 25% of the total mass of the sealant composition;
the first and second cross-linkable components are configured to react by cross-linking upon contact between the sealant composition and a tissue to form a porous matrix having interstices, and the hydrogel-forming component is configured to swell, by absorption of moisture following the tissue contact to form a hydrogel to fill at least some of the interstices;
the first cross-linkable component comprises a multi-nucleophilic polyalkylene oxide having m nucleophilic groups, and the second cross-linkable component comprises a multi-electrophilic polyalkylene oxide having n electrophilic groups, wherein m and n are each greater than or equal to two, and wherein m+n is greater than or equal to five; and
the tissue comprises a bleeding site, and the matrix and interstitial hydrogel are configured to seal the bleeding site.

17. The method according to claim 16, wherein the first and second components are physically fixed on the support.

18. The method according to claim 16, wherein the support is previously cross-linked so that the first and second components are not chemically reacted with the support prior to the application.

19. The method according to claim 16, wherein the first and second components are not chemically reacted with one another on the support prior to the application.

20. The method according to claim 16, wherein the biocompatible support is configured to degrade at approximately the same rate in vivo as the sealant composition.

21. The method according to claim 16, wherein the biocompatible support has a degree of porosity to allow blood or other liquids to seep into the support.

22. The method according to claim 16, wherein the first and second components are at least partially contained within the biocompatible support.

23. The method according to claim 16, wherein the tissue comprises muscle, skin, epithelial tissue, smooth, skeletal or cardiac muscle, connective or supporting tissue, nerve tissue, ophthalmic and other sense organ tissue, vascular and cardiac tissue, gastrointestinal organs and tissue, pleura and other pulmonary tissue, kidney, endocrine glands, male and female reproductive organs, adipose tissue, liver, pancreas, lymph, cartilage, bone, oral tissue, mucosal tissue, or spleen or other abdominal organs.

24. The method according to claim 11, wherein the support comprises a swelling factor of about 1.3 to about 1.5 times.

* * * * *